(12) United States Patent
Noe et al.

(10) Patent No.: US 6,706,723 B2
(45) Date of Patent: Mar. 16, 2004

(54) PYRIMIDINE-2,4,6-TRIONE METALLOPROTEINASE INHIBITORS

(75) Inventors: Mark C. Noe, Mystic, CT (US); Lawrence A. Reiter, Mystic, CT (US); Martin J. Wythes, New London, CT (US)

(73) Assignee: Pfizer, Inc., New York City, NY (US)

( * ) Notice: Subject to any disclaimer, the term of this patent is extended or adjusted under 35 U.S.C. 154(b) by 0 days.

(21) Appl. No.: 10/032,837

(22) Filed: Oct. 25, 2001

(65) Prior Publication Data

US 2002/0132822 A1 Sep. 19, 2002

Related U.S. Application Data

(60) Provisional application No. 60/243,314, filed on Oct. 26, 2000.

(51) Int. Cl.[7] .................... C07D 239/62; C07D 417/12; C07D 413/12; A61K 31/505
(52) U.S. Cl. .................... 514/270; 544/299; 544/300; 544/301; 544/302; 544/303; 544/304; 544/306; 544/307
(58) Field of Search ................................. 544/299, 300, 544/301, 302, 303, 304, 306, 307; 514/270

(56) References Cited

U.S. PATENT DOCUMENTS

6,265,578 B1 7/2001 Foley et al. ................. 544/302

FOREIGN PATENT DOCUMENTS

| WO | 9723465 | 7/1997 | ......... C07D/239/62 |
| WO | 9858915 | 12/1998 | ......... C07D/239/00 |
| WO | 9858925 | 12/1998 | ......... C07D/401/12 |
| WO | 0047565 | 8/2000 | ......... C07D/239/62 |

OTHER PUBLICATIONS

Shrimali et al., Chem. Abstract 110:57614, 1989.*
Layzer, Degenerative Diseases of the Nervous System, Cecil Textbook of Medicine, 20th Edition, vol. 2, pp. 2050–2057, 1996.*
Damasio, Alzheimer's Disease and Related Dementias, Cecil Textbook of Medicine, 20th Edition, vol. 2, pp. 1992–1996, 1996.*
Simone, Oncology: Introduction, Cecil Textbook of Medicine, 20th Edition, vol. 1, pp. 1004–1010, 1996.*
Rasmussen et al., Matrix Metalloproteinase Inhibition as a Novel Anticancer Strategy, Pharmcol. Ther. vol. 75, No. 1, pp. 69–75, 1997.*
Chambers et al., Changing Views of the Role of Matrix Metalloproteinases in Metastasis: Review, Journal of the National Cancer Institute, vol. 89, No. 17, pp. 1260–1270, 1997.*
Morris et al., PubMed Abstract (Invasion Metastasis, 17(6):281–96), 1997.*

\* cited by examiner

*Primary Examiner*—Deepak Rao
(74) *Attorney, Agent, or Firm*—Scully, Scott, Murphy & Presser

(57) ABSTRACT

The present invention relates to pyrimidine-2,4,6-trione metalloproteinase inhibitors of the formula

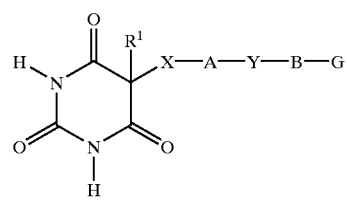

wherein X, Y, A, B and $R^1$ are as defined in the specification, and to pharmaceutical compositions and methods of treating inflammation, cancer and other disorders.

17 Claims, No Drawings

PYRIMIDINE-2,4,6-TRIONE METALLOPROTEINASE INHIBITORS

"This is a nonprovisional patent application filing of co-pending U.S. Provisional Patent Application No. 60/243,314 filed Oct. 26, 2000."

BACKGROUND OF THE INVENTION

The present invention relates to pyrimidine-2,4,6-trione metalloproteinase inhibitors, and to pharmaceutical compositions and methods of treatment of inflammation, cancer and other disorders.

The compounds of the present invention are inhibitors of zinc metalloendopeptidases, especially those belonging to the class of matrix metalloproteinases (also called MMP or matrixin).

The MMP subfamily of enzymes, currently contains seventeen members (MMP-1, MMP-2, MMP-3, MMP-7, MMP-8, MMP-9, MMP-10, MMP-11, MMP-12, MMP-13, MMP-14, MMP-15, MMP-16, MMP-17, MMP-18, MMP-19, MMP-20). The MMP's are most well known for their role in regulating the turn-over of extracellular matrix proteins and as such play important roles in normal physiological processes such as reproduction, development and differentiation. In addition, the MMP's are expressed in many pathological situations in which abnormal connective tissue turnover is occurring. For example, MMP-13 an enzyme with potent activity at degrading type 11 collagen (the principal collagen in cartilage), has been demonstrated to be overexpressed in osteoarthritic cartilage (Mitchel, et al., *J. Clin. Invest.*, 97, 761 (1996)). Other MMPs (MMP-2, MMP-3, MMP-8, MMP-9, MMP-12) are also overexpressed in osteoarthritic cartilage and inhibition of some or all of these MMP's is expected to slow or block the accelerated loss of cartilage typical of joint diseases such as osteoarthritis or rheumatoid arthritis.

It is recognized that different combinations of MMP's are expressed in different pathological situations. As such, inhibitors with specific selectivities for individual MMP's may be preferred for individual diseases.

Matrix metalloproteinase inhibitors are well known in the literature. Hydroxamic acid MMP inhibitors are exemplified in European Patent Publication 606,046, published Jul. 13, 1994. Several pyrimidine-2,4,6 trione MMP inhibitors are referred to in PCT publication WO 98/58925, published Dec. 30, 1998. PCT publication WO 00/47565, published Aug. 17, 2000 refers to certain aryl substituted pyrimidine-2,4,6-trione MMP inhibitors. U.S. Non-provisional application Ser. No. 09/635156, filed Aug. 9, 2000 (which claims priority to U.S. Provisional application No. 60/148547 filed Aug. 12, 1999) refers to heteroaryl substituted pyrimidine-2,4,6 trione MMP inhibitors. U.S. Provisional Application entitled "Spiro-Pyrimidine-2,4,6-Trione Metalloproteinase Inhibitors", filed Oct. 26, 2000, refers to certain 5-spiro pyrimidin-2,4,6-triones. Barbituric acids and methods for their preparation are well known in the art, see for example Goodman and Gilman's, "*The Phamacological Basis of Therapeutics*," 345–382 (Eighth Edition, McGraw Hill, 1990). Each of the above referenced publications and applications is hereby incorporated by reference in its entirety.

SUMMARY OF THE INVENTION

The present invention relates to compounds of the formula:

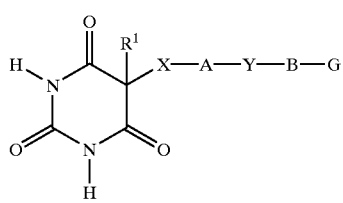

I wherein A is optionally substituted $(C_6-C_{10})$aryl or $(C_2-C_{10})$heteroaryl;

B is optionally substituted $(C_6-C_{10})$aryl, $(C_3-C_8)$cycloalkyl, $(C_1-C_{10})$heteroaryl, $(C_1-C_{10})$heterocyclic, $(C_6-C_{10})$aryl-$(C_1-C_4)$alkyl, $(C_3-C_8)$cycloalkyl-$(C_1-C_4)$alkyl, $(C_1-C_{10})$heteroaryl-$(C_1-C_4)$alkyl or $(C_1-C_{10})$heterocyclic-$(C_1-C_4)$alkyl; wherein each of the aforesaid $(C_3-C_8)$cycloalky or $(C_1-C_{10})$heterocyclic may optionally contain one or two double bonds;

wherein A and B may be independently optionally substituted on any of the ring carbon atoms capable of forming an additional bond by one or two substituents independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy, and $(C_3-C_8)$cycloalkyloxy;

X is selected from the group consisting of oxygen, $>C=O$, sulfur, $>SO_2$, $>S=O$, $>NR^{10}$, —$CH_2O$—, —$OCH_2$—, —$CH_2S$—, —$CH_2(S=O)$—, —$CH_2SO_2$—, —$SCH_2$—, —$SOCH_2$—, —$SO_2$—$CH_2$ [$N(R^{10})$]—, —$[N(R^{10})]SO_2$— and —$SO_2[N(R^{10})]$—;

Y is selected from the group consisting of a bond, oxygen, sulfur, $>C=O$, $>SO_2$, $>S=O$, $>NR^{12}$, —$CH_2$—, —$CH_2O$—, —$OCH_2$—, —$CH_2S$—, —$CH_2(S=O)$—, —$CH_2SO_2$—, —$SCH_2$—, —$(S=O)CH_2$—, —$SO_2CH_2$—, —$[N(R^{12})]CH_2$—, —$CH_2[N(R^{12})]$—, —$CH_2CH_2$—, —$CH=CH$—, —$[N(R^{12})]$—$SO_2$— and —$SO_2[N(R^{12})]$—;

$R^1$ is hydrogen, $(R^2)_{2n+1}$—$(C)_n$— or $(C_3-C_8)$cycloalkyl wherein said $(C_3-C_8)$cycloalkyl may also optionally be substituted by one to two substituents independently selected from halo, $(C_1-C_4)$alkyl, $(C_1-C_4)$alkenyl, $(C_1-C_4)$alkynyl, $R^3$—, $R^3$—O—, perfluoro$(C_1-C_4)$alkoxy, $R^3$—$(C_1-C_4)$alkyl-O—, $R^3$—$(C=O)$—O—, $(R^3)_2N$—$(C=O)$—O—, —$NO_2$, $(R^3)_2N$—, $R^3$—$(C=O)$—$(NR^4)$—, $R^3$—$(SO_2)$—$(NR^4)$—, $R^3O$—$(C=O)$—$(NR^4)$—, $(R^3)_2$—$N$—$(C=O)$—$(NR^4)$—, $R^3$—$S$—, $R^3$—$(S=O)$—, $R^3$—$(SO_2)$—, $(R^3)_2N$—$(SO_2)$—, —$CN$, $R^3$—$(C=O)$—, $R^3$—$O$—$(C=O)$— and $(R^3)_2N$—$(C=O)$—;

n is an integer from one to ten;

each $R^2$ is independently selected from the group consisting of halo, $R^3$—, $(C_1-C_4)$alkenyl, $(C_1-C_4)$alkynyl, $R^3$—$O$—, perfluoro$(C_1-C_4)$alkoxy, $R^3$—$(C=O)$—$O$—, $(R^3)_2N$—$(C=O)$—$O$—, —$NO_2$, $(R^3)_2N$—, $R^3$—$(SO_2)$—$(NR^4)$—, $R^3$—$(C=O)$—$(NR^4)$—, $R^3O$—$(C=O)$—$(NR^4)$—, $(R^3)_2$—$N$—$(C=O)$—$(NR^4)$—, $R^3$—$S$—, $R^3$—$(S=O)$—, $R^3$—$(SO_2)$—, $(R^3)_2N$—$(SO_2)$—, —$CN$, $R^3$—$(C=O)$—, $R^3$—$O$—$(C=O)$— and $(R^3)_2N$—$(C=O)$—; wherein not more than three of said $R^2$ substituents may be other than hydrogen and any one carbon atom of said —$(C)_n$— group can contain only one bond to a heteroatom; wherein a carbon atom of any two $R^2$ groups may be taken together with the carbon atoms to which the $R^2$ groups are attached to form a four to ten membered ring;

each $R^3$ is independently selected from the group consisting of hydrogen, $(C_1-C_4)$alkyl, $(C_6-C_{10})$aryl, $(C_3-C_8)$cycloalkyl, $(C_1-C_{10})$heteroaryl and $(C_1-C_{10})$heterocyclyl; wherein eech $R^3$ may be optionally substituted on any carbon atom able to support an additional substituent, by one to three substituents per alkyl moiety or by one to three substituents per ring, independently selected from the group consisting of halo, hydroxy, amino, —$CN$, $(C_1-C_4)$alkyl, $(C_1-C_4)$alkoxy, $(C_1-C_4)$alkyl-$NH$—, $[(C_1-C_4)$alkyl$]_2$—$N$—, $(C_6-C_{10})$aryl, $(C_3-C_8)$cycloalkyl, $(C_1-C_{10})$heteroaryl and $(C_1-C_{10})$heterocyclyl; wherein said $(C_3-C_8)$cycloalkyl and $(C_1-C_{10})$heterocyclyl may also optionally be substituted by oxo; wherein said $(C_1-C_{10})$heteroaryl and $(C_1-C_{10})$heterocyclyl may optionally be substituted on any ring nitrogen atom able to support an additional substituent by one to two substituents per ring inde pendently selected from the group consisting of $(C_1-C_4)$alkyl, $(C_1-C_4)$alkyl-$(C=O)$—, $(C_6-C_{10})$aryl, $(C_3-C_8)$cycloalkyl, $(C_1-C_{10})$heteroaryl and $(C_1-C_{10})$heterocyclyl;

wherein said $R^3$ group may optionally be taken together with an $R^4$ group to form a three to eight membered ring; wherein two of said $R^4$ groups may be taken together to form a three to eight membered ring;

$R^4$ wherever it occurs is independently selected from hydrogen and $(C_1-C_4)$alkyl;

G is $R^5$— or $R^6$—$(CHR^{13})_p$—; wherein G is a substituent on any ring carbon atom of B capable of forming an additional bond and is oriented at a position other than alpha to the point of attachment of the B ring to Y;

p is an integer from one to six;

wherein $R^5$ is selected from the group consisting of $R^7$—, $R^{11}$—O—, $R^7$—$(C_1-C_4)$alkyl-O—, $R^8$—$(C=O)$—O—, $H_2N(C=O)$—O—, $R^8$—NH$(C=O)$—O—, $(R^8)_2N(C=O)$—O—, $R^8$—S—, $R^8$—$(S=O)$—, $R^8$—$(SO_2)$—, $H_2N$—$(SO_2)$—, $R^8$—NH—$(SO_2)$—, $(R^8)_2N$—$(SO_2)$—, formyl, $R^8$—$(C=O)$—, HO—$(C=O)$—, $R^8$—O—$(C=)$—, $H_2N$—$(C=O)$—, $R^8$NH—$(C=O)$—, $(R^8)_2N$—$(C=O)$—, —$NO_2$, $NH_2$, $R^8$—NH—, $(R^8)_2N$—, H$(C=O)$—$(NR^9)$—, $R^8$—$(C=O)$—$(NR^9)$—, $H_2N$—$(C=O)$—$(NR^9)$—, $R^8$NH—$(C=O)$—$(NR^9)$—, $(R^8)_2N$—$(C=O)$—$(NR^9)$—, $R^8$O—$(C=O)$—$(NR^9)$—, $R^8$—$(SO_2)$—NH— and $R^8$—$(SO_2)$—$(NR^9)$—;

$R^6$ is selected from the group consisting of perfluoro $(C_1-C_4)$alkyl, $(C_1-C_4)$alkenyl, $(C_1-C_4)$alkynyl, $R^7$, OH, $R^8$—O—, $R^8$—$(C_1-C_4)$alkyl-O—, perfluoro $(C_1-C_4)$alkoxy, $R^8$—$(C=O)$—O—, $H_2N(C=O)$—O—, $R^8$—NH$(C=O)$—O—, $(R^8)_2N(C=O)$—O—, $R^8$—S—, $R^8$—$(S=O)$—, $R^8$—$(SO_2)$—, $H_2N$—$(SO_2)$—, $R^8$—NH—$(SO_2)$—, $(R^8)_2N$—$(SO_2)$—, formyl, —CN, $R^8$—$(C=O)$—, HO—$(C=O)$—, $R^8$—O—$(C=O)$—, $H_2N$—$(C=O)$—, $R^8$NH—$(C=O)$—, $(R^8)_2N$—$(C=O)$—, —$NO_2$, $NH_2$, $R^8$—NH—, $(R^8)_2N$—, H$(C=O)$—$(NR^9)$—, $R^8$—$(C=O)$—$(NR^9)$—, $H_2N$—$(C=O)$—$(NR^9)$—, $R^8$NH—$(C=O)$—$(NR^9)$—, $(R^8)_2N$—$(C=O)$—$(NR^9)$—, $R^8$O—$(C=O)$—$(NR^9)$—, $R^8$—$(SO_2)$—NH— and $R^8$—$(SO_2)$—$(NR^9)$—;

$R^7$ is selected from the group consisting of $(C_6-C_{10})$aryl, $(C_3-C_8)$cycloalkyl, $(C_1-C_{10})$heteroaryl and $(C_1-C_{10})$heterocyclyl; wherein said $(C_6-C_{10})$aryl, $(C_3-C_8)$cycloalkyl, $(C_1-C_{10})$heteroaryl and $(C_1-C_{10})$heterocyclyl moieties may be optionally substituted on any of the ring carbon atoms capable of forming an additional bond by one to three substituents per ring independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy, amino, $(C_1-C_4)$alkyl-NH—, $[(C_1-C_4)$alkyl$]_2$-N— and $(C_3-C_8)$cycloalkyloxy; wherein said $(C_3-C_8)$cycloalkyl and $(C_1-C_{10})$heterocyclyl moieties may also optionally be substituted by oxo; wherein said $(C_1-C_{10})$heteroaryl and $(C_1-C_{10})$heterocyclyl moieties may optionally be substituted on any ring nitrogen atom able to support an additional substituent by one to two substituents per ring independently selected from the group consisting of $(C_1-C_4)$alkyl and $(C_1-C_4)$alkyl-$(C=O)$—;

$R^8$ is selected from the group consisting of $(C_1-C_4)$alkyl, $(C_6-C_{10})$aryl, $(C_3-C_8)$cycloalkyl, $(C_1-C_{10})$heteroaryl and $(C_1-C_{10})$heterocyclyl; wherein each $R^8$ may be optionally substituted on any carbon atom able to support an additional substituent, by one to three substituents per alkyl moiety or by one to three substituents per ring, independently selected from the group consisting of F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy, and $(C_3-C_8)$cycloalkyloxy; wherein said $(C_3-C_8)$cycloalkyl and $(C_1-C_{10})$heterocyclyl may also optionally be substituted by oxo; wherein said $(C_1-C_{10})$heteroaryl and $(C_1-C_{10})$heterocyclyl may also optionally be substituted on any ring nitrogen atom able to support an additional substituent by one to two substituents per ring independently selected from the group consisting of $(C_1-C_4)$alkyl and $(C_1-C_4)$alkyl-$(C=O)$—; wherein two of said $R^8$ may optionally be taken together with the heteroatom to which they are attached to form a three to eight membered ring;

$R^9$ wherever it occurs is independently selected from hydrogen and $(C_1-C_4)$alkyl; wherein said $R^8$ and $R^9$ may optionally be taken together with the heteroatoms to which they are attached to form a three to eight membered ring;

$R^{10}$ wherever it occurs is independently selected from hydrogen and $(C_1-C_4)$alkyl;

$R^8$ is selected from the group consisting of $(C_6-C_{10})$aryl, $(C_1-C_{10})$heteroaryl and $(C_1-C_{10})$heterocyclyl; wherein said $(C_6-C_{10})$aryl, $(C_1-C_{10})$heteroaryl and $(C_1-C_{10})$heterocyclyl moieties may be optionally substituted on any of the ring carbon atoms capable of forming an additional bond by one to three substituents per ring independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy, and $(C_3-C_8)$cycloalkyloxy; wherein said $(C_1-C_{10})$heterocyclyl may also optionally be substituted by oxo; wherein said $(C_1-C_{10})$heteroaryl and $(C_1-C_{10})$heterocyclyl may optionally be substituted on any ring nitrogen atom able to support an additional substituent by one to two substituents per ring independently selected from the group consisting of $(C_1-C_4)$alkyl and $(C_1-C_4)$alkyl-$(C=O)$—;

$R^{12}$ wherever it occurs is independently selected from hydrogen and $(C_1-C_4)$alkyl;

$R^{13}$ is independently selected from hydrogen and $(C_1-C_4)$alkyl; wherein $R^{13}$ may optionally be taken together with $R^6$ to form a four to 10 membered ring;

or the pharmaceutically acceptable salts thereof.

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

The invention also relates to base addition salts of formula I. The chemical bases that may be used as reagents to prepare pharmaceutically acceptable base salts of those compounds of formula I that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

The term "a bond", as used herein in the group Y, means that the groups $Ar^1$ and Z are directly connected through a carbon-carbon bond so as to form pendent aryl rings such as diphenyl.

The term "alkyl", as used herein, unless otherwise indicated, includes saturated monovalent hydrocarbon radicals having straight, branched or cyclic moieties or combinations thereof. Alkyl groups, wherever they occur, may be optionally substituted by a suitable substituent.

The term "alkenyl", as used herein, unless otherwise indicated, includes hydrocarbon radicals containing at least one olefin linkage and having straight, branched or cyclic moieties or combinations thereof.

The term "alkynyl", as used herein, unless otherwise indicated, includes hydrocarbon radicals containing at least one carbon-carbon triple bond linkage and having straight, branched or cyclic moieties or combinations thereof.

The term "alkoxy", as used herein, includes O-alkyl groups wherein "alkyl" is as defined above.

The term "halo", as used herein, unless otherwise indicated, includes fluorine, chlorine, bromine or iodine, preferably fluorine or chlorine.

The term "(C=O)" as used herein refers to a carbonyl group. Used in common with a nitrogen atom the group refers to amide. Used in common with an oxygen atom, the group refers to carboxylic acid derivatives.

The term "aryl", as used herein, unless otherwise indicated, includes an organic radical derived from an aromatic hydrocarbon by removal of one or more hydrogens, such as phenyl, naphthyl indanyl or tetrahydronaphthyl; optionally substituted by 1 to 3 suitable substituents such as fluoro, chloro, cyano, nitro, trifluoromethyl, $(C_1-C_6)$alkoxy, $(C_6-C_{10})$aryloxy, $(C_3-C_8)$cycloalkyloxy, trifluoromethoxy, difluoromethoxy, or $(C_1-C_6)$alkyl.

The term "cycloalkyl", as used herein, unless otherwise indicated, includes a mono or bicyclic carbocyclic ring (e.g., cyclopropyl, cyclobutyl, cyclopentyl, cyclohexyl, cycloheptyl, cyclooctyl, cyclononyl, cyclopentenyl, cyclohexenyl, bicyclo[2.2.1]heptanyl, bicyclo[3.2.1]octanyl and bicyclo[5.2.0]nonanyl, etc.); optionally containing 1–2 double bonds and optionally substituted by 1 to 3 suitable substituents as defined below such as fluoro, chloro, trifluoromethyl, $(C_1-C_4)$alkoxy, $(C_6-C_{10})$aryloxy, trifluoromethoxy, difluoromethoxy or $(C_1-C_4)$alkyl, more preferably fluoro, chloro, methyl, ethyl and methoxy.

The term "heteroaryl", as used herein, unless otherwise indicated, includes an organic radical derived from an aromatic heterocyclic compound by removal of one or more hydrogens, such as benzimidazolyl, benzofuranyl, benzofurazanyl, 2H-1-benzopyranyl, benzothiadiazine, benzothiazinyl, benzothiazolyl, benzothiophenyl, benzoxazolyl, chromanyl, cinnolinyl, furazanyl, furopyridinyl, furyl, imidazolyl, indazolyl, indolinyl, indolizinyl, indolyl, 3H-indolyl, isoindolyl, isoquinolinyl, isothiazolyl, isoxazolyl, naphthyridinyl, oxadiazolyl, oxazolyi, phthalazinyl, pteridinyl, purinyl, pyrazinyl, pyridazinyl, pyridinyl, pyrimidinyl, pyrazolyl, pyrrolyl, quinazolinyl, quinolinyl, quinoxalinyl, tetrazolyl, thiazolyl, thiadiazolyl, thienyl, triazinyl, and triazolyl, wherein said $(C_1-C_{10})$heteroaryl is optionally substituted on any of the ring carbon atoms capable of forming an additional bond by one or two suitable substituents such as F, Cl, Br, CN, OH, $(C_1-C_4)$alkyl, $(C_1-C_4)$perfluoroalkyl, $(C_1-C_4)$ perfluoroalkoxy, $(C_1-C_4)$alkoxy, and $(C_3-C_8)$cycloalkyloxy. The foregoing groups, as derived from the compounds listed above, can be C-attached or N-attached where such is possible. For instance, a group derived from pyrrole can be pyrrol-1-yl (N-attached) or pyrrol-3-yl (C-attached).

The term "heterocyclyl", as used herein, unless otherwise indicated, includes an organic radical derived from a non-aromatic heterocyclic compound by removal of one or more hydrogens, such as 3-azabicyclo[3.1.0]hexanyl, 3-azabicyclo[4.1.0]-heptanyl, azetidinyl, dihydrofuranyl, dihydropyranyl, dihydrothienyl, dioxanyl, 1,3-dioxolanyl, 1,4-dithianyl, hexahydroazepinyl, hexahydropyrimidine, imidazolidinyl, imidazolinyl, isoxazolidinyl, morpholinyl, oxazolidinyl, piperazinyl, piperidinyl, 2H-pyranyl, 4H-pyranyl, pyrazolidinyl, pyrazolinyl, pyrrolidinyl, 2-pyrrolinyl, 3-pyrrolinyl, quinolizinyl, tetrahydrofuranyl, tetrahydropyranyl, 1,2,3,6-tetrahydropyridinyl, tetrahydrothienyl, tetrahydrothiopyranyl, thiomorpholinyl, thioxanyl, and trithianyl. The foregoing groups, as derived from the compounds listed above, can be C-attached or N-attached where such is possible. For example, a group derived from piperidine can be piperidin-1-yl (N-attached) or piperidin-4-yl (C-attached). The foregoing groups, as derived from the compounds listed above, can be optionally substituted where such is possible by a suitable substituent, such as oxo F, Cl, Br, CN, OH, $(C_1-C_4)$alkyl, $(C_1-C_4)$ perfluoroalkyl, $(C_1-C_4)$perfluoroalkoxy, $(C_1-C_4)$alkoxy, and $(C_3-C_8)$cycloalkyloxy.

"A suitable substituent" is intended to mean a chemically and pharmaceutically acceptable functional group i.e., a moiety that does not negate the inhibitory activity of the inventive compounds. Such suitable substituents may be routinely selected by those skilled in the art. Illustrative examples of suitable substituents include, but are not limited to halo groups, perfluoroalkyl groups, perfluoroalkoxy groups, alkyl groups, hydroxy groups, oxo groups, mercapto groups, alkylthio groups, alkoxy groups, aryl or heteroaryl groups, aryloxy or heteroaryloxy groups, aralkyl or heteroaralkyl groups, aralkoxy or heteroaralkoxy groups, carboxy groups, amino groups, alkyl- and dialkylamino groups, carbamoyl groups, alkylcarbonyl groups, alkoxycarbonyl groups, alkylaminocarbonyl groups dialkylamino carbonyl groups, arylcarbonyl groups, aryloxycarbonyl groups, alkylsulfonyl groups, an arylsulfonyl groups and the like.

The phrase "capable of forming an additional bond" refers to the replacement of a hydrogen radical with another higher radical.

The phrase "oriented at a position other than alpha to the point of attachment of the B ring to Y" refers to substitution at the position adjacent to the bridgehead atom connecting to the Y group. If B is phenyl then substitution of the identified group can not be in the ortho position (i.e. relative to the connection of phenyl to Y).

Some compounds of formula I contain chiral centers and therefore exist in different enantiomeric forms. This invention relates to all optical isomers, enantiomers, diasteriomers and stereoisomers of the compounds of formula I and mixtures thereof. The compounds of the invention also exist in different tautomeric forms. This invention relates to all tautomers of formula I. Those skilled in the art are well aware that the pyrimidine-2,4,6-trione nucleus exists as a mixture of tautomers in solution. The various ratios of the tautomers in solid and liquid form is dependent on the various substituents on the molecule as well as the particular crystallization technique used to isolate a compound.

An embodiment of the invention includes those compounds of formula I wherein X is >C=O more preferably wherein Y is a bond, oxygen, sulfur, —CH$_2$—, >SO$_2$, —OCH$_2$— or —CH$_2$O—, more preferably wherein Y is oxygen, —OCH$_2$— or —CH$_2$O—, most preferably wherein Y is oxygen.

Preferred compounds of the invention include those wherein X is oxygen, —OCH$_2$—, —CH$_2$O—, more preferably wherein X is oxygen; more preferably wherein Y is a bond, oxygen, sulfur, —CH$_2$—, >SO$_2$, —OCH$_2$— or —CH$_2$O—, more preferably wherein Y is oxygen, —OCH$_2$— or —CH$_2$O—, most preferably wherein Y is oxygen.

Other embodiments of the invention include those compounds of formula I wherein X is sulfur, >SO$_2$, >S=O, —SCH$_2$—, —CH$_2$S—, —(O=S)CH$_2$—, —CH$_2$(S=O)—, —CH$_2$SO$_2$— or —SO$_2$CH$_2$—, more preferably wherein Y is a bond, oxygen, sulfur, —CH$_2$—, >SO$_2$, —OCH$_2$— or —CH$_2$O—, more preferably wherein Y is oxygen, —OCH$_2$— or —CH$_2$O—, most preferably wherein Y is oxygen.

Other embodiments of the invention include those compounds of formula I wherein X is >NR$^{10}$, —CH$_2$N(R$^{10}$)— or —N(R$^{10}$)CH$_2$—, more preferably wherein Y is a bond, oxygen, sulfur, —CH$_2$—, >SO$_2$, —OCH$_2$— or —CH$_2$O—, more preferably wherein Y is oxygen, —OCH$_2$— or —CH$_2$O—, most preferably wherein Y is oxygen.

Other embodiments of the invention include those compounds of formula I wherein X is —N(R$^{10}$)SO$_2$— or —SO$_2$N(R$^{11}$)—, more preferably wherein Y is a bond, oxygen, sulfur, —CH$_2$—, >SO$_2$, —OCH$_2$— or —CH$_2$O—, more preferably wherein Y is oxygen, —OCH$_2$—, most preferably wherein Y is oxygen.

Other preferred compounds are those wherein A is optionally substituted phenyl.

Other embodiments of the present invention include those compounds wherein A is (C$_1$–C$_{10}$)heteroaryl; preferably pyridyl, furyl, pyrroyl, thienyl, isothiazolyl, imidazolyl, benzimidazolyl, tetrazolyl, pyrazinyl, pyrimidyl, quinolyl, isoquinolyl, benzofuryl, isobenzofuryl, benzothienyl, pyrazolyl, indolyl, isoindolyl, purinyl, carbazolyl, isoxazolyl, thiazolyl, oxazolyl, benzthiazolyl or benzoxazolyl, more preferably pyridyl, pyridazinyl, pyrazinyl, pyrimidyl, most preferably pyridyl optionally substituted by 1 to 3 suitable substituents, such as fluoro, chloro, trifluoromethyl, (C$_1$–C$_6$)alkoxy, (C$_6$–C$_{10}$)aryloxy, trifluoromethoxy, difluoromethoxy or (C$_1$–C$_6$)alkyl.

Other preferred compounds are those wherein B is optionally substituted phenyl.

Other embodiments of the invention include those compounds of formula I wherein B is (C$_1$–C$_{10}$)heteroaryl (C$_1$–C$_4$)alkyl or (C$_1$–C$_{10}$)heteroaryl, preferably (C$_1$–C$_{10}$) heteroaryl; wherein said (C$_1$–C$_{10}$)heteroaryl is optionally substituted with one or more substituents, preferably zero, one or two substituents, independently selected from F, Cl, Br, —CN, OH, (C$_1$–C$_4$)alkyl, (C$_1$–C$_4$)perfluoroalkyl, (C$_1$–C$_4$)perfluoroalkoxy, (C$_1$–C$_4$)alkoxy and (C$_3$–C$_8$) cycloalkyloxy.

Other embodiments of the invention include those compounds of formula I wherein B is a (C$_1$–C$_{10}$)heterocyclyl group such as tetrahydrofuranyl, tetrahydropyranyl, N-methyl-3-azetidinyl, piperazinyl, piperidinyl, 1,3-oxazolidin-4-on-5-yl, 1,3-oxazolidin-2,4-dion-5-yl, 4,5-dihydro-1,2-oxazolidin-3-on-4-yl, 1,3-thiazolidin-4-on-5-yl, 1,3-thiazolidin-2,4-dion-5-yl, 1,3-imidazolidin-4-on-5-yl, 1,3-imidazolidin-2,4-dion-5-yl, 1,2-pyrazolidin-3-on-4-yl, tetrahydro-1,3-oxazin-4-on-5-yl, tetrahydro-1,3-oxazin-2,4-dion-5-yl, morpholinyl, morpholin-3-on-2-yl, morpholin-3,5-dion-2-yl, 2,3-dihydro-1,4-oxazin-3-on-2-yl, tetrahydro-1,3-thiazin-4-on-5-yl, tetrahydro-1,3-thiazin-2,4-dion-5-yl, thiomorpholinyl, thiomorpholin-3-on-2-yl, thiomorpholin-3,5-dion-2-yl, 2,3-dihydro-1,4-thiazin-3-on-2-yl, hexahydro-1,2-diazin-3-on-4-yl, 4,5-dihydro-2H-pyridazin-3-on-4-yl, hexahydro-1,3-diazin-2,4-dion-5-yl, piperazin-2-on-3-yl, piperazin-2,6-dion-3-yl, tetrahydro-1,3,4-thiadiazin-5-on-6-yl, 5,6-dihydro-1,3,4-thiadiazin-5-on-6-yl, 1,3,4-oxadiazin-5-on-6-yl, 5,6-dihydro-1,2,4-oxadiazin-5-on-6-yl, tetrahydro-1,2,4-oxadiazin-5-on-6-yl, 1,2,4-triazin-5-on-6-yl, tetrahydro-1,2,4-oxadiazin-5-on-6-yl, 5,6-dihydro-1-2,4-oxadiazin-5-on-6-yl, 1,2,4-oxadiazin-3,5-dion-6-yl, and 1,2,4-triazin-6-on-5-yl; preferably tetrahydrofuranyl, tetrahydropyranyl, N-methyl-3-azetidinyl, piperazinyl, piperidinyl, N-methylpiperidinyl and morpholinyl; more preferably tetrahydrofuranyl and tetrahydropyranyl; most preferably tetrahydrofuran-2-yl and tetrahydropyran-2-yl. One skilled in the art will appreciate that the numbering scheme used throughout this specification is in accordance with standard nomenclature practice beginning numbering at the heaviest atom.

Other embodiments of the invention include those compounds of formula I wherein B is (C$_3$–C$_{10}$)cycloalkyl group such as cyclopropyl, cyclobutyl, cyclopentyl, cyclohexyl or cycloheptyl; preferably cyclohexyl or cycloheptyl.

Other embodiments of the invention include those compounds of formula I wherein G is R$^5$— wherein R$^5$ is H$_2$N—(C=O)—, R$^8$NH—(C=O)—, (R$^8$)$_2$N—(C=O)—, NH$_2$, R$^8$—NH—, (R$^8$)$_2$N—, R$^8$—(C=O)—(NR$^9$)—, H$_2$N—(C=O)—(NR$^9$)—, R NH—(C=O)—(NR$^9$)—, (R$^8$)$_2$ N—(C=O)—(NR$^9$)—, R$^8$O—(C=O)—(NR$^9$)—, R$^8$—(SO$_2$)—NH—, R$^8$—(SO$_2$)—(NR$^9$)—, R$^8$—(SO$_2$)—, and H$_2$N—(SO$_2$)—; preferably H$_2$N—(C=O)—, R$^8$NH—(C=O)—, (R$^8$)$_2$N—(C=O)—, NH$_2$, R$^8$—NH—, (R$^8$)$_2$N—, and R$^8$—(C=O)—(NR$^9$)—, more preferably wherein R$^8$ is (C$_1$–C$_4$)alkyl (preferably methyl).

Other preferred compounds of the invention wherein G is R$^5$—, wherein R$^5$ contains an R$^8$ group, are those wherein R$^8$ is (C$_1$–C$_4$)alkyl or (C$_3$–C$_8$)cycloalkyl optionally substituted on any of the ring carbon atoms capable of forming an additional bond by one to three substituents per ring independently selected from F, Cl, Br, CN, OH, (C$_1$–C$_4$)alkyl, (C$_1$–C$_4$)perfluoroalkyl, (C$_1$–C$_4$)perfluoroalkoxy, (C$_1$–C$_4$) alkoxy, and (C$_3$–C$_8$)cycloalkyloxy; preferably (C$_1$–C$_4$)alkyl and (C$_1$–C$_4$)alkoxy.

Preferred compounds of the invention include those compounds wherein G is R$^5$—, wherein R$^5$— is H$_2$N—(C=O)—, R$^8$NH—(C=O)—, (R$^8$)$_2$N—(C=O)— or R$^8$—(C=O)—(NR$^9$)—. More preferred compounds of the invention include those compounds of the invention wherein G is R$^5$—, wherein R$^5$— is R$^8$NH—(C=O)— or (R$^8$)$_2$N—(C=O)—. Most preferred compounds wherein G is R$^5$—, wherein R$^5$— contains R$_8$, are those compounds wherein R$^8$ is methyl.

Most preferred embodiments of the invention include those compounds of formula I wherein G is R$^5$— wherein R$^5$ is R$^7$— or R$^7$—(C$_1$–C$_4$)alkyl-O—; wherein R$^7$ is preferably (C$_6$–C$_{10}$)aryl, (C$_3$–C$_{10}$)cycloalkyl or (C$_1$–C$_{10}$)heteroaryl; optionally substituted on any of the ring carbon atoms capable of forming an additional bond by one to three substituents per ring independently selected from F, Cl, Br, CN, OH, (C$_1$–C$_4$)alkyl, (C$_1$–C$_4$)perfluoroalkyl, (C$_1$–C$_4$) perfluoroalkoxy, (C$_1$–C$_4$)alkoxy, amino, (C$_1$–C$_4$)alkyl-NH—, [(C$_1$–C$_4$)alkyl]$_2$-N— and (C$_3$–C$_8$)cycloalkyloxy. More preferred embodiments of the invention include those compounds of formula I wherein G is R$^5$—, wherein R$^5$ is R$^7$—, wherein R$^7$ is (C$_1$–C$_{10}$)heteroaryl.

Another embodiment of the invention of interest to the inventors are those compounds wherein G is R$^5$—, wherein R$^5$ is R$^7$—, wherein R$^7$ is (C$_6$–C$_{10}$)aryl, more preferably phenyl.

Embodiments of the invention wherein G is —$R^5$, wherein $R^5$ is $R^7$— or $R^7$—($C_1$–$C_4$)alkyl-O—; include those compounds wherein $R^7$ is ($C_1$–$C_{10}$)heteroaryl selected from the group consisting of pyridyl, furyl, pyrroyl, thienyl, isothiazolyl, imidazolyl, benzimidazolyl, tetrazolyl, pyrazinyl, pyrimidyl, quinolyl, isoquinolyl, benzofuryl, isobenzofuryl, benzothienyl, pyrazolyl, indolyl, isoindolyl, purinyl, carbazolyl, isoxazolyl, thiazolyl, oxazolyl, benzthiazolyl or benzoxazolyl, more preferably pyridyl, pyrimidyl, triazole, diazole, oxazole, oxadiazole, pyrrole or thiazole; wherein each of said ($C_1$–$C_{10}$)heteroaryl may optionally be substituted by 1 to 3 suitable substituents, such as fluoro, chloro, trifluoromethyl, ($C_1$–$C_6$)alkoxy, ($C_6$–$C_{10}$) aryloxy, trifluoromethoxy, difluoromethoxy and ($C_1$–$C_6$) alkyl.

Preferred ($C_1$–$C_{10}$)heteroaryl includes five membered heteroaryls such as triazoles, diazoles, oxazoles, oxadiazoles, pyrroles and thiazoles; preferably 1,2,4-triazol-1-yl, 1,2,4-triazol-3-yl, 1,3,4-triazol-1-yl, 1,3-diazol-1-yl, 1,2-diazol-3-yl, 1,2-diazol-1-yl, 1,2-diazol-4-yl, 1,3-oxazol-4-yl, 1,3-oxazol-5-yl, 1,2-oxazol-5-yl, 1,2,4-oxadiazol-3-yl, 1,3,4-oxadiazol-2-yl, pyrrol-1-yl, 1,3-thiazol-4-yl and 1,3-thiazol-2-yl; optionally substituted with ($C_1$–$C_4$)alkyl, amino, ($C_1$–$C_4$)alkyl-NH—, [($C_1$–$C_4$)alkyl]$_2$-N—, halo or hydroxy, preferably with ($C_1$–$C_4$)alkyl, more preferably methyl. Most preferred ($C_1$–$C_{10}$)heteroaryl includes 1,3,4-oxadiazolyl optionally substituted with ($C_1$–$C_4$)alkyl.

Other embodiments of the invention include those compounds of formula I wherein G is —$R^5$, wherein $R^5$ is $R^8$—O— or $R^8$—(C=O)—O—. Other compounds of interest to the present inventors include those compounds wherein $R^5$ contains $R^{11}$, wherein $R^{11}$ is ($C_6$–$C_{10}$)aryl or ($C_1$–$C_{10}$)heteroaryl optionally substituted on any of the ring carbon atoms capable of forming an additional bond by one to three substituents independently selected from F, Cl, Br, CN, OH, ($C_1$–$C_4$)alkyl, ($C_1$–$C_4$)perfluoroalkyl, ($C_1$–$C_4$) perfluoroalkoxy, ($C_1$–$C_4$)alkoxy and ($C_3$–$C_8$)cycloalkyloxy; preferably CN, ($C_1$–$C_4$)alkyl, amino, ($C_1$–$C_4$)alkyl-NH— and [($C_1$–$C_4$)alkyl]$_2$-N—.

Other embodiments of the invention include those compounds of formula I wherein G is —$R^5$ wherein $R^5$ is $R^8$—O—(C=O)— or $R^8$—(C=O)—.

Other embodiments of the invention include those compounds of formula I wherein G is —$R^5$ wherein $R^5$ is $R^8$—S—, $R^8$—(S=O)—, $R^8$—($SO_2$)—, $R^8$—NH—($SO_2$)— or $(R^8)_2$N—($SO_2$)—.

Other preferred embodiments of the invention include those compounds of formula I wherein G is $R^6$—(CHR$^{13}$)$_p$—, preferably wherein p is an integer from one to six; are those wherein $R^6$ is selected from the group consisting of ($C_1$–$C_4$)alkenyl, ($C_1$–$C_4$)alkynyl, —CN, —$NO_2$, OH, $NH_2$, perfluoro($C_1$–$C_4$)alkoxy, $H_2$N—($SO_2$)—, $H_2$N—(C=O)—, $R^8$—NH—(C=O)—, $(R^8)_2$—(C=)— and $NH_2$—(C=O)—(NR$^9$)—; preferably wherein $R^6$ is —CN, OH, $NH_2$, $H_2$N—(C=O)— or $NH_2$—(C=O)—(NR$^9$)—; most preferably wherein $R^6$ is $H_2$N—(C=O)— or —CN.

Other preferred embodiments of the invention include those compounds of formula I wherein G is $R^6$—(CHR$^{13}$)$_p$—, preferably wherein p is an integer from one to six; are those wherein $R^6$ is selected from the group consisting of ($C_6$–$C_{10}$)aryl, ($C_3$–$C_8$)cycloalkyl, ($C_1$–$C_{10}$) heteroaryl and ($C_1$–$C_{10}$)heterocyclyl. More preferred compounds of the invention are those wherein $R^6$ is ($C_1$–$C_{10}$) heteroaryl optionally substituted with zero to three substituents independently selected from halo or ($C_1$–$C_4$) alkyl.

Other preferred embodiments of the invention include those compounds of formula I wherein G is $R^6$—(CHR$^{13}$)$_p$—, preferably wherein p is an integer from one to six; are those wherein $R^6$ contains an $R^8$ group such as $R^8$—O—, $R^8$—($C_1$–$C_4$)alkyl-O—, $R^8$—NH—, $(R^8)_2$N— $R^8$—S—, $R^8$(S=O)—, $R^8$—($SO_2$)—, $R^8$—($SO_2$)—NH—, $R^8$—($SO_2$)—(NR$^9$)—, $R^8$—NH—($SO_2$)—, $R^8$NH—(C=O)—(NR$^9$)—, $(R^8)_2$N—(C=O)—(NR$^9$)—, $R^8$O—(C=O)—(NR$^9$)—, $R^8$—O—(C=O)— and $R^8$—(C=O)—. More preferred compounds of the invention are those wherein $R^8$ is —($C_1$–$C_4$)alkyl or ($C_3$–$C_6$)cycloalkyl optionally substituted with one to three substituents independently selected from halo or ($C_1$–$C_4$)alkoxy.

Other compounds of interest within the scope of the invention include those compounds wherein G is $R^6$—(CHR$^{13}$)$_p$—, and $R^6$ contains an $R^8$ group are those wherein $R^8$is ($C_1$–$C_{10}$)heteroaryl, ($C_6$–$C_{10}$)aryl or ($C_1$–$C_{10}$) heterocyclyl, optionally substituted on any of the ring carbon atoms capable of forming an additional bond by one to three substituents independently selected from F, Cl, Br, CN, OH, ($C_1$–$C_4$)alkyl, ($C_1$–$C_4$)perfluoroalkyl, ($C_1$–$C_4$) perfluoroalkoxy, ($C_{C4}$)alkoxy, and ($C_3$–$C_8$)cycloalkyloxy; preferably ($C_1$–$C_4$)alkyl and ($C_1$–$C_4$)alkoxy.

Most preferred $R^6$ substituents containing an $R^8$ group are $R^8$NH—(C=O)—(NR$^9$)—, $(R^8)_2$NH—(C=O)—(NR$^9$)—, $R^8$O—(C=O)—(NR$^9$)— and $R^8$—(C=O)—(NR$^9$) ($C_1$–$C_4$)alkyl, more preferably methyl.

Other embodiments of the present invention include those wherein A and B are substituted on any of the ring carbon atoms capable of forming an additional bond by one or more substituents independently selected from F, Cl, Br, —CN, OH, ($C_1$–$C_4$)alkyl, ($C_1$–$C_4$)perfluoroalkyl, ($C_1$–$C_4$) perfluoroalkoxy, ($C_1$–$C_4$)alkoxy and ($C_3$–$C_8$)cycloalkyloxy.

Other embodiments of the invention include those compounds of formula I wherein $R^1$ is ($C_3$–$C_8$)cycloalkyl wherein said ($C_3$–$C_8$)cycloalkyl may also optionally be substituted by one to two substituents independently selected from halo, ($C_1$–$C_4$)alkyl, ($C_1$–$C_4$)alkenyl, ($C_1$–$C_4$) alkynyl, $R^3R^3$—O—, perfluoro($C_1$–$C_4$)alkoxy, $R^3$— ($C_1$–$C_4$)alkyl-O—, $R^3$—(C=O)—O—, —NO $R^3$—S—, $R^3$—(S=O)—, $R^3$—($SO_2$)—, $R^3$—($SO_2$)—(NR$^4$)—, $R^3$—NH—$R^3$—O—(C=O)— and $(R^3)_2$N—(C=O)—.

Other embodiments of the invention include those compounds of formula I wherein $R^1$ is $(R^2)_{2n+1}$—$(C)_n$— and n is an integer from one to ten; each $R^2$ is independently selected from the group consisting of halo, $R^3$—, ($C_1$–$C_4$) alkenyl, ($C_1C_4$)alkynyl, $R^3$—O—, perfluoro($C_1$–$C_4R^3$— (C=O)—O—, $(R^3)_2$N—(C=O)—O—, —$NO_2$, $(R^3)_2$N—, $R^3$—($SO_2$) (NR$^4$)—, $(R^3)_2$—N—(C=O)—(NR$^4$)—, $R^3$—S—, $R^3$—(S=O)—, $R^3$—(SO (C=O)— and $(R^3)_2$N—(C=O)—; wherein not more than three of said $R^2$ substituents may be other than hydrogen and any one carbon atom of said —$(C)_n$— group can contain only one bond to a heteroatom; and each $R^3$ is independently selected from the group consisting of hydrogen, ($C_1$–$C_4$)alkyl, ($C_6$–$C_{10}$) aryl, ($C_3$–$C_8$)cycloalkyl, ($C_1$–$C_{10}$)heteroaryl and ($C_1$–$C_1$wherein each $R^3$ may be optionally substituted by one to three substituents independently selected from the group consisting of halo, hydroxy, amino, —CN, ($C_1$–$C_4$) alkyl, ($C_1$–$C_4$)alkoxy, ($C_1$–$C_4$)alkyl-NH—, [($C_1$–$C_4$) alkyl]$_2$—N— ($C_6$–$C_{10}$)aryl, ($C_3$–$C_8$)cycloalkyl, ($C_1$–$C_{10}$) heteroaryl and ($C_1$–$C_{10}$)heterocyclyl; wherein said $R^3$ group may optionally be taken together with $R^4$ to form a three to eight membered ring.

Other embodiments of the invention include those compounds of formula I wherein $R^1$ is $(R^2)_{2n+1}$—$(C)_n$—, n is an integer from one to ten; at least one $R^2$ is independently selected from the group consisting of $R^3$—, $R^3$—O—, $R^3$—(C=O)—O—, $R^3$—S—, $R^3$—(S=O)—, $R^3R^3$—

$(SO_2)$—$(NR^4)$—, $R^3$—NH—$(SO_2)$—, $(R^3)_2N$—$(SO_2)$—, $R^3$—(C=O)—and each $R^3$ is independently selected from the group consisting of hydrogen and $(C_1-C_4)$alkyl; wherein each $R^3$ $(C_1-C_4)$alkyl moiety may be optionally substituted by one to three substituents independently selected from the group consisting of halo, hydroxy, amino, —CN, $(C_1-C_4)$alkyl, $(C_1-C_4)$alkoxy, $(C_1-C_4)$alkyl-NH—, $[(C_1-C_4)$alkyl$]_2$—N—$(C_6-C_{10})$aryl, $(C_3-C_8)$cycloalkyl, $(C_1-C_{10})$heteroaryl and $(C_1-C_{10})$heterocyclyl; wherein said $R^3$ group may optionally be taken together with $R^4$ to form a three to eight membered ring.

Other embodiments of the invention include those compounds of formula I wherein $R^1$ is $(R^2)_{2n+1}$—$(C)_n$—, n is an integer from one to ten; and each $R^2$ is independently selected from the group consisting of hydrogen, halo, $(C_1-C_4)$alkyl, $R^3$— and $R^3$—O—.

Other embodiments of the invention include those compounds of formula I wherein n is one to three; and each $R^3$ is independently selected from the group consisting of hydrogen and $(C_1-C_4)$alkyl; wherein each $R^3$ $(C_1-C_4)$alkyl moiety may be optionally substituted by one to three substituents independently selected from the group consisting of halo, hydroxy, amino, —CN, $(C_1-C_4)$alkyl, $(C_1-C_4)$alkoxy, $(C_1-C_4)$alkyl-NH—, $[(C_1-C_4)$alkyl$]_2$—N—$(C_6-C_{10})$aryl, $(C_3-C_8)$cycloalkyl, $(C_1-C_{10})$heteroaryl and $(C_1-C_{10})$heterocyclyl.

Other embodiments of the invention include those compounds of formula I wherein n is one to three; and each $R^3$ is independently selected from the group consisting of hydrogen and $(C_1-C_4)$alkyl; wherein at least one $R^3$ $(C_1-C_4)$alkyl group is substituted by halo, hydroxy, amino, —CN, $(C_1-C_4)$alkyl, $(C_1-C_4)$alkoxy, $(C_1-C_4)$alkyl-NH—, $[(C_1-C_4)$alkyl]—$C_8)$cycloalkyl, $(C_1-C_{10})$heteroaryl and $(C_1-C_{10})$heterocyclyl.

Other embodiments of the invention include those compounds of formula I wherein n is one; and each $R^3$ is independently selected from the group consisting of hydrogen and $(C_1-C_4)$alkyl; wherein at least one $R^3$ $(C_1-C_4)$alkyl group is substituted by $(C_1-C_4)$alkoxy, $(C_1-C_4)$alkyl-NH—, or $[(C_1-C_4)$alkyl$]_2$—N—.

Other embodiments of the invention include those compounds of formula I wherein at least one of said $R^3$ groups is $(C_6-C_{10})$aryl, $(C_3-C_8)$cycloalkyl, $(C_1-C_{10})$heteroaryl or $(C_1-C_{10})$heterocyclyl; wherein each of said $R^3$ groups may be optionally substituted by one to three substituents independently selected from the group consisting of halo, hydroxy, amino, —CN, $(C_1-C_4)$alkyl, $(C_1-C_4)$alkoxy, $(C_1-C_4)$alkyl-NH—, $[(C_1-C_4)$alkyl$]_2$—N— $(C_1-C_{10})$heteroaryl and $(C_1-C_{10})$heterocyclyl.

More preferred $R^1$ is $(C_1-C_4)$alkoxy$(C_1-C_4)$alkyl, most preferably ethoxyethyl.

More preferred compounds of the invention include compounds of formula 1, wherein X is oxygen, Y is a bond, oxygen, sulfur, —$CH_2$—, >$SO_2$, —$OCH_2$— or —$CH_2O$—; $R^1$ is $(R^2)_{2n+1}$—$(C)_n$—, n is one; and each $R^2$ is independently selected from the group consisting of hydrogen and $(C_1-C_4)$alkyl; wherein at least one $R^3$ $(C_1-C_4)$alkyl group is substituted by $(C_1-C_4)$alkoxy, $(C_1-C_4)$alkyl-NH— or $[(C_1-C_4)$alkyl$]_2$—N—.

Most preferred compounds of the invention include those wherein X is oxygen; Y is oxygen; A and B are each independently optionally substituted phenyl; G is optionally substituted phenyl and $R^1$ is $(R^2)_{2n+1}$—$(C)_n$—, n is one; each $R^2$ is independently selected from the group consisting of hydrogen, $(C_1-C_4)$alkyl, $R^3$— and $R^3$—O— and each $R^3$ is independently selected from the group consisting of hydrogen and $(C_1-C_4)$alkyl; wherein one $R^3$ $(C_1-C_4)$alkyl group is substituted by $(C_1-C_4)$alkoxy.

Other most preferred compounds of the invention include those wherein X is oxygen; Y is oxygen; and A and B are each optionally substituted phenyl; G is optionally substituted $(C_1-C_{10})$heteroaryl and $R^1$ is $(R^2)_{2n+1}$—$(C)_n$—, n is one; each $R^2$ is independently selected from the group consisting of hydrogen, $(C_1-C_4)$alkyl, $R^3$— and $R^3$—O— and each $R^3$ is independently selected from the group consisting of hydrogen and $(C_1-C_4)$alkyl; wherein one $R^3$ $(C_1-C_4)$alkyl group is substituted by $(C_1-C_4)$alkoxy.

Other more preferred compounds of the invention include those wherein X is oxygen; Y is oxygen; and A and B are each optionally substituted phenyl; G is optionally substituted $(C_3-C_8)$cycloalkyl and $R^1$ is $(R^2)_{2n+1}$—$(C)_n$—, n is one; each $R^2$ is independently selected from the group consisting of hydrogen, $(C_1-C_4)$alkyl, $R^3$— and $R^3$—O— and each $R^3$ is independently selected from the group consisting of hydrogen and $(C_1-C_4)$alkyl; wherein one $R^3$ $(C_1-C_4)$alkyl group is substituted by $(C_1-C_4)$alkoxy.

Most preferred compounds of the invention include those wherein X is oxygen; Y is oxygen; and A and B are each optionally substituted phenyl; G is $R^6$—$(CHR^9)_p$— and $R^1$ is $(R^2)_{2n+1}$—$(C)_n$—, n is one; each $R^2$ is independently selected from the group consisting of hydrogen, $(C_1-C_4)$alkyl, $R^3$— and $R^3$—O— and each $R^3$ is independently selected from the group consisting of hydrogen and $(C_1-C_4)$alkyl; wherein one $R^3$ $(C_1-C_4)$alkyl group is substituted by $(C_1-C_4)$alkoxy.

Specific preferred compounds of formula I are selected from the group consisting of:
  5-(2-Ethoxy-ethyl)-5-[4-(4-thiazol-2-yl-phenoxy)-phenoxy]-pyrimidine-2,4,6-trione;
  5-(2-Ethoxy-ethyl)-5-{4-[4-(2-methyl-2H-pyrazol-3-yl)-phenoxy]-phenoxy}-pyrimidine-2,4,6-trione;
  5-(2-Ethoxy-ethyl)-5-{4-[4-(1-methyl-1H-pyrazol-3-yl)-phenoxy]-phenoxy}-pyrimidine-2,4,6-trione;
  5-(4-{4-[5-(2-Ethoxy-ethyl)-2,4,6-trioxo-hexahydro-pyrimidin-5-yloxy]-phenoxy}-phenyl)-pentanenitrile;
  5-(2-Ethoxy-ethyl)-5-{4-[4-(2-methyl-thiazol-4-yl)-phenoxy]-phenoxy}-pyrimidine-2,4,6-trione;
  5-(2-Ethoxy-ethyl)-5-{4-[4-(1H-pyrazol-3-yl)-phenoxy]-phenoxy}-pyrimidine-2,4,6-trione;
  5-(2-Ethoxy-ethyl)-5-[4-(4-oxazol-5-yl-phenoxy)-phenoxy]-pyrimidine-2,4,6-trione; and
  5-(2-Ethoxy-ethyl)-5-[4-(4-pyrimidin-4-yl-phenoxy)-phenoxy]-pyrimidine-2,4,6-trione or pharmaceutically acceptable salts thereof.

Other compounds of the invention include:
  5-[4-(Biphenyl-4-yloxy)-phenoxy]-5-(2-ethoxy-ethyl)-pyrimidine-2,4,6-trione;
  5-[4-(Biphenyl-3-yloxy)-phenoxy]-5-(2-ethoxy-ethyl)-pyrimidine-2,4,6-trione;
  N-(3-{4-[5-(2-Ethoxy-ethyl)-2,4,6-trioxo-hexahydro-pyrimidin-5-yloxy]-phenoxy}-phenyl)-acetamide;
  5-(2-Ethoxy-ethyl)-5-[4-(4-[1,3,4]oxadiazol-2-yl-phenoxy)-phenoxy]-pyrimidine-2,4,6-trione;
  5-(2-Ethoxy-ethyl)-5-[4-(4-[1,2,4]triazol-1-yl-phenoxy)-phenoxy]-pyrimidine-2,4,6-trione;
  5-[4-(4-Aminomethyl-phenoxy)-phenoxy]-5-(2-ethoxy-ethyl)-pyrimidine-2,4,6-trione;
  5-(2-Ethoxy-ethyl)-5-[4-(4-imidazol-1-yl-phenoxy)-phenoxy]-pyrimidine-2,4,6-trione;
  N-(4-{4-[5-(2-Ethoxy-ethyl)-2,4,6-trioxo-hexahydro-pyrimidin-5-yloxy]-phenoxy}-benzyl)-acetamide;
  4-{4-[5-(2-Ethoxy-ethyl)-2,4,6-trioxo-hexahydro-pyrimidin-5-yloxy]-phenoxy}-benzamide;

4'-{4-[5-(2-Ethoxy-ethyl)-2,4,6-trioxo-hexahydro-pyrimidin-5-yloxy]-phenoxy}-biphenyl-4-carbonitrile;

5-(2-Ethoxy-ethyl)-5-[4-(4-methanesulfonyl-phenoxy)-phenoxy]-pyrimidine-2,4,6-trione;

4-{4-[5-(2-Ethoxy-ethyl)-2,4,6-trioxo-hexahydro-pyrimidin-5-yloxy]-phenoxy}-N-methyl-benzamide;

4-{4-[5-(2-Ethoxy-ethyl)-2,4,6-trioxo-hexahydro-pyrimidin-5-yloxy]-phenoxy}-N,N-dimethyl-benzamide;

5-(2-Ethoxy-ethyl)-5-[4-(4-oxazol-4-yl-phenoxy)-phenoxy]-pyrimidine-2,4,6-trione;

5-{4-[4-(5-Dimethylamino-[1,3,4]oxadiazol-2-yl)-phenoxy]-phenoxy}-5-(2-ethoxy-ethyl)-pyrimidine-2,4,6-trione;

5-(2-Ethoxy-ethyl)-5-[4-(4-pyrrol-1-yl-phenoxy)-phenoxy]-pyrimidine-2,4,6-trione;

5-(2-Ethoxy-ethyl)-5-{4-[4-(5-methyl-[1,3,4]oxadiazol-2-yl)-phenoxy]-phenoxy}-pyrimidine-2,4,6-trione;

5-(2-Ethoxy-ethyl)-5-{4-[4-(5-methyl-isoxazol-3-yl)-phenoxy]-phenoxy}-pyrimidine-2,4,6-trione;

5-(2-Ethoxy-ethyl)-5-[4-(6-fluoro-biphenyl-3-yloxy)-phenoxy]-pyrimidine-2,4,6-trione;

2-(4-{4-[5-(2-Ethoxy-ethyl)-2,4,6-trioxo-hexahydro-pyrimidin-5-yloxy]-phenoxy}-phenyl)-acetamide;

5-(2-Ethoxy-ethyl)-5-[4-(4-[1,2,4]triazol-4-yl-phenoxy)-phenoxy]-pyrimidine-2,4,6-trione;

5-[4-(4-Cyclopentyl-phenoxy)-phenoxy]-5-(2-ethoxy-ethyl)-pyrimidine-2,4,6-trione;

5-[4-(4-Cyclohexyl-phenoxy)-phenoxy]-5-(2-ethoxy-ethyl)-pyrimidine-2,4,6-trione;

N-[2-(4-{4-[5-(2-Ethoxy-ethyl)-2,4,6-trioxo-hexahydro-pyrimidin-5-yloxy]-phenoxy}-phenyl)-ethyl]-acetamide;

5-(2-Ethoxy-ethyl)-5-{4-[4-(4H-[1,2,4]triazol-3-yl)-phenoxy]-phenoxy}-pyrimidine-2,4,6-trione;

5-(2-Ethoxy-ethyl)-5-[4-(4-hydroxymethyl-phenoxy)-phenoxy]-pyrimidine-2,4,6-trione;

5-(2-Ethoxy-ethyl)-5-{4-[4-(5-ethyl-[1,3,4]oxadiazol-2-yl)-phenoxy]-phenoxy}-pyrimidine-2,4,6-trione;

N-(4-{4-[5-(2-Ethoxy-ethyl)-2,4,6-trioxo-hexahydro-pyrimidin-5-yloxy]-phenoxy}-benzyl)-3-methyl-butyramide;

Pentanoic acid 4-{4-[5-(2-ethoxy-ethyl)-2,4,6-trioxo-hexahydro-pyrimidin-5-yloxy]-phenoxy}-benzylamide;

5-(2-Ethoxy-ethyl)-5-[4-(4-thiazol-4-yl-phenoxy)-phenoxy]-pyrimidine-2,4,6-trione;

N-(4-{4-[5-(2-Ethoxy-ethyl)-2,4,6-trioxo-hexahydro-pyrimidin-5-yloxy]-phenoxy}-benzyl)-isobutyramide;

N-(4-{4-[5-(2-Ethoxy-ethyl)-2,4,6-trioxo-hexahydro-pyrimidin-5-yloxy]-phenoxy}-benzyl)-2-methoxy-acetamide;

Cyclobutanecarboxylic acid 4-{4-[5-(2-ethoxy-ethyl)-2,4,6-trioxo-hexahydro-pyrimidin-5-yloxy]-phenoxy}-benzylamide;

N-(4-{4-[5-(2-Ethoxy-ethyl)-2,4,6-trioxo-hexahydro-pyrimidin-5-yloxy]-phenoxy}-benzyl)-2-methyl-butyramide;

N-(4-{4-[5-(2-Ethoxy-ethyl)-2,4,6-trioxo-hexahydro-pyrimidin-5-yloxy]-phenoxy}-benzyl)-propionamide;

5-(2-Ethoxy-ethyl)-5-[4-(3-methyl-4-[1,3,4]oxadiazol-2-yl-phenoxy)-phenoxy]-pyrimidine-2,4,6-trione;

5-(2-Ethoxy-ethyl)-5-{4-[3-methyl-4-(5-methyl-[1,3,4]oxadiazol-2-yl)-phenoxy]-phenoxy}-pyrimidine-2,4,6-trione;

5-(2-Ethoxy-ethyl)-5-[4-(4-pyrazol-1-yl-phenoxy)-phenoxy]-pyrimidine-2,4,6-trione;

5-(2-Ethoxy-ethyl)-5-{4-[3-methyl-4-(1H-pyrazol-4-yl)-phenoxy]-phenoxy}-pyrimidine-2,4,6-trione;

5-(2-Ethoxy-ethyl)-5-{4-[3-methyl-4-(1-methyl-1H-pyrazol-4-yl)-phenoxy]-phenoxy}-pyrimidine-2,4,6-trione;

5-(2-Ethoxy-ethyl)-5-{4-[4-(1H-pyrazol-4-yl)-phenoxy]-phenoxy}-pyrimidine-2,4,6-trione;

1-(4-{4-[5-(2-Ethoxy-ethyl)-2,4,6-trioxo-hexahydro-pyrimidin-5-yloxy]-phenoxy}-benzyl)-3-methyl-urea;

5-(2-Ethoxy-ethyl)-5-[4-(3-fluoro-4-[1,3,4]oxadiazol-2-yl-phenoxy)-phenoxy]-pyrimidine-2,4,6-trione;

5-(2-Ethoxy-ethyl)-5-{4-[3-fluoro-4-(5-methyl-[1,3,4]oxadiazol-2-yl)-phenoxy]-phenoxy}-pyrimidine-2,4,6-trione;

5-{4-[3-Fluoro-4-(5-methyl-[1,3,4]oxadiazol-2-yl)-phenoxy]-phenoxy}-5-(tetrahydro-furan-3-yl)-pyrimidine-2,4,6-trione;

5-{4-[3-Fluoro-4-(5-methyl-[1,3,4]oxadiazol-2-yl)-phenoxy]-phenoxy}-5-(tetrahydro-pyran-3-yl)-pyrimidine-2,4,6-trione;

5-{4-[4-(5-Methyl-[1,3,4]oxadiazol-2-yl)-phenoxy]-phenoxy}-5-(tetrahydro-furan-3-yl)-pyrimidine-2,4,6-trione;

5-{4-[4-(5-Methyl-[1,3,4]oxadiazol-2-yl)-phenoxy]-phenoxy}-5-(tetrahydro-pyran-3-yl)-pyramidine-2,4,6-trione;

5-{4-[4-(5-Methyl-[1,3,4]oxadiazol-2-yl)-phenoxy]-phenoxy}-5-(tetrahydro-pyran-2-ylmethyl)pyrimidine-2,4,6-trione;

5-{4-[4-(5-Methyl-[1,3,4]oxadiazol-2-yl)-phenoxy]-phenoxy}-5-(tetrahydro-furan-2-ylmethyl)-pyrimidine-2,4,6-trione;

5-{4-[3-Fluoro-4-(5-methyl-[1,3,4]oxadiazol-2-yl)-phenoxy]-phenoxy}-5-(tetrahydro-furan-2-ylmethyl)-pyrimidine-2,4,6-trione;

5-{4-[3-Methyl-4-(5-methyl-[1,3,4]oxadiazol-2-yl)-phenoxy]-phenoxy}-5-(tetrahydro-furan-2-ylmethyl)pyrimidine-2,4,6-trione;

5-(4-Methyl-5-oxo-morpholin-2-ylmethyl)-5-[4-(4-[1,3,4]oxadiazol-2-yl-phenoxy)-phenoxy]-pyrimidine-2,4,6-trione;

5-(4-Methyl-3-oxo-morpholin-2-ylmethyl)-5-[4-(4-[1,3,4]oxadiazol-2-yl-phenoxy)-phenoxy]-pyrimidine-2,4,6-trione;

N-Isopropyl-2-{5-[4-(4-[1,3,4]oxadiazol-2-yl-phenoxy)-phenoxy]-2,4,6-trioxo-hexahydro-pyrimidine-5yl}-acetamide;

N-(2-{5-[4-(4-[1,3,4]Oxadiazol-2-yl-phenoxy)-phenoxy]-2,4,6-trioxo-hexahydro-pyrimidine-5yl}-ethyl)-isobutyramide;

5-{4-[4-(5-Methyl-[1,3,4]oxadiazol-2-yl)-phenoxy]-phenoxy}-5-pyridin-2-ylmethyl-pyrimidine-2,4,6-trione;

5-{4-[4-(5-Methyl-[1,3,4]oxadiazol-2-yl)-phenoxy]-phenoxy}-5-pyridin-3-ylmethyl-pyrimidine-2,4,6-trione;

5-{4-[4-(5-Methyl-[1,3,4]oxadiazol-2-yl)-phenoxy]-phenoxy}-5-pyridin-4-ylmethyl-pyrimidine-2,4,6-trione;

5-{4-[6-(5-Methyl-[1,3,4]oxadiazol-2-yl)-pyridin-3-yloxy]-phenoxy}-5-(tetrahydro-furan-2-ylmethyl)-pyrimidine-2,4,6-trione;

5-[4-(4-Oxazol-2-yl-phenoxy)-phenoxy]-5-(tetrahydro-furan-2-ylmethyl)-pyrimidine-2,4,6-trione;

5-{4-[4-(2-Oxo-pyrrolidin-1-ylmethyl)-phenoxy]-phenoxy}-5-(tetrahydro-furan-2-ylmethyl)-pyrimidine-2,4,6-trione;

Cyclobutanecarboxylic acid 4-{4-[2,4,6-trioxo-5-(tetrahydro-furan-2-ylmethyl)-hexahydro-pyrimidin-5-yloxy]-phenoxy}-benzylamide;

5-[4-(4-Pyrazol-1-ylmethyl-phenoxy)-phenoxy]-5-(tetrahydro-furan-2-ylmethyl)-pyrimidine-2,4,6-trione;

(5-{4-[4-(5-Methyl-[1,3,4]oxadiazol-2-yl)-phenoxy]-phenoxy}-2,4,6-trioxo-hexahydro-pyrimidin-5-yl)-acetic acid;

(5-{4-[3-Methyl-4-(5-methyl-[1,3,4]oxadiazol-2-yl)-phenoxy]-phenoxy}-2,4,6-trioxo-hexahydro-pyrimidin-5-yl)-acetic acid;

(5-{4-[3-Fluoro-4-(5-methyl-[1,3,4]oxadiazol-2-yl)-phenoxy]-phenoxy}-2,4,6-trioxo-hexahydro-pyrimidin-5-yl)-acetic acid;

3-{5-[4-(4-([1,3,4-Oxadiazol-2-yl)-phenoxy)-phenoxy]-2,4,6-trioxo-hexahydro-pyrimidin-5-yl}-N,N-dimethyl-propionamide;

5-[4-(Biphenyl-4-yloxy)-phenoxy]-5-(cyclohexyl)-pyrimidine-2,4,6-trione;

5-[4-(Biphenyl-3-yloxy)-phenoxy]-5-(cyclohexyl)-pyrimidine-2,4,6-trione;

N-(3-{4-[5-(cyclohexyl)-2,4,6-trioxo-hexahydro-pyrimidin-5-yloxy]-phenoxy}-phenyl)-acetamide;

5-(cyclohexyl)-5-[4-(4-[1,3,4]oxadiazol-2-yl-phenoxy)-phenoxy]-pyrimidine-2,4,6-trione;

5-(cyclohexyl)-5-[4-(4-[1,2,4]triazol-1-yl-phenoxy)-phenoxy]-pyrimidine-2,4,6-trione;

5-[4-(4-Aminomethyl-phenoxy)-phenoxy]-5-(cyclohexyl)-pyrimidine-2,4,6-trione;

5-(cyclohexyl)-5-[4-(4-imidazol-1-yl-phenoxy)-phenoxy]-pyrimidine-2,4,6-trione;

N-(4-{4-[5-(cyclohexyl)-2,4,6-trioxo-hexahydro-pyrimidin-5-yloxy]-phenoxy}-benzyl)-acetamide;

4-{4-[5-(cyclohexyl)-2,4,6-trioxo-hexahydro-pyrimidin-5-yloxy]-phenoxy}-benzamide;

4'-{4-[5-(cyclohexyl)-2,4,6-trioxo-hexahydro-pyrimidin-5-yloxy]-phenoxy}-biphenyl-4-carbonitrile;

5-(cyclohexyl)-5-[4-(4-methanesulfonyl-phenoxy)-phenoxy]-pyrimidine-2,4,6-trione;

4-{4-[5-(cyclohexyl)-2,4,6-trioxo-hexahydro-pyrimidin-5-yloxy]-phenoxy}-N-methyl-benzamide;

4-{4-[5-(cyclohexyl)-2,4,6-trioxo-hexahydro-pyrimidin-5-yloxy]-phenoxy}-N,N-dimethyl-benzamide;

5-(cyclohexyl)-5-[4-(4-oxazol-5-yl-phenoxy)-phenoxy]-pyrimidine-2,4,6-trione;

5-(cyclohexyl)-5-[4-(4-oxazol-4-yl-phenoxy)-phenoxy]-pyrimidine-2,4,6-trione;

5-{4-[4-(5-Dimethylamino-[1,3,4]oxadiazol-2-yl)-phenoxy]-phenoxy}-5-(cyclohexyl)-pyrimidine-2,4,6-trione;

5-(cyclohexyl)-5-[4-(4-pyrrol-1-yl-phenoxy)-phenoxy]-pyrimidine-2,4,6-trione;

5-(cyclohexyl)-5-{4-[4-(5-methyl-[1,3,4]oxadiazol-2-yl)-phenoxy]-phenoxy}-pyrimidine-2,4,6-trione;

5-(cyclohexyl)-5-{4-[4-(5-methyl-isoxazol-3-yl)-phenoxy]-phenoxy}-pyrimidine-2,4,6-trione;

5-(cyclohexyl)-5-{4-[4-(6-fluoro-biphenyl-3-yloxy)-phenoxy]-phenoxy}-pyrimidine-2,4,6-trione;

2-(4-{4-[5-(cyclohexyl)-2,4,6-trioxo-hexahydro-pyrimidin-5-yloxy]-phenoxy}-phenyl)-acetamide;

5-(cyclohexyl)-5-[4-(4-[1,2,4]triazol-4-yl-phenoxy)-phenoxy]-pyrimidine-2,4,6-trione;

5-(cyclohexyl)-5-{4-[4-(1H-pyrazol-3-yl)-phenoxy]-phenoxy}-pyrimidine-2,4,6-trione;

5-(cyclohexyl)-5-{4-[4-(2-methyl-thiazol-4-yl)-phenoxy]-phenoxy}-pyrimidine-2,4,6-trione;

5-(4-{4-[5-(cyclohexyl)-2,4,6-trioxo-hexahydro-pyrimidin-5-yloxy]-phenoxy}-phenyl)-pentanenitrile;

5-[4-(4-Cyclopentyl-phenoxy)-phenoxy]-5-(cyclohexyl)-pyrimidine-2,4,6-trione;

5-[4-(4-Cyclohexyl-phenoxy)-phenoxy]-5-(cyclohexyl)-pyrimidine-2,4,6-trione;

N-[2-(4-{4-[5-(cyclohexyl)-2,4,6-trioxo-hexahydro-pyrimidin-5-yloxy]-phenoxy}-phenyl)-ethyl]-acetamide;

5-(cyclohexyl)-5-{4-[4-(4H-[1,2,4]triazol-3-yl)-phenoxy]-phenoxy}-pyrimidine-2,4,6-trione;

5-(cyclohexyl)-5-{4-[4-(1-methyl-1H-pyrazol-3-yl)-phenoxy]-phenoxy}-pyrimidine-2,4,6-trione;

5-(cyclohexyl)-5-{4-[4-(2-methyl-2H-pyrazol-3-yl)-phenoxy]-phenoxy}-pyrimidine-2,4,6-trione;

5-(cyclohexyl)-5-[4-(4-hydroxymethyl-phenoxy)-phenoxy]-pyrimidine-2,4,6-trione;

5-(cyclohexyl)-5-{4-[4-(5-ethyl-[1,3,4]oxadiazol-2-yl)-phenoxy]-phenoxy}-pyrimidine-2,4,6-trione;

N-(4-{4-[5-(cyclohexyl)-2,4,6-trioxo-hexahydro-pyrimidin-5-yloxy]-phenoxy}-benzyl)-3-methyl-butyramide;

Pentanoic acid 4-{4-[5-(cyclohexyl)-2,4,6-trioxo-hexahydro-pyrimidin-5-yloxy]-phenoxy}-benzylamide;

5-(cyclohexyl)-5-[4-(4-thiazol-4-yl-phenoxy)-phenoxy]-pyrimidine-2,4,6-trione;

N-(4-{4-[5-(cyclohexyl)-2,4,6-trioxo-hexahydro-pyrimidin-5-yloxy]-phenoxy}-benzyl)-isobutyramide;

N-(4-{4-[5-(cyclohexyl)-2,4,6-trioxo-hexahydro-pyrimidin-5-yloxy]-phenoxy}-benzyl)-2-methoxy-acetamide;

Cyclobutanecarboxylic acid 4-{4-[5-(cyclohexyl)-2,4,6-trioxo-hexahydro-pyrimidin-5-yloxy]-phenoxy}-benzylamide;

N-(4-{4-[5-(cyclohexyl)-2,4,6-trioxo-hexahydro-pyrimidin-5-yloxy]-phenoxy}-benzyl)-2-methyl-butyramide;

N-(4-{4-[5-(cyclohexyl)-2,4,6-trioxo-hexahydro-pyrimidin-5-yloxy]-phenoxy}-benzyl)-propionamide;

5-(cyclohexyl)-5-[4-(4-thiazol-2-yl-phenoxy)-phenoxy]-pyrimidine-2,4,6-trione;

5-(cyclohexyl)-5-[4-(4-pyrimidin-4-yl-phenoxy)-phenoxy]-pyrimidine-2,4,6-trione;

5-(cyclohexyl)-5-[4-(3-methyl-4-[1,3,4]oxadiazol-2-yl-phenoxy)-phenoxy]-pyrimidine-2,4,6-trione;

5-(cyclohexyl)-5-{4-[3-methyl-4-(5-methyl-[1,3,4]oxadiazol-2-yl)-phenoxy]-phenoxy}-pyrimidine-2,4,6-trione;

5-(cyclohexyl)-5-[4-(4-pyrazol-1-yl-phenoxy)-phenoxy]-pyrimidine-2,4,6-trione;

5-(cyclohexyl)-5-{4-[3-methyl-4-(1H-pyrazol-4-yl)-phenoxy]-phenoxy}-pyrimidine-2,4,6-trione;

5-(cyclohexyl)-5-{4-[3-methyl-4-(1-methyl-1H-pyrazol-4-yl)-phenoxy]-phenoxy}-pyrimidine-2,4,6-trione;

5-(cyclohexyl)-5-{4-[4-(1H-pyrazol-4-yl)-phenoxy]-phenoxy}-pyrimidine-2,4,6-trione;

1-(4-{4-[5-(cyclohexyl)-2,4,6-trioxo-hexahydro-pyrimidin-5-yloxy]-phenoxy}-benzyl)-3-methyl-urea;

1-(4-{4-[5-(cyclohexyl)-2,4,6-trioxo-hexahydro-pyrimidin-5-yloxy]-phenoxy}-benzyl)-3-propyl-urea; and Azetidine-1-carboxylic acid 4-{4-[5-(cyclohexyl)-2,4,6-trioxo-hexahydro-pyrimidin-5-yloxy]-phenoxy}-benzylamide;

5-(cyclohexyl)-5-[4-(3-fluoro-4-[1,3,4]oxadiazol-2-yl-phenoxy)-phenoxy]-pyrimidine-2,4,6-trione;

5-(cyclohexyl)-5-{4-[3-fluoro-4-(5-methyl-[1,3,4]oxadiazol-2-yl)-phenoxy]-phenoxy}-pyrimidine-2,4,6-trione;

1-(4-{4-[5-(2-Ethoxy-ethyl)-2,4,6-trioxo-hexahydro-pyrimidin-5-yloxy]-phenoxy}-benzyl)-3-propyl-urea; and Azetidine-1-carboxylic acid 4-{4-[5-(2-ethoxy-ethyl)-2,4,6-trioxo-hexahydro-pyrimidin-5-yloxy]-phenoxy}-benzylamide;

or pharmaceutically acceptable salts thereof.

The present invention also relates to a pharmaceutical composition for the treatment of a condition selected from the group consisting of connective tissue disorders, inflammatory disorders, immunology/allergy disorders, infectious diseases, respiratory diseases, cardiovascular diseases, eye diseases, metabolic diseases, central nervous system (CNS) disorders, liver/kidney diseases, reproductive health disorders, gastric disorders, skin disorders and cancers and other diseases characterized by metalloproteinase activity in a mammal, including a human, comprising an amount of a compound of formula I or a pharmaceutically acceptable salt thereof effective in such treatments and a pharmaceutically acceptable carrier.

The present invention also relates to a pharmaceutical composition for the inhibition of matrix metalloproteinases or other metalloproteinases involved in matrix degradation, in a mammal, including a human, comprising an effective amount of a compound of formula I or a pharmaceutically acceptable salt thereof.

The present invention also relates to a method for treating a condition selected from the group consisting of connective tissue disorders, inflammatory disorders, immunology/allergy disorders, infectious diseases, respiratory diseases, cardiovascular diseases, eye diseases, metabolic diseases, central nervous system (CNS) disorders, liver/kidney diseases, reproductive health disorders, gastric disorders, skin disorders and cancers and other diseases characterized by matrix metalloproteinase activity in a mammal, including a human, comprising administering to said mammal an amount of a compound of formula I or a pharmaceutically acceptable salt thereof effective in treating such a condition.

The present invention also relates to a method for the inhibition of matrix metalloproteinases or other metalloproteinases involved in matrix degradation, in a mammal, including a human, comprising administering to said mammal an effective amount of a compound of formula I or a pharmaceutically acceptable salt thereof.

The present inventors have also discovered that it is possible to identify inhibitors of formula I with differential metalloprotease activity (preferably MMP-13 inhibitory activity). One group of preferred inhibitors of formula I the inventors have been able to identify include those which selectively inhibit MMP-13 preferentially over MMP-1. The compounds of the invention also possess selectivity over a related group of enzymes known as reprolysins, such as TACE and aggrecanase. Another group of preferred inhibitors of formula I the inventors have been able to identify include those which selectively inhibit MMP-13 preferentially over MMP-1 and MMP-14. Another group of preferred inhibitors of formula I the inventors have been able to identify include those which selectively inhibit MMP-13 preferentially over MMP-1 and 12. Another group of preferred inhibitors of formula I the inventors have been able to identify include those which selectively inhibit MMP-13 preferentially over MMP-1, 12 and 14. Another group of preferred inhibitors of formula I the inventors have been able to identify include those which selectively inhibit MMP-13 preferentially over MMP-1, 2, 3, 7, 9 and 14. Most preferred compounds of the invention selectively inhibit MMP-13 preferentially over MMP-1, 2, 3, 7, 9, 12 and 14 and mammalian reprolysins.

The present invention also relates to a method for treating a medical condition of the type that is characterized by the destruction of articular cartilage in a mammalian subject, which method comprises administering to the subject having said condition a therapeutically effective amount of a suitably substituted pyrimidine-2,4,6-trione, wherein said suitably substituted pyrimidine-2,4,6-trione exhibits: i) a MMP-13 $IC_{50}$ of less than about 100 nM (more preferably 50 nM, most preferably less than 20 nM), said MMP-13 $IC_{50}$ measured by an recombinant MMP-13 assay, ii) a MMP-1 $IC_{50}$ of greater than about 200 nM (more preferably greater than 500 nM, most preferably greater than 1$\mu$M), said MMP-1 $IC_{50}$ measured by a recombinant MMP-1 assay; and iii) a MMP-14 $IC_{50}$ of greater than about 200 nM (more preferably greater than 500 nM, most preferably greater than 1 $\mu$M), said MMP-14 $IC_{50}$ measured by a recombinant MMP-14 assay.

The present invention also relates to a method for treating the destruction of articular cartilage wherein said pyrimidine-2,4,6-trione additionally exhibits a MMP-12 $IC_{50}$ of greater than about 100 nM (more preferably greater than 200 nM, most preferably greater than 500 nM), said MMP-12 $IC_{50}$ measured by a recombinant MMP-12 assay.

The present invention also relates to a method for treating the destruction of articular cartilage wherein said pyrimidine-2,4,6-trione additionally exhibits i) a MMP-2 $IC_{50}$ of greater than about 200 nM (more preferably greater than 500 nM, most preferably greater than 1 $\mu$M), said MMP-2 $IC_{50}$ measured by a recombinant MMP-2 assay, ii). a MMP-3 $IC_{50}$ of greater than about 200 nM (more preferably greater than 500 nM, most preferably greater than 1 $\mu$M), said MMP-3 $IC_{50}$ measured by a recombinant MMP-3 assay, iii) a MMP-7 $IC_{50}$ of greater than about 200 nM (more preferably greater than 500 $\mu$M, most preferably greater than 1 uM), said MMP-7 $IC_{50}$ measured by a recombinant MMP-7 assay, and iv) a MMP-9 $IC_{50}$ of greater than about 200 nM (more preferably greater than 500 nM, most preferably greater than 1 $\mu$M), said MMP-9 $IC_{50}$ measured by a recombinant MMP-9 assay.

The term "treating", as used herein, refers to reversing, alleviating, inhibiting the progress of, or preventing the disorder or condition to which such term applies, or one or more symptoms of such disorder or condition. The term "treatment", as used herein, refers to the act of treating, as "treating" is defined immediately above.

"Connective tissue disorders" as used herein refers to disorders such as degenerative cartilage loss following traumatic joint injury, osteoarthritis, osteoporosis, Paget's disease, loosening of artificial joint implants, periodontal disease and gingivitis.

"Destruction of articular cartilage" as used herein refers to connective tissue disorders resulting in articular cartilage destruction, preferably joint injury, reactive arthritis, acute pyrophosphate arthritis (pseudogout), psoriatic arthritis, or juvenile rheumatoid arthritis, more preferably osteoarthritis.

"Inflammatory disorders" as used herein refers to disorders such as rheumatoid arthritis, ankylosing spondylitis, psoriatic arthritis, psoriasis, chondrocalcinosis, gout, inflammatory bowel disease, ulcerative colitis, Crohn's disease and cachexia.

"Immunology/allergy disorders" as used herein refers to disorders such as organ transplant toxicity, allergic reactions, allergic contact hypersensitivity, autoimmune disorders such as those disorders associated with granulomatous inflammation/tissue remodeling (such as asthma), immunosuppression and sarcoid.

"Infectious diseases," including those mediated by viruses, bacteria, fungi or mycobacterial infection, as used herein refers to disorders such as septic arthritis, AIDS, fever; Prion diseases, myasthenia gravis, Malaria, sepsis, hemodynamic shock, and septic shock.

"Respiratory diseases" as used herein refers to disorders such as chronic obstructive pulmonary disease (including emphysema), acute respiratory distress syndrome, asthma, hyperoxic alveolar injury and idiopathic pulmonary fibrosis and other fibrotic lung diseases.

"Cardiovascular diseases" as used herein refers to disorders such as atherosclerosis including atherosclerotic plaque rupture; aortic aneurysm including abdominal aortic aneurysm and brain aortic aneurysm; congestive heart failure; myocardial and cerebral infarction; stroke; cerebral ischemia; coagulation and acute phase response; left ventricular dilation; post ischemic reperfusion injury; angiofibromas; hemangiomas; and restenosis.

"Eye diseases" as used herein refers to disorders such as aberrant angiogenesis, ocular angiogenesis, ocular inflammation, keratoconus, Sjogren's syndrome, myopia, ocular tumors, corneal graft rejection, corneal injury, neovascular glaucoma, corneal ulceration, corneal scarring, macular degeneration (including "Age Related Macular Degeneration (ARMD) including both wet and dry forms), proliferative vitreoretinopathy and retinopathy of prematurity.

"Metabolic diseases" as used herein refers to disorders such as diabetes (including non-insulin dependent diabetes mellitus, diabetic retinopathy, insulin resistance, diabetic ulceration).

"Central Nervous System" (CNS) disorders as used herein refers to disorders such as head trauma, spinal cord injury, Inflammatory diseases of the central nervous system, neurodegenerative disorders (acute and chronic), Alzheimer's disease, demyelinating diseases of the nervous system, Huntington's disease, Parkinson's disease, peripheral neuropathy, pain, cerebral amyloid angiopathy, nootropic or cognition enhancement, amyotrophic lateral sclerosis, multiple sclerosis, migraine, depression and anorexia.

"Liver/Kidney diseases" as used herein refers to disorders such as nephrotic syndromes such as glomerulonephritis and glomerular disease of the kidney, proteinuria, cirrhosis of the liver and interstitial nephritis.

"Reproductive Health disorders" as used herein refers to disorders such as endometriosis, contraception (male/female), dysmenorrhea, dysfunctional uterine bleeding, premature rupture of fetal membranes and abortifactant.

"Gastric disorders" as used herein refers to disorders such as colonic anastomosis and gastric ulcers.

"Skin disorders" as used herein refers to disorders such as skin aging, pressure sores, psoriasis, eczema, dermatitis, radiation damage, tissue ulceration, decubital ulcers, epidermolysis bullosa, abnormal wound healing (topical and oral formulations), burns and scleritis.

"Cancers" as used herein refers to disorders such as solid tumor cancer including colon cancer, breast cancer, lung cancer and prostrate cancer, tumor invasion, tumor growth tumor metastasis, cancers of the oral cavity and pharynx (lip, tongue, mouth, pharynx), esophagus, stomach, small intestine, large intestine, rectum, liver and biliary passages, pancreas, larynx, lung, bone, connective tissue, skin, cervix uteri, corpus endometrium, ovary, testis, bladder, kidney, and other urinary tissues, eye brain and central nervous system, thyroid and other endocrine gland, Hodgkin's disease, non-Hodgkin's lymphomas, multiple myeloma, and hematopoietic malignancies including leukemias and lymphomas including lymphocytic, granulocytic and monocytic.

The subject invention also includes isotopically-labelled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{31}$P, $^{32}$P, $^{35}$P, $^{18}$F, and $^{36}$Cl, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically-labelled compounds of Formula I of this invention and prodrugs thereof can generally be prepared by carrying out the procedures disclosed in the Schemes and/or in the Examples and Preparations below, by substituting a readily available isotopically-labelled reagent for a non-isotopically-labelled reagent.

This invention also encompasses pharmaceutical compositions containing prodrugs of compounds of the formula I. This invention also encompasses methods of treating or preventing disorders that can be treated or prevented by the inhibition of matrix metalloproteinases or the inhibition of mammalian reprolysin comprising administering prodrugs of compounds of the formula I. Compounds of formula I having free amino, amido, hydroxy, sulfonamide or carboxylic groups can be converted into prodrugs. Prodrugs include compounds wherein an amino acid residue, or a polypeptide chain of two or more (e.g., two, three or four) amino acid residues which are covalently joined through peptide bonds to free amido, amino, hydroxy or carboxylic acid groups of compounds of formula I. The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Prodrugs also include compounds wherein carbonates, carbamates, amides and alkyl esters, which are covalently, bonded to the above substituents of formula I through the carbonyl carbon prodrug sidechain. Prodrugs also include dimers of compounds of formula I.

One of ordinary skill in the art will appreciate that the compounds of the invention are useful in treating a diverse array of diseases. One of ordinary skill in the art will also appreciate that when using the compounds of the invention in the treatment of a specific disease that the compounds of the invention may be combined with various existing therapeutic agents used for that disease.

For the treatment of rheumatoid arthritis, the compounds of the invention may be combined with agents such as TNF-α inhibitors such as anti-TNF monoclonal antibodies (such as infliximab, D2E7 and CDP-870) and TNF receptor immunoglobulin molecules (such as etanercept), ICE inhibitors, MEKK1 inhibitors, COX-2 inhibitors such as celecoxib, rofecoxib, valdecoxib and etoricoxib; low dose methotrexate, lefunimide, steroids, glucosamines, chondrosamines/sulfates, gabapentin, A-agonists, IL-1 process and release inhibitors, IL-1 receptor antagonists such as Kineret®, CCR-1 antagonists, hydroxychloroquine, d-penicilamine, auranofin or parenteral or oral gold.

The compounds of the invention can also be used in combination with existing therapeutic agents for the treatment of osteoarthritis. Suitable agents to be used in combination include standard non-steroidal anti-inflammatory agents (hereinafter NSAID's) such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib, valdecoxib, paracoxib, etoricoxib and rofecoxib, analgesics, steroids, glucosamines, chondrosamines/sulfates, gabapentin, A-agonists, IL-1 process and release inhibitors, CCR-1 antagonists, LTD-4, LTB-4 and 5-LO inhibitors, p38 kinase inhibitors and intraarticular therapies such as corticosteroids and hyaluronic acids such as hyalgan and synvisc.

The compounds of the present invention may also be used in combination with anticancer agents such as endostatin and angiostatin or cytotoxic drugs such as adriamycin, daunomycin, cis-platinum, etoposide, paclitaxel, docetaxel and alkaloids, such as vincristine, and antimetabolites such as methotrexate.

The compounds of the present invention may also be used in combination with cardiovascular agents such as calcium channel blockers (such as amlodipine and nifedipine), lipid lowering agents such as statins (such as lovastatin, atorvastatin, pravastatin and simvastatin), adrenergics such as doxazosin and terazosin; fibrates, beta-blockers, Ace inhibitors (such as captopril, lisinopril, fosinopril, enalapril and quinapril), Angiotensin-2 receptor antagonists such as losartan and irbesartan; nitrates, CCB's, diuretics such as digitalis, and platelet aggregation inhibitors. The compounds of the present invention may also be used in combination with plaque rupture preventative agents such as statins, zithromax, NSAIDs including aspirin, heparin, urarfarin, abciximab, TPA and platelet Inhibitors. The compounds of the present invention may also be used in combination with stroke treatment agents such as NIF, NHEI's and CCRIR antagonists.

The compounds of the present invention may also be used in combination with CNS agents such as antidepressants (such as sertraline), anti-Parkinsonian drugs (such as deprenyl, carbadopa, L-dopa, dopamine receptor agonists such as ropinirole, pergolide and pramipexole; MAOB inhibitors such as selegiline and rasagiline, catechol-O-methyltrasferase inhibitors such as tolcapone, A-2 inhibitors, dopamine reuptake inhibitors, NMDA antagonists, Nicotine agonists, NK-1 inhibitors, dopamine agonists and inhibitors of neuronal nitric oxide synthase), and anti-Alzheimer's drugs such as donepezil, tacrine, COX-2 inhibitors, propentofylline or metryfonate.

The compounds of the present invention may also be used in combination with osteoporosis agents such as roloxifene, droloxifene, lasofoxifene or fosomax and immunosuppressant agents such as FK-506 and rapamycin.

The compounds of the present invention may also be used in combination with agents for the treatment of respiratory diseases such as PDE-IV inhibitors, steroidals such as fluticasone, triamcinolone, budesonide, budesonide and beclomethasone, anticholinergics such as ipratropium, sympathomimetics such as salmeterol, albuterol and Xopenex, decongestants such as fexofenadine, loratadine, and cetirizine; leukotriene antagonists such as zafirlukast and motelukast; and mast cell stabilizers such as zileuton.

The compounds of the present invention may also be used in combination with agents for the treatment of skin disorders such as tretinoin, isotretinoin, steroids such as cortisone and mometasone, antibiotics such as tetracycline, antifungals such as clotrimazole, miconazole and fluconazole and PDE-IV inhibitors.

The compounds of the present invention may also be used in combination with agents for the treatment of diabetes such as insulin, including human or humanized insulin and inhaled insulin, aldose reductase inhibitors, sorbitol dehydrogenase inhibitors, antidiabetic agents such as biguanides such as metformin; glitazones, glycosidase inhibitors such as acarbose, sulfonylureas such as glimepiride and glipizide; and thiazolidinediones such as pioglitazone, rosiglitazone and trogliazone. Preferred combinations are useful for treating the side effects of diabetes such as retinopathy, nephropathy and neuropathy, preferably retinopathy.

DETAILED DESCRIPTION OF THE INVENTION

The following reaction Scheme illustrates the preparation of the compounds of the present invention. Unless otherwise indicated X, Y, Ar$^1$, Z, R$^1$, R$^2$ and R$^3$ in the reaction Schemes and the discussion that follows is defined as above.

SCHEME 1

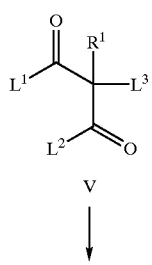

-continued
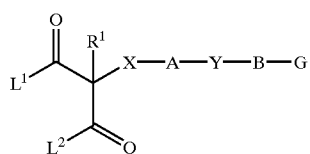
IV
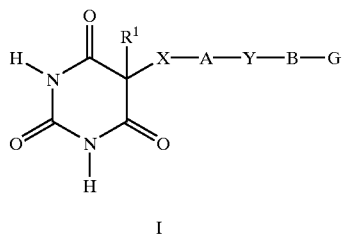
I
SCHEME 2
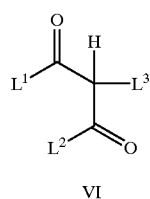
VI
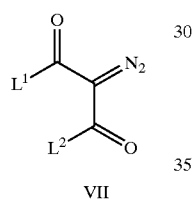
VII
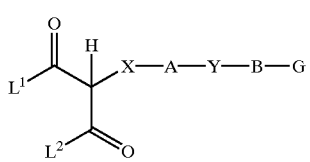
VIII
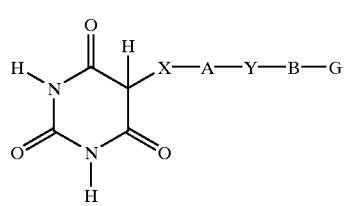
IX
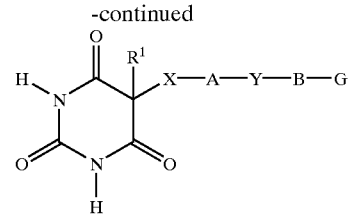
I
SCHEME 3
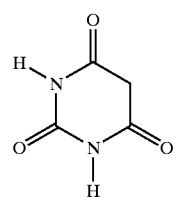
XII
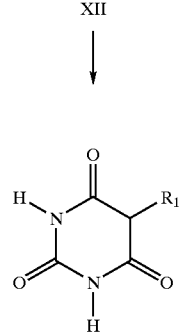
X
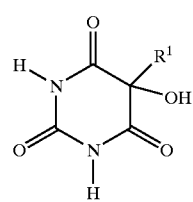
XI
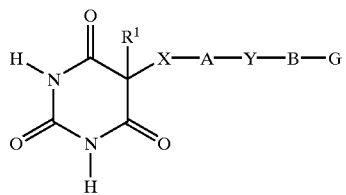
I

SCHEME 4

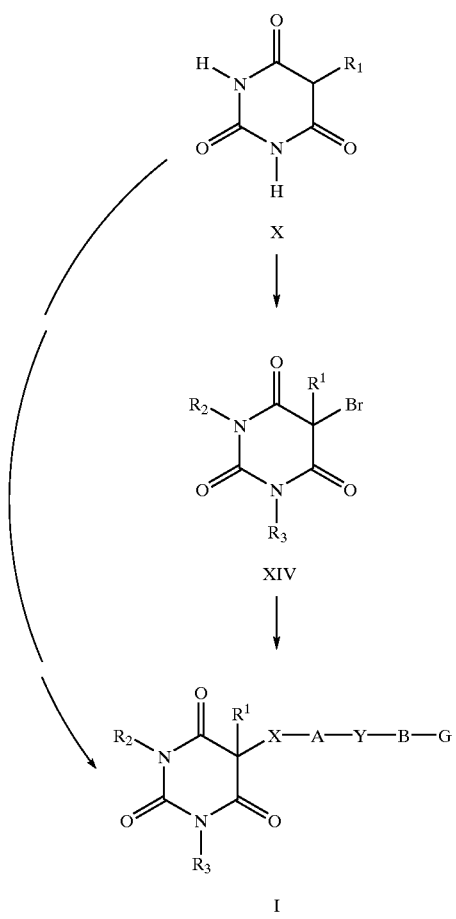

SCHEME 5

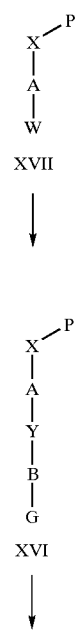

-continued

SCHEME 6

Scheme 1 refers to the preparation of compounds of the formula I in a two step synthesis from compounds of the formula V. Referring to Scheme 1, a compound of the formula I is prepared from a compound of the formula IV, wherein $L^1$ and $L^2$ are leaving groups such as methoxy, ethoxy, benzyloxy or chloro, preferably ethoxy, by reaction with a urea of the formula III ($H_2NCONH_2$) in the presence of a strong base in a polar solvent. Suitable bases include sodium methoxide, sodium ethoxide and magnesium methoxide, preferably sodium ethoxide. Suitable solvents include alcohols (such as ethanol) or tetrahydrofuran, preferably absolute ethanol The aforesaid reaction is conducted at a temperature of about 20° C. to about 90° C. preferably about 50° C. to about 65° C. for a time period between about 15 minutes to about 16 hours.

The compound of formula IV is prepared from a compound of formula V, wherein $L^3$ is a leaving group such as halo, p-tolylsulfonyloxy (OTs) or methylsulfonyloxy (OMs), preferably halo, most preferably chloro or bromo, by reaction with a compound of the formula II HX—A—Y—B—G in the presence of a base in a polar solvent. Suitable solvents include dimethylformamide (DMF), alcohols (such as ethanol) or tetrahydrofuran, preferably ethanol. The aforesaid reaction is conducted at a temperature of about 20° C. to about 90° C. preferably about 50° C. to about 65° C. for a time period between about 15 minutes to about 16 hours.

The compounds of the formula V can be made by methods well known in the art such as those described in PCT Patent Publication WO 98/58925 or reviewed in *The Organic Chemistry of Drug Synthesis*, D. Lednicer and L. A. Mitscher, Volume 1, pages 167 to 277 and references therein. Each of the above referenced publications and applications is hereby incorporated by reference in its entirety.

Compounds of the formula III are commercially available or can be made by methods well known to those skilled in the art.

The compounds of formula II, HX—A—Y—B—G, are commercially available or can be made by methods well known to those skilled in the art or can be made by the methods of Scheme 5.

Scheme 2 refers to an alternate preparation of compounds of the formula I in a three-step synthesis from compounds of the formula VI or VII. Referring to Scheme 2, a compound of the formula I is prepared from a compound of the formula IX by reaction with a suitable base and a suitable alkylating agent of the formula $R^1L^4$ in the presence of a solvent. Suitable bases include sodium hydride, potassium carbonate, sodium carbonate, triethylamine, pyridine or triethanolamine; most preferably sodium hydride. Suitable alkylating agents include those wherein $L^4$ is halo, p-tolylsulfonyloxy (OTs) or methylsulfonyloxy (OMs), preferably halo, most preferably chloro or bromo; or alkylating agents include such compounds as Eshenmoser's Salts; epoxides or suitably substituted electrophilic aziridines. Suitable solvents depend upon the base used but may be chosen from N,N-dimethylformamide, tetrahydrofuran, acetonitrile and water. The aforesaid reaction is conducted at a temperature of about 0° C. to about 30° C. preferably about 20° C. to about 25° C. for a time period between about 15 minutes to about 16 hours.

A compound of the formula IX may be prepared from a compound of the formula VIII by reaction with a urea in the presence of a strong base in a polar solvent. Suitable bases include sodium methoxide, sodium ethoxide and magnesium methoxide; preferably sodium ethoxide. Suitable solvents include alcohols (such as ethanol) or tetrahydrofuran, preferably absolute ethanol. The aforesaid reaction is conducted at a temperature of about 20° C. to about 90° C. preferably about 50° C. to about 65° C. for a time period between about 15 minutes to about 16 hours.

A compound of the formula VIII may be prepared from a compound of the formula VI, wherein $L^3$ is a leaving group such as halo, p-tolylsulfonyloxy (OTs) or methylsulfonyloxy (OMs), preferably halo, most preferably chloro, by reaction with a compound of the formula HX—A—Y—B—G in the presence of a base in a polar solvent. Suitable bases include sodium methoxide, sodium ethoxide, potassium carbonate and sodium hydride; preferably sodium ethoxide. Suitable solvents include dimethylformamide (DMF), alcohols (such as ethanol) or tetrahydrofuran, preferably ethanol. The aforesaid reaction is conducted at a temperature of about 20° C. to about 90° C. preferably about 50° C. to about 70° C. for a time period between about 15 minutes to about 16 hours, preferably about 3 hours. Reactions of this type are further illustrated by the method of J. B. Niederl and R. T. Roth, *J. Amer. Chem. Soc.*, 62,1154 (1940).

Alternatively, a compound of the formula VIII may also be prepared from a compound of the formula VII in the presence of a suitable catalyst, preferably rhodium(II)acetate according to the procedure described by M. Campbell et al., *Aust. J. Chem.*, 45, 2061 (1992).

Compounds of the formula VI and VII are commercially available or easily obtained from readily available starting materials according to methods well known to those skilled in the art. For example compounds of the Formula VII may be prepared according to the method of D. W. Peace et al., *Synthesis*, 658 (1971).

Compounds of the formula ill are commercially available or can be prepared by methods well known to those skilled in the art.

Scheme 3 refers to an alternate preparation of compounds of the formula I; in particular those wherein X is oxygen or —OCH$_2$—. Referring to Scheme 3, a compound of the formula I may be obtained by alkylation of a compound of the formula XI with a suitable phenol of the formula HO—A—Y—B—G according to the method of O. Mitsonubu (Synthesis, 1 (1981)) or by alkylation with a suitable alkylating agent of the formula $L^3CH_2A$—Y—B—G wherein L3 is a leaving group such as halo, p-tolylsulfonyloxy (OTs) or methylsulfonyloxy (OMs), preferably halo, most preferably chloro or bromo in a suitable solvent such as N,N-dimethylformamide, tetrahydrofuran, acetonitrile in the presence of a suitable base such as sodium hydride, potassium carbonate, triethylamine, pyridine or triethanolamine. The aforesaid reaction is conducted at a temperature of about 0° C. to about 50° C. preferably about 20° C. for a time period between about 15 minutes to about 16 hours.

Compounds of the formula X may be prepared from compounds of the formula X according to the method of J. A. Vida et al., *J. Med. Chem.*, 17, 732 (1974).

Compounds of the formula X may be prepared from a compound of the formula XII by reaction with a suitable base, in the presence of a suitable alkylating agent of the formula $R^1L^4$ and a solvent, such as described in Biehl et al., *J.Het.Chem.*, 23, 9 (1986). Suitable bases include sodium hydride, potassium carbonate, triethylamine, pyridine, triethanolamine; most preferably triethanolamine. Suitable alkylating agents include those wherein $L^4$ is halo, p-tolylsulfonyloxy (OTs) or methylsulfonyloxy (OMs), preferably halo, most preferably chloro or bromo; or alkylating agents such as Eshenmoser's Salt; epoxides or suitably substituted electrophilic aziridines. Suitable solvents depend upon the base used but may be chosen from N,N-dimethylformamide, tetrahydrofuran, acetonitrile and water. The aforesaid reaction is conducted at a temperature of about 0° C. to about 30° C. preferably about 20° C. to about 25° C. for a time period between about 15 minutes to about 16 hours.

Compounds of the formula XII are commercially available or can be easily prepared by those skilled in the art according to the methods reviewed in *The Organic Chemistry of Drug Synthesis*, D. Lednicer and L. A. Mitscher, Volume 1, pages 167 to 277 and references cited therein.

Scheme 4 refers to an alternate preparation of compounds of the formula 1. Referring to Scheme 4, a compound of the formula I may be obtained by alkylation of the compound of formula XIV with a compound of the formula HX—A—Y—B—G in the presence of a base. Suitable bases include polymer bound bases such as 1,5,7-trazabicyclo[4.4.0]dec-5-ene bound to polystyrene (PTBD) crosslinked with 2% divinyl benzene (DVB) or alkali metal carbonates, preferably PTBD. Suitable solvents include alcohols (such as ethanol, methanol and butanol), DMF, THF or acetonitrile, preferably absolute acetonitrile. The aforesaid reaction is conducted at a temperature of about 20° C. to about 90° C. preferably about 50° C. to about 65° C. for a time period between about 15 minutes to about 16 hours.

The compound of formula XIV is prepared from a compound of formula X by reaction with a suitable bromination reagent such as Br$_2$ or Br$_2$—Ph$_3$P. The bromination may be carried out in a reaction inert solvent such as water (in the presence of a suitable base), acetic acid, acetonitrile or DMF, preferably water. The aforesaid reaction is conducted at a temperature of about 0° C. to about 40° C. preferably about 20° C. to about 35° C. for a time period between about 15 minutes to about 16 hours.

Alternatively, compounds of the formula I wherein X is sulfur or —SCH$_2$—, or their oxidized derivatives >SO$_2$, >SO, —SO$_2$CH$_2$—, —SOCH$_2$—, can be prepared by reacting a pyrimidine-2,4,6-trione ring of a compound of the formula X with a suitable disulfide of the formulae (SA—Y—B—G)$_2$ or (SCH$_2$A—Y—B—G)$_2$ in a suitable solvent such as N,N-dimethylformamide, tetrahydrofuran, acetonitrile in the presence of a suitable base, such as sodium hydride, potassium carbonate, triethylamine, pyridine or triethanolamine. The aforesaid reaction is conducted at a temperature of about 20° C. to about 70° C. preferably about 20° C. for a time period between about 15 minutes to about 16 hours.

Disulfides (SA—Y—B—G)$_2$ or (SCH$_2$A—Y—B—G)$_2$ may be prepared from the corresponding thiols HSA—Y—B—G or HSCH$_2$A—Y—B—G by oxidative methods well known to those skilled the art.

Compounds of the formula X are commercially available, or the methods of scheme 3 or can be made by methods well known to those skilled in the art.

One skilled in the art will also appreciate that the side chains denoted R$^1$ and X—A—Y—B—G may be added as a unit, as is discussed above, or can be added as separate modules such as X—A followed by the addition of a second unit L'—Y—B—G. Such methods are well known to those skilled in the art.

Scheme 5 describes the preparation of intermediates of the formula XV. Intermediates of the formula XV are used to prepare compounds of formula I in Schemes 14. Referring to Scheme 5, compounds of the formula XV, wherein X' is >(C=O)—Cl, OH, SH, >NHR$^{10}$, CH$_2$OH, CH$_2$SH, CH$_2$NHR$^{10}$ and SO$_2$NHR$^{10}$, may be prepared from the appropriate compound of formula XVI by deprotection under conditions commonly known to those of ordinary skill in the art and referenced in Greene and Wuts, "*Protecting Groups in Organic Synthesis*," (John Wiley & Son Press, 2nd Ed). Compounds of the formula XV, wherein X' is —(C=O)—Cl can be prepared from compounds of the formula XVI, wherein P is hydroxy, by reaction with chlorinating agents such as thionyl chloride or phosphorous oxychloride.

Compounds of the formula XVI, wherein Y is O, S, CH$_2$O, CH$_2$S, NR$^{18}$, CH$_2$NR$^{18}$ or SO$_2$NR$^{18}$, can be prepared by treatment of a compound of formula XVII, wherein W is Br or 1, by reaction with a compound of the formula G—Z—YH in the presence of a suitable base, such as an alkali metal carbonate or hydroxide base, preferably potassium carbonate, in the presence of a suitable catalyst, such as a copper (0) catalyst, preferably finely powdered copper bronze in a polar aprotic solvent, such as DMF or NMP at a temperature between about 80° C. and 140° C. for about 6 to 24 hours. Alternatively, coupling may be carried out under Buchwald and Hartwig's conditions in cases, wherein W is Cl, Br, I or triflate (TfO), using a suitable base, such as an alkoxide base, preferably sodium tert-butoxide in a suitable solvent, such as an ethereal solvent, preferably dioxane, in the presence of a palladium (0) catalyst, such as Pd$_2$(dba)$_3$ and a suitable ligand, such as a triaryl phosphine ligand, preferably tri(ortho-tolyl)phosphine at a temperature of about 40° C. to 100° C. for about 1 to 48 hours. Such conditions are reviewed in *Angew. Chem. Int. Ed. Engl.* 1998, 37, 2046–2067 and are well known to those of ordinary skill in the art. Alternatively, coupling may be carried out in cases where W is B(OH)$_2$ using a copper catalyst, preferably copper (II) acetate in the presence of 4 angstrom molecular sieves and a suitable tertiary amine base, such as triethylamine or pyridine, in a suitable solvent, such as methylene chloride, DMSO or THF, under an atmosphere of oxygen gas at a temperature of about 10° C. to 50° C., preferably about 23° C. for about 6 to 72 hours. In certain cases (e.g. where Y is CH$_2$O, CH$_2$S, CH$_2$NR$^{18}$ or SO$_2$NR$^{18}$), it may be advantageous to use a compound of formula XVII, wherein X is CHO and W is F, for the conversion to compound XVI by treatment with a compound of formula G—Z—YH in the presence of a suitable base, such as an alkali metal hydride base, preferably sodium hydride, in a polar aprotic solvent, such as DMF or THF, at a temperature of 0° C. to 140° C. for 1 to 24 hours. Such compounds can be converted into compounds of the formula XVI, wherein X is O, by so-called Bayer Villager oxidation conditions or to compounds of formula XVI, wherein X is NR$^{18}$, by the so-called Curtius rearrangement, both of which are classical organic transformations and well known to those of ordinary skill in the art.

Compounds of the formula XVI, wherein Y is >SO$_2$, >S=O, —CH$_2$SO—, —CH$_2$SO$_2$—, SO(CH$_2$)$_n$—, —SO$_2$(CH$_2$)$_n$—, may be prepared from the corresponding lower oxidation state compounds (e.g. wherein Y is —S—, —CH$_2$S—, —S—(CH$_2$)$_n$—) by oxidation with a suitable oxidant, such as a peroxy acid, preferably peracetic acid, or an organic peroxide, preferably m-chloroperoxybenzoic acid or tert-butyl hydroperoxide, in a suitable solvent, such as methylene chloride or t-butanol, at a temperature between about –10° C. and 30° C. for 1 to 8 hours.

Compounds of the formula XVI, wherein Y is O(CH$_2$)$_n$, S(CH$_2$)$_n$, NR$^{18}$(CH$_2$)$_n$ can be prepared from compounds of the formula XVII, wherein W is L—(CH$_2$)$_n$—, wherein L is halo, mesyloxy (MsO) or tosyloxy (TsO), by treatment with the appropriate compound of the formula G—Z—Y—H, wherein Y is O, S or NR$^{18}$, by treatment with a suitable base, such as an alkali metal carbonate base, preferably potassium carbonate or cesium carbonate, in the presence of a polar aprotic solvent, such as DMF or THF at a temperature between about 23° C. and 80° C., preferably 20 to 50° C. for 1 to 24 hours.

Compounds of the formula XVI, wherein Y is >C=O or CH=CH, can be prepared by treatment of a compound of formula XVII, wherein W is —B(OH)$_2$, —ZnX or —SnR$_3$, with a compound of the formula G—Z—Y—X, wherein X is halo, preferably Cl, Br or I, in the presence of a palladium or nickel catalyst, preferably Pd(PPh$_3$)$_4$, in a suitable solvent, such as toluene, THF, DMF or DMSO at a temperature between 23° C. and 110° C. for a period of 1 to 24 hours. Such reactions may be facilitated by the presence of a copper salt, such as cuprous iodide or cuprous bromide. Compounds of the formula XVI, wherein Y is —C≡C— can be prepared by treatment of a compound of formula XVII, wherein W is halo or triflate, preferably Br or I, with a compound of the formula G—Z—Y—H, in the presence of a suitable base, such as a trialkylamine base, preferably triethylamine and a palladium catalyst, preferably Pd(PPh$_3$)$_4$ in a suitable solvent, such as THF or DMF at a temperature between 23 and 60° C. for a period of 1 to 24 hours. One of ordinary skill in the art will recognize that compounds of the formula XVI, wherein Y is —CH$_2$(CH$_2$)$_n$—, can be prepared by reduction of the aforementioned compounds, wherein Y is —CH=CH— or —C≡C—, by reduction under a hydrogen atmosphere at ambient pressure to 50 psi in the presence of a palladium catalyst, preferably palladium on charcoal, in a suitable solvent, such as methanol or ethyl acetate, at a temperature between about 20° C. and 50° C. for about 1 to 24 hours.

Compounds of the formula I, where P is a suitable protecting group as defined in Green and Wuts, supra, are either commercially available, known, or may be prepared from commercially available starting materials by methods known to those of ordinary skill in the art.

Scheme 6 describes the preparation of compounds of the formula XVIII, wherein X is —OCH$_2$—, SCH$_2$— or —N(R$^{10}$)CH$_2$—. Compounds of the formula XVIII are compounds of formula IV in Scheme 1, wherein R$^1$ is hydrogen. Referring to Scheme 6, compounds of formula XVIII can be prepared by treatment of a compound of formula XIX with a compound of formula G—B—Y—A—XH, wherein X is O, S or NR$^{10}$, in the presence of a suitable base, such as an alkali metal hydride base, preferable sodium hydride, and a suitable solvent, such as an alcoholic solvent, THF or DMF at a temperature of about −20 to 50° C., preferably about 0° C. to 23° C. for about 1 to 24 hours.

The compounds of the formula I, which are basic in nature, are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts.

Those compounds of the formula I which are also acidic in nature, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the herein described acidic compounds of formula I. These non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure.

Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum product yields.

BIOLOGICAL ASSAYS

The ability of the compounds of formula I or their pharmaceutically acceptable salts (hereinafter also referred to as the compounds of the present invention) to inhibit metalloproteinases or mammalian reprolysins and, consequently, demonstrate their effectiveness for treating diseases characterized by metalloproteinase activity is shown by the following in vitro and in vivo assay tests.

MMP Assays

MMP-13 selective inhibitors can be identified by screening the inhibitors of the present invention through the MMP fluorescence assays described below and selecting those agents with MMP-13/MMP-X inhibition IC$_{50}$ ratios of 100 or greater and potency of less than 100 nM, where MMP-X refers to one or more other MMP's.

Non-selective collagenase inhibitors as used herein, unless otherwise mentioned, refer to agents which exhibit less than a 100 fold selectivity for the inhibition of MMP-13 enzyme activity over MMP-X enzyme activity or a potency of more than 100 nM as defined by the IC$_{50}$ results from the MMP-13/MMP-X fluorescence assays described below.

The ability of collagenase inhibitors to inhibit collagenase activity is well known in the art. The degree of inhibition of a particular MMP for several compounds has been well documented in the art and those skilled in the art will know how to normalize different assay results to those assays reported herein. The following assays may be used to identify matrix metalloproteinase inhibitors.

Inhibition of Human Collagenase (MMP-1)

Human recombinant collagenase is activated with trypsin. The amount of trypsin is optimized for each lot of collagenase-1 but a typical reaction uses the following ratio: 5 μg trypsin per 100 μg of collagenase. The trypsin and collagenase are incubated at room temperature for 10 minutes then a five fold excess (50 mg/10 mg trypsin) of soybean trypsin inhibitor is added.

Stock solutions (10 mM) of inhibitors are made up in dimethylsulfoxide and then diluted using the following scheme:

10 mM→120 μM→12 μM→1.2 μM→0.12 μM

Twenty-five microliters of each concentration is then added in triplicate to appropriate wells of a 96 well microfluor plate. The final concentration of inhibitor will be a 1:4 dilution after addition of enzyme and substrate. Positive controls (enzyme, no inhibitor) are set up in wells D7–D12 and negative controls (no enzyme, no inhibitors) are set in wells D1–D6.

Collagenase-1 is diluted to 240 ng/ml and 25 μl is then added to appropriate wells of the microfluor plate. Final concentration of collagenase in the assay is 60 ng/ml.

Substrate (DNP-Pro-Cha-Gly-Cys(Me)-His-Ala-Lys (NMA)—NH$_2$) is made as a 5 mM stock in dimethylsulfoxide and then diluted to 20 μM in assay buffer. The assay is initiated by the addition of 50 μl substrate per well of the microfluor plate to give a final concentration of 10 μM.

Fluorescence readings (360 nM excitation, 460 nm emission) are taken at time 0 and then at 20 minute intervals.

The assay is conducted at room temperature with a typical assay time of 3 hours.

Fluorescence versus time is then plotted for both the blank and collagenase containing samples (data from triplicate determinations is averaged). A time point that provides a good signal (at least five fold over the blank) and that is on a linear part of the curve (usually around 120 minutes) is chosen to determine $IC_{50}$ values. The zero time is used as a blank for each compound at each concentration and these values are subtracted from the 120 minute data. Data is plotted as inhibitor concentration versus % control (inhibitor fluorescence divided by fluorescence of collagenase alone× 100). $IC_{50}$'s are determined from the concentration of inhibitor that gives a signal that is 50% of the control.

If $IC_{50}$'s are reported to be less than 0.03 μM then the inhibitors are assayed at concentrations of 0.3 μM, 0.03 μM, and 0.003 μM.

Inhibition of Gelatinase (MMP-2)

Human recombinant 72 kD gelatinase (MMP-2, gelatinase A) is activated for 16–18 hours with 1 mM p-aminophenyl-mercuric acetate (from a freshly prepared 100 mM stock in 0.2 N NaOH) at 4° C., rocking gently.

10 mM dimethylsulfoxide stock solutions of inhibitors are diluted serially in assay buffer (50 mM TRIS, pH 7.5, 200 mM NaCl, 5 mM $CaCl_2$, 20 μM $ZnCl_2$ and 0.02% BRIJ-35 (vol./vol.)) using the following scheme:

10 mM→120 μM→12 μM→1.2 μM→0.12 μM

Further dilutions are made as necessary following this same scheme. A minimum of four inhibitor concentrations for each compound are performed in each assay. 25 μL of each concentration is then added to triplicate wells of a black 96 well U-bottomed microfluor plate. As the final assay volume is 100 μL, final concentrations of inhibitor are the result of a further 1:4 dilution (i.e. 30 μM→3 μM→0.3 μM→0.03 μM, etc.). A blank (no enzyme, no inhibitor) and a positive enzyme control (with enzyme, no inhibitor) are also prepared in triplicate.

Activated enzyme is diluted to 100 ng/mL in assay buffer, 25 μL per well is added to appropriate wells of the microplate. Final enzyme concentration in the assay is 25 ng/mL (0.34 nM).

A five mM dimethylsulfoxide stock solution of substrate (Mca-Pro-Leu-Gly-Leu-Dpa-Ala-Arg-$NH_2$) is diluted in assay buffer to 20 μM. The assay is initiated by addition of 50 μL of diluted substrate yielding a final assay concentration of 10 μM substrate. At time zero, fluorescence reading (320 excitation; 390 emission) is immediately taken and subsequent readings are taken every fifteen minutes at room temperature with a PerSeptive Biosystems CytoFluor Multi-Well Plate Reader with the gain at 90 units.

The average value of fluorescence of the enzyme and blank are plotted versus time. An early time point on the linear part of this curve is chosen for $IC_{50}$ determinations. The zero time point for each compound at each dilution is subtracted from the latter time point and the data then expressed as percent of enzyme control (inhibitor fluorescence divided by fluorescence of positive enzyme control× 100). Data is plotted as inhibitor concentration versus percent of enzyme control. $IC_{50}$'s are defined as the concentration of inhibitor that gives a signal that is 50% of the positive enzyme control.

Inhibition of Stromelysin Activity (MMP-3)

Human recombinant stromelysin (MMP-3, stromelysin-1) is activated for 20–22 hours with 2 mM p-aminophenyl-mercuric acetate (from a freshly prepared 100 mM stock in 0.2 N NaOH) at 37° C.

10 mM dimethylsulfoxide stock solutions of inhibitors are diluted serially in assay buffer (50 mM TRIS, pH 7.5, 150 mM NaCl, 10 mM $CaCl_2$ and 0.05% BRIJ-35 (vol./vol.)) using the following scheme:

10 mM→120 μM→12 μM→1.2 μM→0.12 μM

Further dilutions are made as necessary following this same scheme. A minimum of four inhibitor concentrations for each compound are performed in each assay. 25 μL of each concentration is then added to triplicate wells of a black 96 well U-bottomed microfluor plate. As the final assay volume is 100 μL, final concentrations of inhibitor are the result of a further 1:4 dilution (i.e. 30 μM→3 μM→0.3 μM→0.03 μM, etc.). A blank (no enzyme, no inhibitor) and a positive enzyme control (with enzyme, no inhibitor) are also prepared in triplicate.

Activated enzyme is diluted to 200 ng/mL in assay buffer, 25 μL per well is added to appropriate wells of the microplate. Final enzyme concentration in the assay is 50 ng/mL (0.875 nM).

A ten mM dimethylsulfoxide stock solution of substrate (Mca-Arg-Pro-Lys-Pro-Val-Glu-Nva-Trp-Arg-Lys(Dnp)-$NH_2$) is diluted in assay buffer to 6 μM. The assay is initiated by addition of 50 μL of diluted substrate yielding a final assay concentration of 3 μM substrate. At time zero, fluorescence reading (320 excitation; 390 emission) is immediately taken and subsequent readings are taken every fifteen minutes at room temperature with a PerSeptive Biosystems CytoFluor Multi-Well Plate Reader with the gain at 90 units.

The average value of fluorescence of the enzyme and blank are plotted versus time. An early time point on the linear part of this curve is chosen for $IC_{50}$ determinations. The zero time point for each compound at each dilution is subtracted from the latter time point and the data then expressed as percent of enzyme control (inhibitor fluorescence divided by fluorescence of positive enzyme control× 100). Data is plotted as inhibitor concentration versus percent of enzyme control. $IC_{50}$'s are defined as the concentration of inhibitor that gives a signal that is 50% of the positive enzyme control.

Inhibition of Human 92 kD Gelatinase (MMP-9)

Inhibition of 92 kD gelatinase (MMP-9) activity is assayed using the Mca-Pro-Leu-Gly-Leu-Dpa-Ala-Arg-$NH_2$ substrate (10 μM) under similar conditions as described above for the inhibition of human collagenase (MMP-1).

Human recombinant 92 kD gelatinase (MMP-9, gelatinase B) is activated for 2 hours with 1 mM p-aminophenyl-mercuric acetate (from a freshly prepared 100 mM stock in 0.2 N NaOH) at 37 C.

10 mM dimethylsulfoxide stock solutions of inhibitors are diluted serially in assay buffer (50 mM TRIS, pH 7.5, 200 mM NaCl, 5 mM $CaCl_2$, 20 μM $ZnCl_2$, 0.02% BRIJ-35 (vol./vol.)) using the following scheme:

10 mM→120 μM→12 μM→1.2 μM→0.12 μM

Further dilutions are made as necessary following this same scheme. A minimum of four inhibitor concentrations for each compound are performed in each assay. 25 μL of each concentration is then added to triplicate wells of a black 96 well U-bottomed microfluor plate. As the final assay volume is 100 μL, final concentrations of inhibitor are the result of a further 1:4 dilution (i.e. 30 μM→3 μM→0.3 μM→0.03

μM, etc.). A blank (no enzyme, no inhibitor) and a positive enzyme control (with enzyme, no inhibitor) are also prepared in triplicate.

Activated enzyme is diluted to 100 ng/mL in assay buffer, 25 μL per well is added to appropriate wells of the microplate. Final enzyme concentration in the assay is 25 ng/mL (0.27 nM).

A five mM dimethylsulfoxide stock solution of substrate (Mca-Pro-Leu-Gly-Leu-Dpa-Ala-Arg-$NH_2$) is diluted in assay buffer to 20 μM. The assay is initiated by addition of 50 μL of diluted substrate yielding a final assay concentration of 10 μM substrate. A 0 time fluorescence reading (320 excitation; 390 emission) is immediately taken and subsequent readings are taken every fifteen minutes at room temperature with a PerSeptive Biosystems CytoFluor Multi-Well Plate Reader with the gain at 90 units.

The average value of fluorescence of the enzyme and blank are plotted versus time. An early time point on the linear part of this curve is chosen for $IC_{50}$ determinations. The 0 time point for each compound at each dilution is subtracted from the latter time point and the data then expressed as percent of enzyme control (inhibitor fluorescence divided by fluorescence of positive enzyme control× 100). Data is plotted as inhibitor concentration versus percent of enzyme control. $IC_{50}$'s are defined as the concentration of inhibitor that gives a signal that is 50% of the positive enzyme control.

Inhibition of MMP-13

Human recombinant MMP-13 is activated with 2 mM APMA (p-aminophenyl mercuric acetate) for 1.5 hours, at 37° C. and is diluted to 400 mg/ml in assay buffer (50 mM Tris, pH 7.5, 200 mM sodium chloride, 5 mM calcium chloride, 20 μM zinc chloride, 0.02% brij). Twenty-five microliters of diluted enzyme is added per well of a 96 well microfluor plate. The enzyme is then diluted in a 1:4 ratio in the assay by the addition of inhibitor and substrate to give a final concentration in the assay of 100 mg/ml.

10 mM stock solutions of inhibitors are made up in dimethyl sulfoxide and then diluted in assay buffer as per the inhibitor dilution scheme for inhibition of human collagenase (MMP-1): Twenty-five microliters of each concentration is added in triplicate to the microfluor plate. The final concentrations in the assay are 30 μM, 3 μM, 0.3 μM, and 0.03 μM.

Substrate (Dnp-Pro-Cha-Gly-Cys(Me)-His-Ala-Lys (NMA)-$NH_2$) is prepared as for inhibition of human collagenase (MMP-1) and 50 μl is added to each well to give a final assay concentration of 10 μM. Fluorescence readings (360 nM excitation; 450 emission) are taken at time 0 and every 5 minutes for 1 hour.

Positive controls consist of enzyme and substrate with no inhibitor and blanks consist of substrate only.

$IC_{50}$'s are determined as per inhibition of human collagenase (MMP-1). If $IC_{50}$'s are reported to be less than 0.03 μM, inhibitors are then assayed at final concentrations of 0.3 μM, 0.03 μM, 0.003 μM and 0.0003 μM.

Collagen Film MMP-13 Assay

Rat type I collagen is radiolabeled with $^{14}C$ acetic anhydride (T. E. Cawston and A. J. Barrett, *Anal. Biochem.*, 99, 340–345 (1979)) and used to prepare 96 well plates containing radiolabeled collagen films (Barbara Johnson-Wint, *Anal. Biochem.*, 104, 175–181 (1980)). When a solution containing collagenase is added to the well, the enzyme cleaves the insoluble collagen which unwinds and is thus solubilized. Collagenase activity is directly proportional to the amount of collagen solubilized, determined by the proportion of radioactivity released into the supernatant as measured in a standard scintillation counter. Collagenase inhibitors are, therefore, compounds which reduce the radioactive counts released with respect to the controls with no inhibitor present. One specific embodiment of this assay is described in detail below.

For determining the selectivity of compounds for MMP-13 versus MMP-1 using collagen as a substrate, the following procedure is used. Recombinant human proMMP-13 or proMMP-1 is activated according to the procedures outlined above. The activated MMP-13 or MMP-1 is diluted to 0.6 ug/ml with buffer (50 mM Tris pH 7.5, 150 mM NaCl, 10 mM $CaCl_2$, 1 uM $ZnCl_2$, 0.05% Brij-35, 0.02% sodium azide).

Stock solutions of test compound (10 mM) in dimethylsulfoxide are prepared. Dilutions of the test compounds in the Tris buffer, above, are made to 0.2, 2.0, 20, 200, 2000 and 20000 nM.

100 μl of appropriate drug dilution and 100 μl of diluted enzyme are pipetted into wells of a 96 well plate containing collagen films labeled with $^{14}C$-collagen. The final enzyme concentration is 0.3 μg/ml while the final drug concentration is 0.1, 1.0, 10, 100, 1000 nM. Each drug concentration and control is analyzed in triplicate. Triplicate controls are also run for the conditions in which no enzyme is present and for enzyme in the absence of any compound.

The plates are incubated at 37° C. for a time period such that around 30–50% of the available collagen is solubilized—determined by counting additional control wells at various time points. In most cases around 9 hours of incubation are required. When the assay has progressed sufficiently, the supernatant from each well is removed and counted in a scintillation counter. The background counts (determined by the counts in the wells with no enzyme) are subtracted from each sample and the % release calculated in relation to the wells with enzyme only and no inhibitor. The triplicate values for each point are averaged and the data graphed as percent release versus drug concentration. $IC_{50}$'s are determined from the point at which 50% inhibition of release of radiolabeled collagen is obtained.

To determine the identity of the active collagenases in cartilage conditioned medium, assays were carried out using collagen as a substrate, cartilage conditioned medium containing collagenase activity and inhibitors of varying selectivity. The cartilage conditioned medium was collected during the time at which collagen degradation was occurring and thus is representative of the collagenases responsible for the collagen breakdown. Assays were carried out as outlined above except that instead of using recombinant MMP-13 or recombinant MMP-1, cartilage conditioned medium was the enzyme source.

IL-1 Induced Cartilage Collagen Degradation from Bovine Nasal Cartilage

This assay uses bovine nasal cartilage explants which are commonly used to test the efficacy of various compounds to inhibit either IL-1 induced proteoglycan degradation or IL-1 induced collagen degradation. Bovine nasal cartilage is a tissue that is very similar to articular cartilage, i.e. chondrocytes surrounded by a matrix that is primarily type 11 collagen and aggrecan. The tissue is used because it: (1) is very similar to articular cartilage, (2) is readily available, (3) is relatively homogeneous, and (4) degrades with predictable kinetics after IL-1 stimulation.

Two variations of this assay have been used to assay compounds. Both variations give similar data. The two variations are described below:

Variation 1

Three plugs of bovine nasal cartilage (approximately 2 mm diameter×1.5 mm long) are placed into each well of a 24 well tissue culture plate. One ml of serumless medium is then added to each well. Compounds are prepared as 10 mM stock solutions in DMSO and then diluted appropriately in serumless medium to final concentrations, e.g., 50, 500 and 5000 nM. Each concentration is assayed in triplicate.

Human recombinant IL-1α (5 ng/mL) (IL-1) is added to triplicate control wells and to each well containing drug. Triplicate control wells are also set up in which neither drug nor IL-1 are added. The medium is removed and fresh medium containing IL-1 and the appropriate drug concentrations is added on days 6, 12, 18 and 24 or every 3–4 days if necessary. The media removed at each time point is stored at −20° C. for later analysis. When the cartilage in the IL-1 alone wells has almost completely resorbed (about day 21), the experiment is terminated. The medium, is removed and stored. Aliquots (100 ul) from each well at each time point are pooled, digested with papain and then analyzed for hydroxyproline content. Background hydroxyproline (average of wells with no IL-1 and no drug) is subtracted from each data point and the average calculated for each triplicate. The data is then expressed as a percent of the IL-1 alone average value and plotted. The $IC_{50}$ is determined from this plot.

Variation 2

The experimental set-up is the same as outlined above in Variation 1, until day 12. On day 12, the conditioned medium from each well is removed and frozen. Then one ml of phosphate buffered saline (PBS) containing 0.5 $\mu$g/ml trypsin is added to each well and incubation continued for a further 48 hours at 37° C. After 48 hours incubation in trypsin, the PBS solution is removed. Aliquots (50 $\mu$l) of the PBS/trypsin solution and the previous two time points (days 6 and 12) are pooled, hydrolyzed and hydroxyproline content determined. Background hydroxyproline (average of wells with no IL-1 and no drug) is subtracted from each data point and the average calculated for each triplicate. The data is then expressed as a percent of the IL-1 alone average value and plotted. The $IC_{50}$ is determined from this plot. In this variation, the time course of the experiment is shortened considerably. The addition of trypsin for 48 hours after 12 days of IL-1 stimulation likely releases any type II collagen that has been damaged by collagenase activity but not yet released from the cartilage matrix. In the absence of IL-1 stimulation, trypsin treatment produces only low background levels of collagen degradation in the cartilage explants.

Inhibition of TNF Production

The ability or inability of the compounds or the pharmaceutically acceptable salts thereof to inhibit the production of TNF is shown by the following in vitro assay:

Human Monocyte Assay

Human mononuclear cells were isolated from anticoagulated human blood using a one-step Ficoll-hypaque separation technique. (2) The mononuclear cells were washed three times in Hanks balanced salt solution (HBSS) with divalent cations and resuspended to a density of $2\times10^6$/ml in HBSS containing 1% BSA. Differential counts determined using the Abbott Cell Dyn 3500 analyzer indicated that monocytes ranged from 17 to 24% of the total cells in these preparations.

180 $\mu$l of the cell suspension was aliquoted into flat bottom 96 well plates (Costar). Additions of compounds and LPS (100 ng/ml final concentration) gave a final volume of 200 $\mu$l. All conditions were performed in triplicate. After a four hour incubation at 37° C. in an humidified $CO_2$ incubator, plates were removed and centrifuged (10 minutes at approximately 250× g) and the supernatants removed and assayed for TNF α using the R&D ELISA Kit.

Aggrecanase Assay

Primary porcine chondrocytes from articular joint cartilage are isolated by sequential trypsin and collagenase digestion followed by collagenase digestion overnight and are plated at $2\times10^5$ cells per well into 48 well plates with 5 $\mu$Ci/ml $^{35}$S (1000 Ci/mmol) sulphur in type I collagen coated plates. Cells are allowed to incorporate label into their proteoglycan matrix (approximately 1 week) at 37° C., under an atmosphere of 5% $CO_2$.

The night before initiating the assay, chondrocyte monolayers are washed two times in DMEM/1% PSF/G and then allowed to incubate in fresh DMEM/1% FBS overnight.

The following morning chondrocytes are washed once in DMEM/1% PSF/G. The final wash is allowed to sit on the plates in the incubator while making dilutions.

Media and dilutions can be made as described in the Table below.

| | |
|---|---|
| Control Media | DMEM alone (control media) |
| IL-1 Media | DMEM + IL-1 (5 ng/ml) |
| Drug Dilutions | Make all compounds stocks at 10 mM in DMSO. Make a 100 uM stock of each compound in DMEM in 96 well plate. Store in freezer overnight. The next day perform serial dilutions in DMEM with IL-1 to 5 uM, 500 nM, and 50 nM. Aspirate final wash from wells and add 50 ul of compound from above dilutions to 450 ul of IL-1 media in appropriate wells of the 48 well plates. Final compound concentrations equal 500 nM, 50 nM, and 5 nM. All samples completed in triplicate with Control and IL-1 alone samples on each plate. |

Plates are labeled and only the interior 24 wells of the plate are used. On one of the plates, several columns are designated as IL-1 (no drug) and Control (no IL-1, no drug). These control columns are periodically counted to monitor 35S-proteoglycan release. Control and IL-1 media are added to wells (450 ul) followed by compound (50 ul) so as to initiate the assay. Plates are incubated at 37° C., with a 5% $CO_2$ atmosphere.

At 40–50% release (when CPM from IL-1 media is 4–5 times control media) as assessed by liquid scintillation counting (LSC) of media samples, the assay is terminated (9–12 hours). Media is removed from all wells and placed in scintillation tubes. Scintillate is added and radioactive counts are acquired (LSC). To solubilize cell layers, 500 ul of papain digestion buffer (0.2 M Tris, pH 7.0, 5 mM EDTA, 5 mM DTT, and 1 mg/ml papain) is added to each well. Plates with digestion solution are incubated at 60° C. overnight. The cell layer is removed from the plates the next day and placed in scintillation tubes. Scintillate is then added, and samples counted (LSC).

The percent of released counts from the total present in each well is determined.

Averages of the triplicates are made with control background subtracted from each well. The percent of compound inhibition is based on IL-1 samples as 0% inhibition (100% of total counts).

The compounds of the present invention that were tested all have $IC_{50}$'s in at least one of the above assays of less than 100 µM preferably less than 100 nM. Certain preferred groups of compounds possess differential selectivity toward the various MMP's or ADAMs. One group of preferred compounds possess selective activity towards MMP-13 over MMP-1. Another preferred group of compounds possess selective activity towards MMP-13 over MMP-1 and MMP-12.

For administration to mammals, including humans, for the inhibition of matrix metalloproteinases or mammalian reprolysin, a variety of conventional routes may be used including oral, parenteral (e.g., intravenous, intramuscular or subcutaneous), buccal, anal and topical. In general, the compounds of the invention (hereinafter also known as the active compounds) will be administered at dosages between about 0.1 and 25 mg/kg body weight of the subject to be treated per day, preferably from about 0.3 to 5 mg/kg. Preferably the active compound will be administered orally or parenterally. However, some variation in dosage will necessarily occur depending on the condition of the subject being treated. The person responsible for administration will, in any event, determine the appropriate dose for the individual subject.

The compounds of the present invention can be administered in a wide variety of different dosage forms, in general, the therapeutically effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelation and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof. In the case of animals, they are advantageously contained in an animal feed or drinking water in a concentration of 5–5000 ppm, preferably 25 to 500 ppm.

For parenteral administration (intramuscular, intraperitoneal, subcutaneous and intravenous use) a sterile injectable solution of the active ingredient is usually prepared. Solutions of a therapeutic compound of the present invention in either sesame or peanut oil or in aqueous propylene glycol may be employed. The aqueous solutions should be suitably adjusted and buffered, preferably at a pH of greater than 8, if necessary and the liquid diluent first rendered isotonic. These aqueous solutions are suitable intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art. In the case of animals, compounds can be administered intramuscularly or subcutaneously at dosage levels of about 0.1 to 50 mg/kg/day, advantageously 0.2 to 10 mg/kg/day given in a single dose or up to 3 divided doses.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

For topical ocular administration, direct application to the affected eye may be employed in the form of a formulation as eyedrops, aerosol, gels or ointments, or can be incorporated into collagen (such as poly-2-hydroxyethylmethacrylate and co-polymers thereof), or a hydrophilic polymer shield. The materials can also be applied as a contact lens or via a local reservoir or as a subconjunctival formulation.

For intraorbital administration a sterile injectable solution of the active ingredient is usually prepared. Solutions of a therapeutic compound of the present invention in an aqueous solution or suspension (particle size less than 10 micron) may be employed. The aqueous solutions should be suitably adjusted and buffered, preferably at a pH between 5 and 8, if necessary and the liquid diluent first rendered isotonic. Small amounts of polymers can be added to increase viscosity or for sustained release (such as cellulosic polymers, Dextran, polyethylene glycol, or alginic acid). These solutions are suitable for intraorbital injection purposes. The preparation of all these solutions under sterile conditions is readily accomplished by standard pharmaceutical techniques well known to those skilled in the art. In the case of animals, compounds can be administered intraorbitally at dosage levels of about 0.1 to 50 mg/kg/day, advantageously 0.2 to 10 mg/kg/day given in a single dose or up to 3 divided doses.

As with the other routes of administration and corresponding dosage forms described herein, dosage forms intended for oral administration are also suitably formulated to provide controlled-, sustained-, and/or delayed release of the active ingredient. Typically, these would include delayed-release oral tablets, capsules and multiparticulates, as well as enteric-coated tablets and capsules which prevent release and adsorption of the active ingredient in the stomach of the patient and facilitate enteric delivery distal to the stomach, i.e., in the intestine. Other typical oral dosage forms would include sustained-release oral tablets, capsules, and multiparticulates which provide systemic delivery of the active ingredient in a controlled manner over a prolonged period of time, e.g., a 24-hour period. Where rapid delivery of the active ingredient is required or desirable, a controlled-release oral dosage form may be prepared in the form of a fast-dissolving tablet, which would also preferably include highly soluble salt forms of the active ingredient.

The following Examples illustrate the preparation of the compounds of the present invention. Melting points are uncorrected. NMR data are reported in parts per million (δ) and are referenced to the deuterium lock signal from the sample solvent (deuteriochloroform unless otherwise specified). Commercial reagents were utilized without further purification. THF refers to tetrahydrofuran. DMF refers to N,N-dimethylformamide. Chromatography refers to column chromatography performed using 32–63 mm silica gel and executed under nitrogen pressure (flash chromatography) conditions. Room or ambient temperature refers to 20–25° C. All non-aqueous reactions were run under a nitrogen atmosphere for convenience and to maximize yields. Concentration at reduced pressure or in vacuo means that a rotary evaporator was used.

EXAMPLE 1

5-(2-Ethoxy-ethyl)-5-[4-(4-[1,3,4,]oxadiazol-2-yl-phenoxy-phenoxy[-pyrimidine-2,4,6-trione

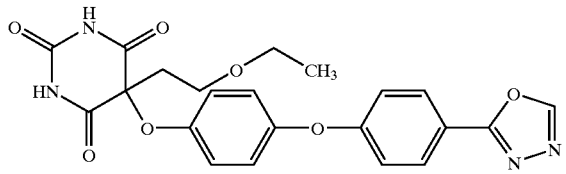

A mixture of 4-(4-[1,3,4]oxadiazol-2-yl-phenoxy)-phenol (0.90 g, 2.5 mmol), 5-Bromo-5-(2-ethoxy-ethyl)-pyrimidine-2,4,6-trione (1.0 g, 3.6 mmol), 1,5,7-trazabicyclo[4.4.0]dec-5-ene bound to polystyrene crosslinked with 2% DVB (PTBD, Fluka, 2.4 g, 6.1 mmol) and 11.7 mL of acetonitrile was shaken at 23° C. for 24 hours. The mixture was diluted with 30 mL of 25% acetic acid in methanol, filtered, and the solids were washed twice with methanol-acetic acid. The filtrate was concentrated in vacuo and purified by radial chromatography (2:1 to 1:1 hexane-ethyl acetate), affording 600 mg of 5-(2-Ethoxy-ethyl)-5-[4-(4-[1,3,4]oxadiazol-2-yl-phenoxy)-phenoxy]-pyrimidine-2,4,6-trione as a colorless solid.

$^1$H NMR (CD$_3$OD): 8.98 (s, 1H), 8.04 (d, 2H, J=9.0 Hz), 7.07 (d, 2H, J=9.5 Hz), 7.04 (d, 2H, J=9.0 Hz), 6.91 (d, 2H, J=9.0 Hz), 3.61 (t, 2H, J=5.5 Hz), 3.42 (q, 2H, J=7.0 Hz), 2.58 (t, 2H, J=6.5 Hz), 1.15 (t, 3H, J=7.5 Hz) ppm. MS (m/z, APCI): 496.3 [M−H]$^-$.

4-(4-[1,3,4]Oxadiazol-2-yl-phenoxy)-phenol

A mixture of 2-[4-(4-Methoxy-phenoxy)-phenyl]-[1,3,4] oxadiazole (1.1 g, 4.1 mmol), methionine (0.94 g, 4.9 mmol) and methanesulfonic acid (20.5 mL) was heated to 50° C. for 1.5 hours. The mixture was poured into ice cold 5M sodium hydroxide solution (60 mL), diluted with sodium bicarbonate solution (saturated aqueous), and was extracted three times into ethyl acetate. The combined organic phases were dried over sodium sulfate (Na$_2$SO$_4$), filtered and concentrated in vacuo, affording 4-(4-[1,3,4]oxadiazol-2-yl-phenoxy)-phenol as a colorless solid (0.91 g).

$^1$H NMR (CD$_3$OD): 8.97 (s, 1H), 8.01 (d, 2H, J=9.0 Hz), 7.04 (d, 2H, J=9.0 Hz), 6.97 (d, 2H, J=9.0 Hz), 6.87 (d, 2H, J=9.0 Hz) PPM.

2-[4-(4-Methoxy-phenoxy)-phenyl]-[1,3,4-]oxadiazole

A mixture of 4-methoxybenzeneboronic acid (1.9 g, 12 mmol), 4-(1,3,4)oxadiazol-2-yl-phenol (1.0 g, 6.2 mmol), copper(II)acetate (1.1 g, 6.2 mmol), crushed 4-Angstrom molecular sieves (0.65 g), triethylamine (4.2 mL) and methylene chloride (22.7 mL) was stirred under 1 atm of oxygen gas for 48 hours. The mixture was filtered through a pad of Celite®, concentrated in vacuo and purified by radial chromatography (2:1 hexane-ethyl acetate), affording 1.2 g of 2-[4-(4-Methoxy-phenoxy)-phenyl]-[1,3,4]oxadiazole.

$^1$H NMR (CDCl$_3$): 8.44 (s, 1H), 8.02 (d, 2H, J=9.0 Hz), 7.05 (m, 4H), 6.95 (d, 2H, J=7.0 Hz), 3.85 (s, 3H) ppm. MS (m/z, APCI): 300.2 [M+H]$^+$.

5-Bromo-5-(2-ethoxy-ethyl)-pyrimidine-2,4,6-trione

To a mixture of 5-(2-ethoxy-ethyl)-pyrimidine-2,4,6-trione (27.8 g, 139 mmol) and 1.5 L of water was added 1M sodium hydroxide solution (140 mL) and bromine (7.2 mL, 22.2 g, 139 mmol) at 0° C. After warming to room temperature, the mixture was stirred for 48 hours, filtered, and the solids were washed with water, then ether, then hexanes and dried in vacuo, affording 23 g of 5-bromo-5-(2-ethoxy-ethyl)-pyrimidine-2,4,6-trione.

$^1$H NMR (CDCl$_3$): 8.37 (bs, 2H), 3.53 (t, 2H, J=7.0 Hz), 3.35 (q, 2H, J=6.5 Hz), 2.99 (t, 2H, J=7.0 Hz), 1.05 (t, 3H, J=6.5 Hz) ppm. MS (m/z, APCI): 468.2 [M+H]$^+$.

5-(2-Ethoxy-ethyl)-pyrimidine-2,4,6-trione

Sodium metal (8.6 g, 0.38 mol) was added to ethanol (375 mL), and the mixture was stirred at ambient temperature until homogeneous. Diethyl malonate (60 g, 0.38 mol) was added, followed by bromoethyl ethyl ether (57.4 g, 0.38 mol). After stirring at reflux for 3 hours, the mixture was cooled to ambient temperature and concentrated in vacuo. The resulting material was added to a mixture of sodium ethoxide and ethanol (prepared by the reaction of 17.2 g of sodium metal with 600 mL of methanol). Urea (24 g) was added, and the resulting mixture was refluxed for 2.5 hours. After cooling to ambient temperature, the mixture was stirred for 12 hours, acidified with 1M hydrochloric acid solution, extracted three times with ethyl acetate, and the combined organic layers were dried over sodium sulfate (Na$_2$SO$_4$), filtered and concentrated in vacuo, affording 5-(2-ethoxy-ethyl)-pyrimidine-2,4,6-trione as a colorless solid.

EXAMPLE 2

N-(4-{4-[5-(2-Ethoxy-ethyl)-2,4,6trioxo-hexahydro-pyrimidin-5-yloxy]phenoxy}-benzyl)-propionamide

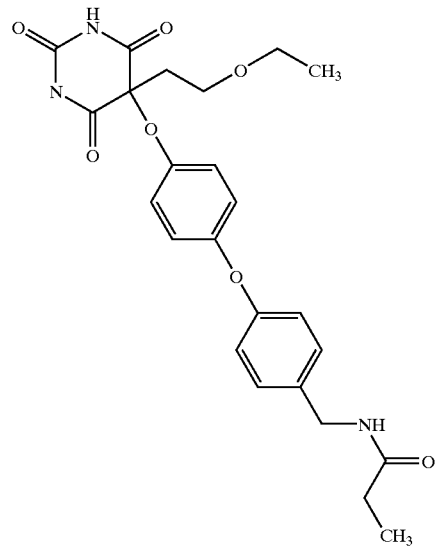

Following the procedure outlined for the preparation of Example 1, N-[4-(4-hydroxy-phenoxy)-benzyl]-propionamide (0.13 g, 0.47 mmol) was reacted with 5-bromo-5-(2-ethoxy-ethyl)-pyrimidine-2,4,6-trione (0.13 g, 0.48 mmol), 1,5,7-trazabicyclo[4.4.0]dec-5-ene bound to polystyrene crosslinked with 2% DVB (PTBD, Fluka, 0.31 g) and 1.55 mL of acetonitrile, benzyl)-propionamide (0.060 g) as a colorless solid.

$^1$H NMR (CD$_3$OD): 7.25 (d, 2H, J=8.5 Hz), 6.90 (m, 4H), 6.89 (d, 2H, J=8.0 Hz), 4.33 (s, 2H), 3.59 (t, 2H, J=6.0 Hz), 3.42 (q, 2H, J=7.0 Hz), 2.56 (t, 2H, J=6.5 Hz), 2.25 (q,2H, J=7.5 Hz), 1.14 (m, 6H) ppm. MS (m/z, APCI): 468.3 [M−H]$^-$.

N-[4-(4-Hydroxy-phenoxy)-benzyl]-propionamide

A mixture of 4-(4-Aminomethyl-phenoxy)-phenol (0.10 g, 0.47 mmol), MMP-resin (polystyrene bound N-methylmorpholine-type base, 0.30 g, 1.04 mmol) and 1.9 mL of acetonitrile was treated with propionyl chloride (0.086 mL, 1.0 mmol) and shaken for 24 hours at room temperature. After filtration of the resin, the filtrate was diluted with 2 mL of methanol and was treated with 2 mL of 1M lithium hydroxide (LiOH) in water. The mixture was shaken for 24 hours at room temperature, treated with Amberlite IRP-64® resin until neutral, filtered and concentrated in vacuo, affording N-[4-(4-Hydroxy-phenoxy)-benzyl]-propionamide. MS (m/z): 272.2 [M+H]$^+$.

EXAMPLE 3

4-{4-[5-(2-Ethoxy-ethyl)-2,4,6trioxo-hexahydro-pyrimidin-5-yloxy]phenoxy}-N-methyl-benzamide

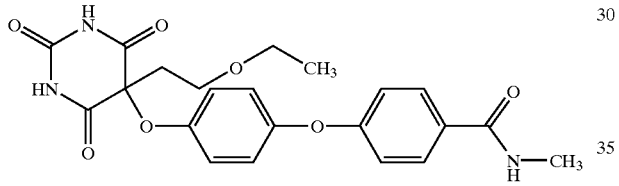

Following the procedure outlined for the preparation of Example 1 4-(4-hydroxy-phenoxy)-N-methyl-benzamide (0.14 g, 0.58 mmol) was reacted with 5-bromo-5-(2-ethoxy-ethyl)-pyrimidine-2,4,6-trione (0.16 g, 0.58 mmol), 1,5,7-trazabicyclo[4.4.0]dec-5-ene bound to polystyrene crosslinked with 2% DVB (PTBD, Fluka, 0.40 g) and 2.0 mL of acetonitrile, affording 4-{4-[5-(2-ethoxy-ethyl)-2,4, 6-trioxo-hexahydro-pyrimidin-5-yloxy]-phenoxy}-N-methyl-benzamide (0.040 g) as a colorless solid.

$^1$H NMR (CD$_3$OD): 7.79 (d, 2H, J=9.0 Hz), 7.00 (d, 2H, J=9.5 Hz), 6.95 (d, 2H, J=8.5 Hz), 6.90 (d, 2H, J=9.0 Hz), 3.61 (t, 2H, J=5.5 Hz), 3.42 (q, 2H, J=7.5 Hz), 2.91 (s, 3H), 2.57 (t, 2H, J=5.5 Hz), 1.14 (t, 3H, J=7.0 Hz) ppm. MS (m/z, APCI): 440.2 [M−H]$^-$.

1 4-(4-Hydroxy-Phenoxy)-N-methyl-benzamide

To a mixture of 4-(4-Hydroxy-phenoxy)-benzoic acid (0.25 g, 1.09 mmol), triethylamine (0.15 mL, 1.07 mmol) and tetrahydrofuran (THF) (5.0 mL) at 0° C. was added methylchloroformate (0.084 mL, 0.10 g, 1.1 mmol). After stirring for 15 minutes, excess methylamine was added via a sparge tube, and stirring was continued for 10 minutes. The mixture was diluted with water, extracted three times with ethyl acetate, and the combined organic phases were dried over Na$_2$SO$_4$, filtered and concentrated in vacuo, affording 1 4-(4-Hydroxy-phenoxy)-N-methyl-benzamide as a colorless syrup.

$^1$H NMR (CDCl$_3$): 7.70 (d, 2H, J=9.0 Hz), 6.87 (m, 6H), 2.96 (s, 3H) ppm. MS (m/z, APCI): 244.2 [M−H]$^-$.

EXAMPLE 4

5-[4-(4-Aminomethyl-phenoxy)-phenoxy]-5-(2-eyhoxy-ethyl)-pyrimidine-2,4,6-trione

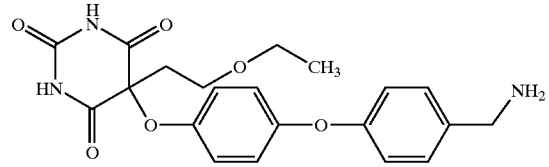

Following the procedure outlined for the preparation of Example 1, 4-(4-aminomethyl-phenoxy)-phenol (0.70 g, 3.32 mmol) was reacted with 5-bromo-5-(2-ethoxy-ethyl)-pyrimidine-2,4,6-trione (0.95 g, 2.4 mmol), 1,5,7-trazabicyclo[4.4.0]dec-5-ene bound to polystyrene crosslinked with 2% DVB (PTBD, Fluka, 2.22 9) and 11 mL of acetonitrile, affording 5-[4-(4-aminomethyl-phenoxy)-phenoxy]-5-(2-ethoxy-ethyl)-pyrimidine-2,4,6-trione (0.180 g) as a colorless solid after purification by reverse phase HPLC.

$^1$H NMR (CD$_3$OD): 7.41 (d, 2H, J=9.0 Hz), 7.00 (d, 2H, J=9.0 Hz), 6.95 (d, 2H, J=8.5 Hz), 6.87 (d, 2H, J=9.0 Hz), 4.08 (s, 2H), 3.60 (t, 2H, J=6.5 Hz), 3.42 (q, 2H, J=7.5 Hz), 2.57 (t, 2H, J=5.5 Hz), 1.14 (t, 3H, J=7.0 Hz) ppm. MS (m/z, APCI): 414.2 [M+H]$^+$.

EXAMPLE 5

N-(4-{5-[5-(2-Ethoxy-ethyl)-2,4,6trioxo-hexahydro-pyrimidin-5-yloxy]-pyridin-2-yloxy}-benzyl)-acetamide

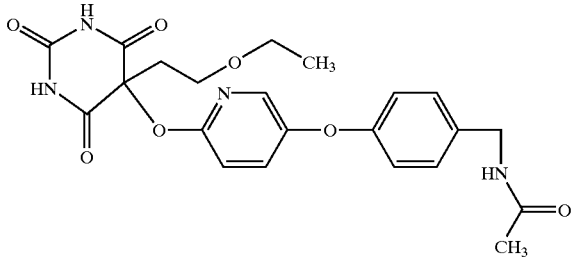

Following the procedure outlined for the preparation of Example 1, N-[4-(5-hydroxy-pyridin-2-yloxy)-benzyl]-acetamide (0.25 g, 0.97 mmol) when treated with 5-bromo-5-(2-ethoxy-ethyl)-pyrimidine-2,4,6-trione (0.20 g, 0.80 mmol), 1,5,7-trazabicyclo[4.4.0]dec-5-ene bound to polystyrene crosslinked with 2% DVB (PTBD, Fluka, 0.77 g) and 4 mL of acetonitrile, will afford N-(4-{5-[5-(2-Ethoxy-ethyl)-2,4,6-trioxo-hexahydro-pyrimidin-5-yloxy]-pyridin-2-yloxy}-benzyl)-acetamide. Expected MS (m/z, APCI): 455 [M−H]$^-$.

The following compounds were prepared according to the methods of Example 1, substituting the appropriate phenol (e.g. G—B—Y—A—OH) where appropriate.

TABLE 1

| EXAMPLE NUMBER | STRUCTURE | MOLECULAR WEIGHT | APCI MS [M + H]+ |
|---|---|---|---|
| 6 | 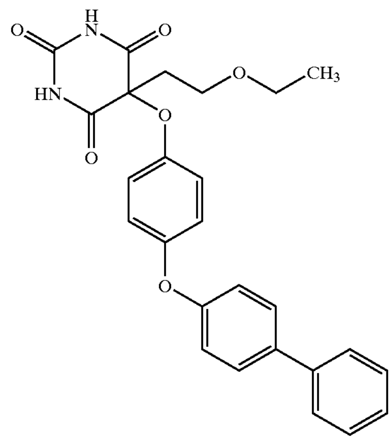 | 460.491 | |
| 7 | 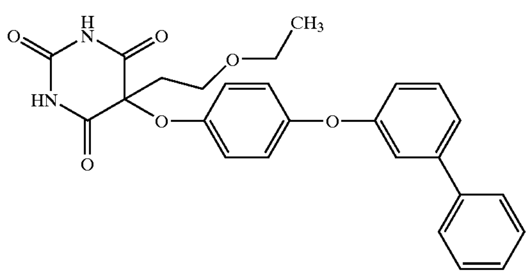 | 460.491 | 461.1 |
| 8 | 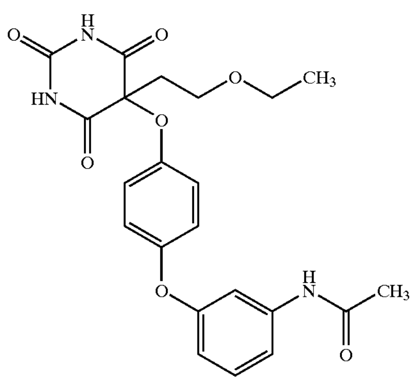 | 441.445 | 442.1 |
| 9 | 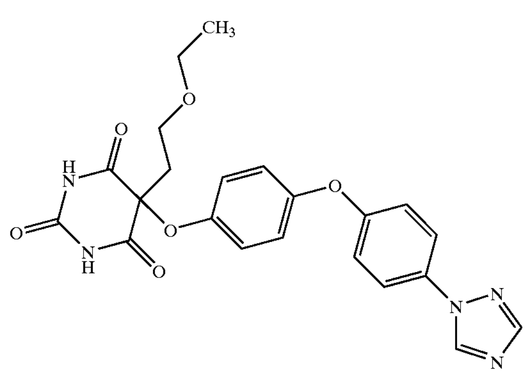 | 452.427 | 453.0 |

TABLE 1-continued

| EXAMPLE NUMBER | STRUCTURE | MOLECULAR WEIGHT | APCI MS [M + H]+ |
|---|---|---|---|
| 10 | 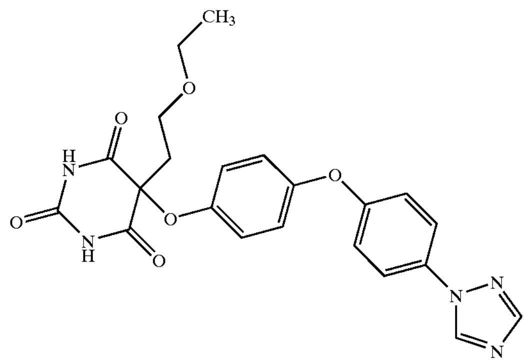 | 451.443 | 452.1 |
| 11 | 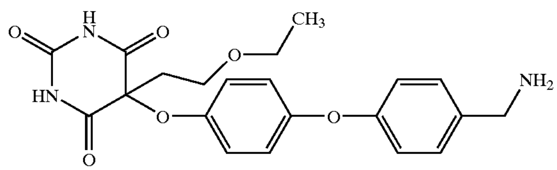 | 413 | 414.2 |
| 12 | 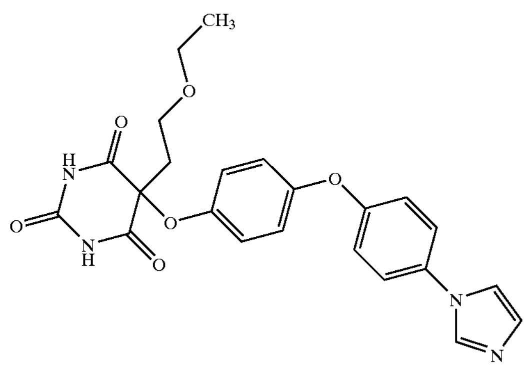 | 450.455 | 451.1 |
| 13 | 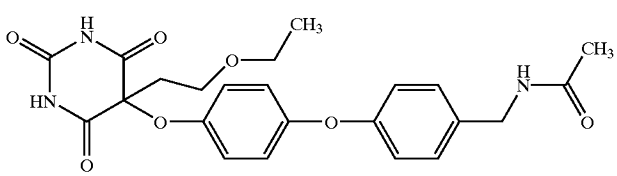 | 455.472 | 456.1 |
| 14 | 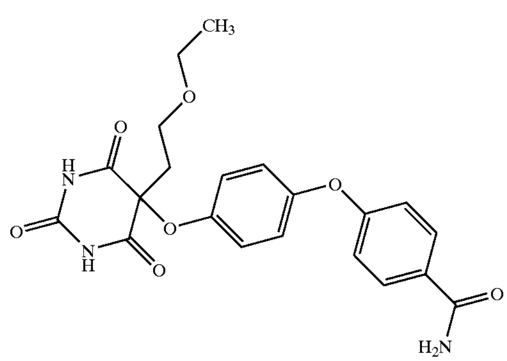 | 427.417 | 428.1 |

TABLE 1-continued

| EXAMPLE NUMBER | STRUCTURE | MOLECULAR WEIGHT | APCI MS [M + H]+ |
|---|---|---|---|
| 15 | 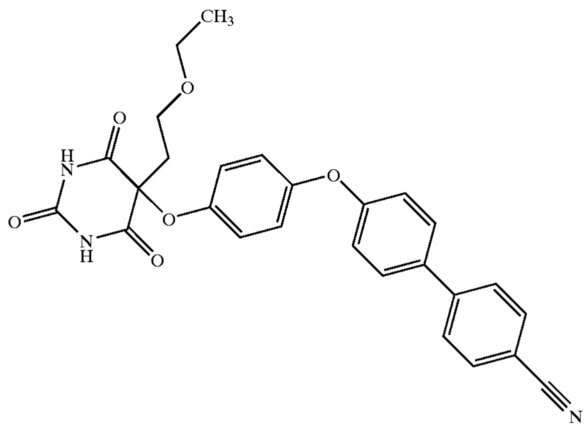 | 485.501 | 484.2 [M − H]− |
| 16 | 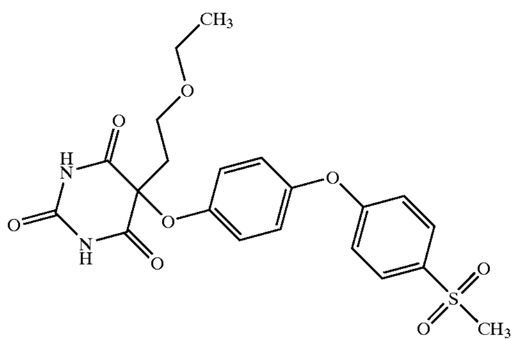 | 462.42 | 463.1 |
| 17 | 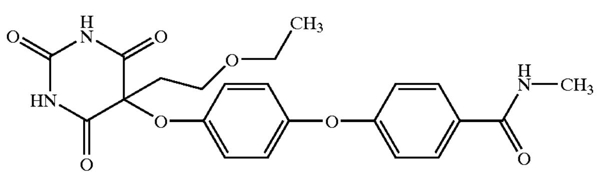 | 441.445 | 442.1 |
| 18 | 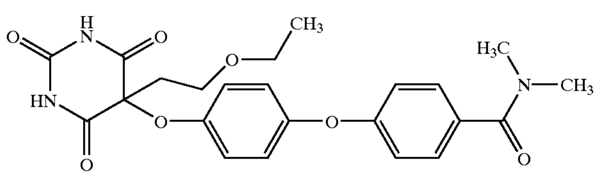 | 455.472 | 456.2 |
| 19 | 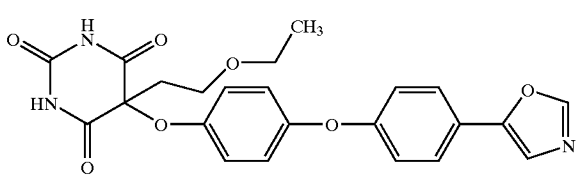 | 451.44 | 452.1 |
| 20 | 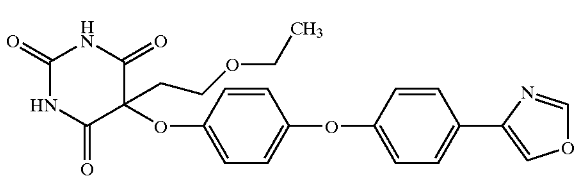 | 451.44 | 452.2 |

TABLE 1-continued
| EXAMPLE NUMBER | STRUCTURE | MOLECULAR WEIGHT | APCI MS [M + H]+ |
|---|---|---|---|
| 21 | 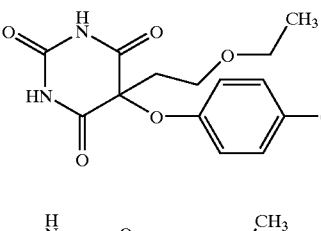 | 495.496 | 496.2 |
| 22 | 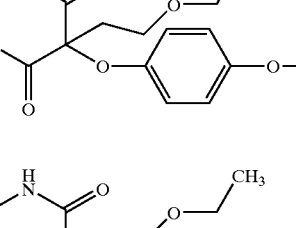 | 449.467 | 448.2 [M − H]⁻ |
| 23 | 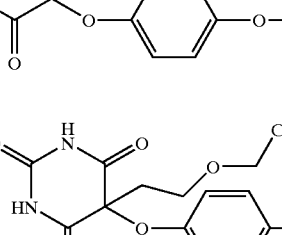 | 466.454 | 467.1 |
| 24 | 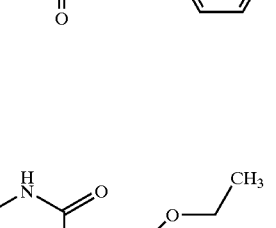 | 465.467 | 466.2 |
| 25 | 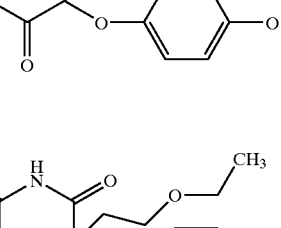 | 478.481 | |
| 26 | 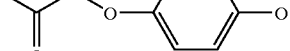 | 441.445 | 442.2 |
| 27 | 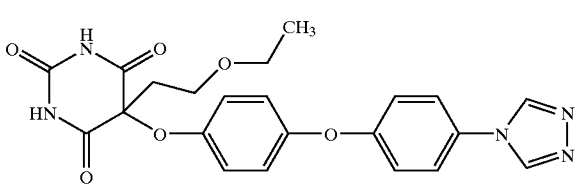 | 451.443 | 452.2 |

TABLE 1-continued

| EXAMPLE NUMBER | STRUCTURE | MOLECULAR WEIGHT | APCI MS [M + H]+ |
|---|---|---|---|
| 28 | 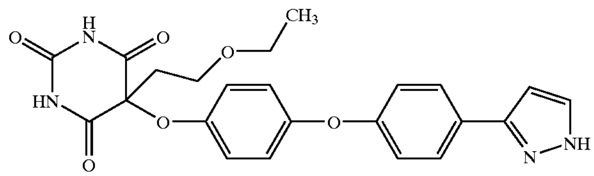 | 450.455 | 451.2 |
| 29 | 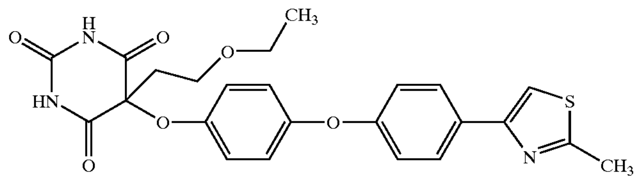 | 481.531 | 482.2 |
| 30 | 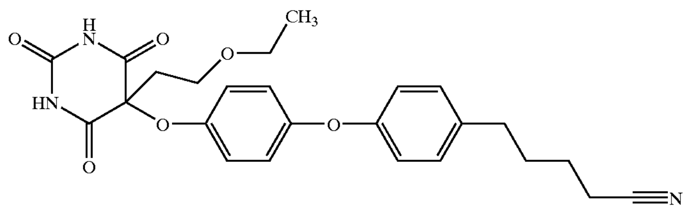 | 465.51 | 466.2 |
| 31 | 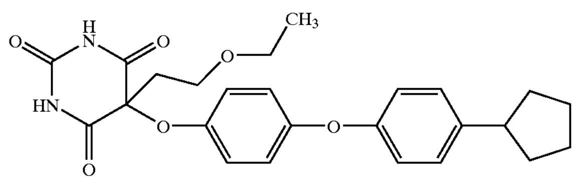 | 452.512 | 453.2 |
| 32 | 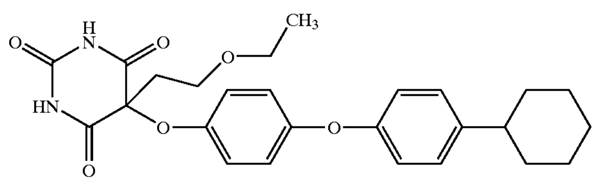 | 466.539 | 467.2 |
| 33 | 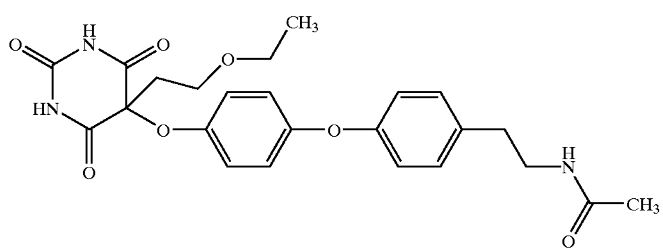 | 469.499 | 470.2 |
| 34 | 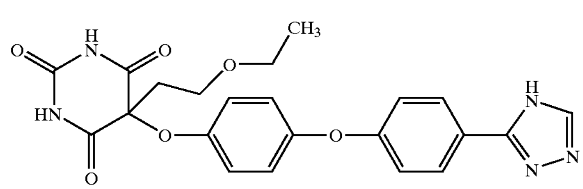 | 451.443 | 452.1 |

TABLE 1-continued

| EXAMPLE NUMBER | STRUCTURE | MOLECULAR WEIGHT | APCI MS [M + H]+ |
|---|---|---|---|
| 35 | 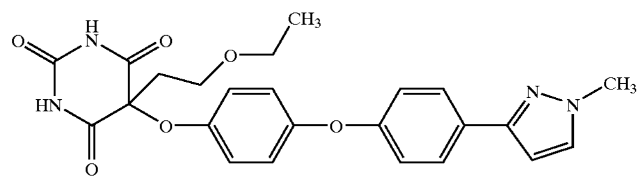 | 464.482 | 465.2 |
| 36 | 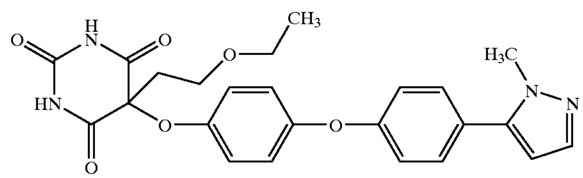 | 464.482 | 465.2 |
| 37 | 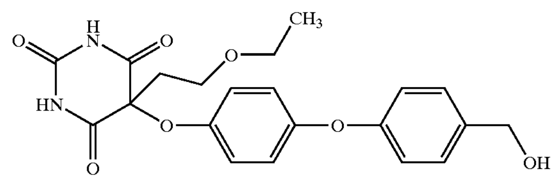 | 414.419 | 413.2 [M − H]− |
| 38 | 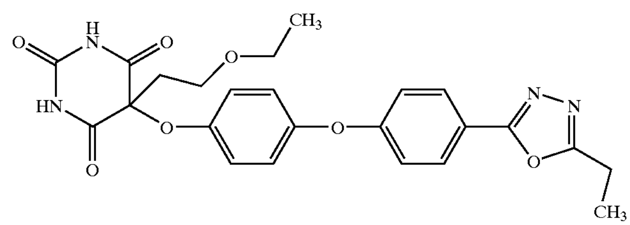 | 480.481 | 481.1 |
| 39 | 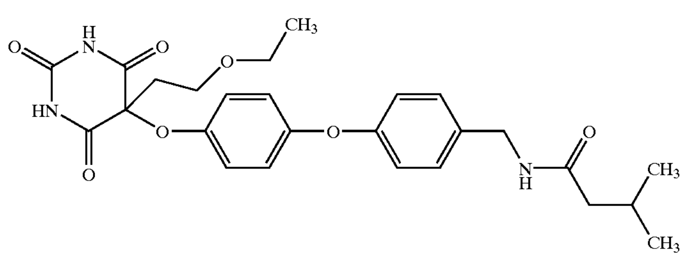 | 497.553 | 498.2 |
| 40 | 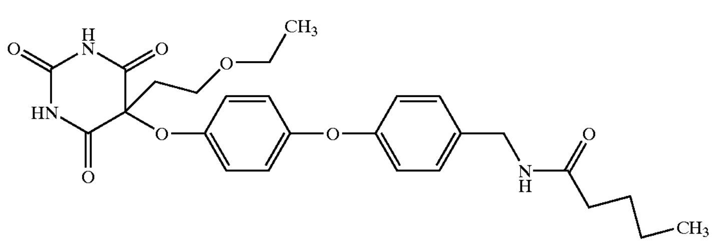 | 497.553 | 498.3 |
| 41 | 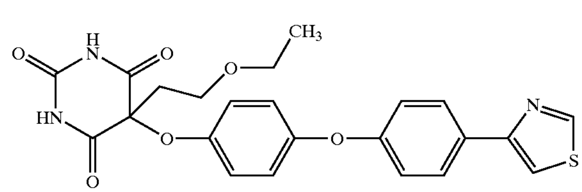 | 467.504 | 468.2 |

TABLE 1-continued

| EXAMPLE NUMBER | STRUCTURE | MOLECULAR WEIGHT | APCI MS [M + H]+ |
| --- | --- | --- | --- |
| 42 | 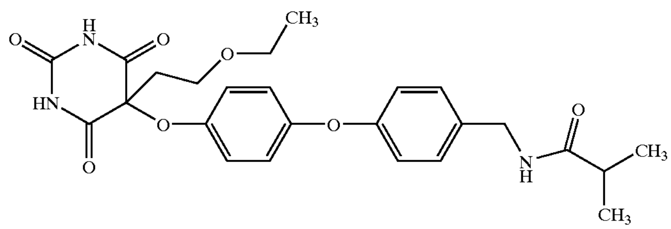 | 483.526 | 484.2 |
| 43 | 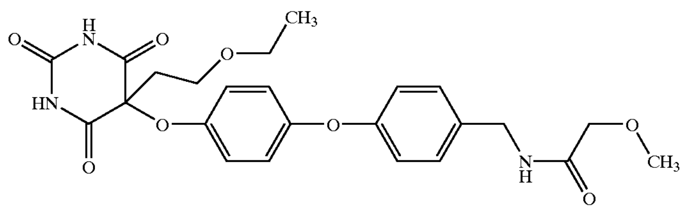 | 485.498 | 486.2 |
| 44 | 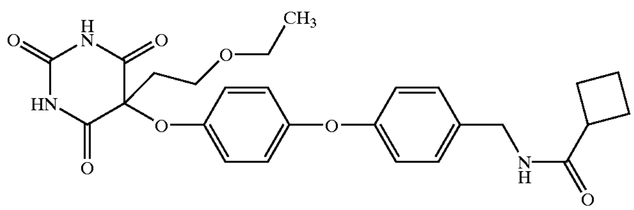 | 495.537 | 496.2 |
| 45 | 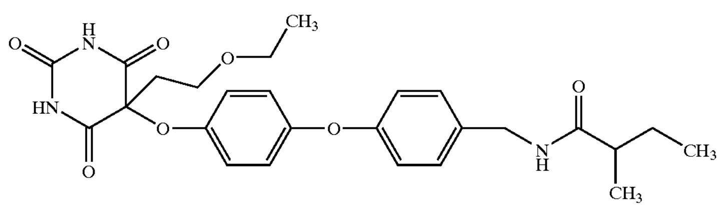 | 497.553 | 498.2 |
| 46 | 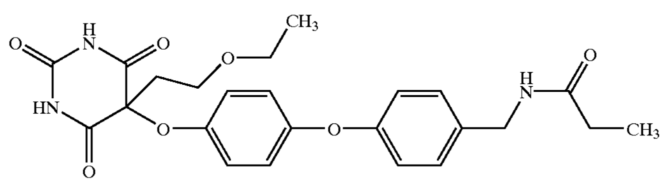 | 469.499 | 470.3 |
| 47 | 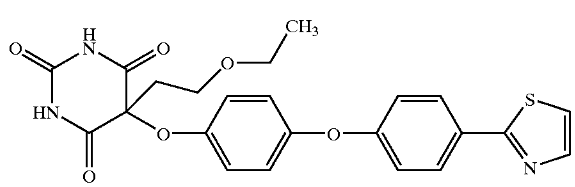 | 467.504 | 468.2 |
| 48 | 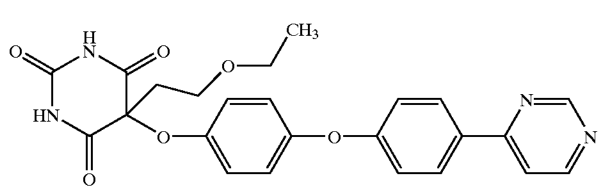 | 462.466 | |

TABLE 1-continued

| EXAMPLE NUMBER | STRUCTURE | MOLECULAR WEIGHT | APCI MS [M + H]+ |
|---|---|---|---|
| 49 | 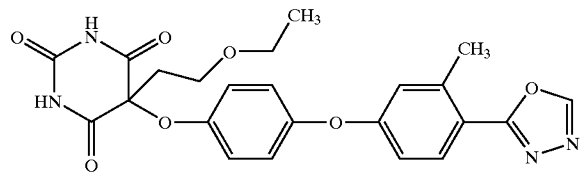 | 466.454 | 467.1 |
| 50 | 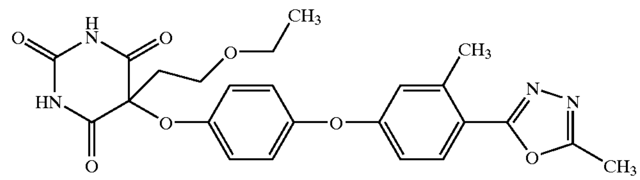 | 480.481 | |
| 51 | 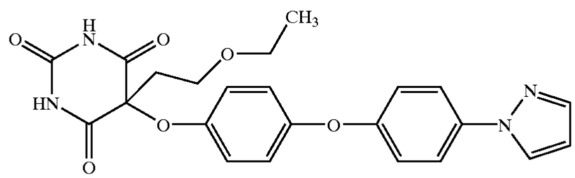 | 450.455 | |
| 52 | 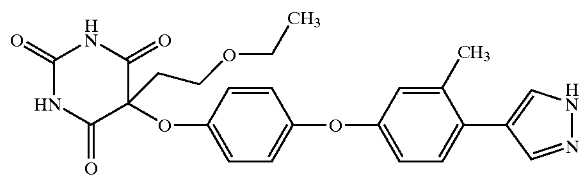 | 464.482 | 465.1 |
| 53 | 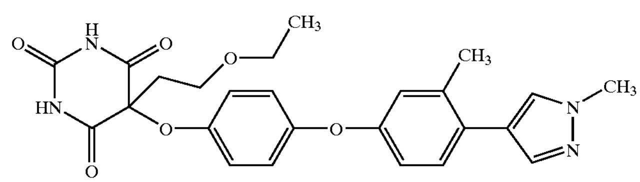 | 478.509 | 479.1 |
| 54 | 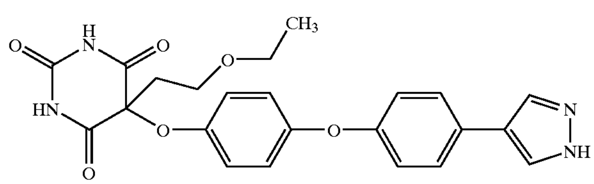 | 450.455 | |
| 55 | 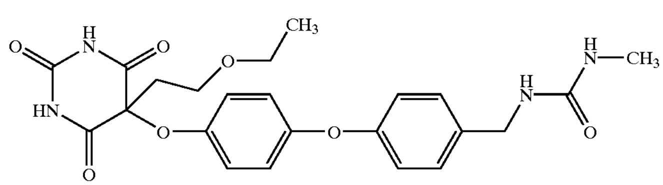 | 470.486 | 471.1 |
| 56 | 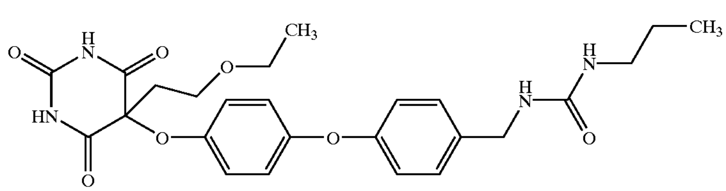 | 498.54 | 499.2 |

TABLE 1-continued

| EXAMPLE NUMBER | STRUCTURE | MOLECULAR WEIGHT | APCI MS [M + H]+ |
|---|---|---|---|
| 57 | 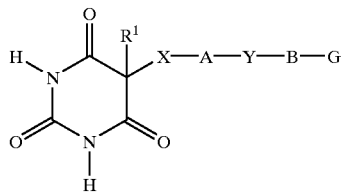 | 496.525 | 497.1 |

What is claimed is:

1. A compound of the formula $$\text{I}$$

(structure shown with barbiturate ring substituted by $R^1$ and $X\text{—}A\text{—}Y\text{—}B\text{—}G$)

wherein A is optionally substituted $(C_6\text{-}C_{10})$aryl or $(C_1\text{-}C_{10})$heteroaryl;

B is optionally substituted $(C_6\text{-}C_{10})$aryl, $(C_3\text{-}C_8)$ cycloalkyl, $(C_1\text{-}C_{10})$heteroaryl, $(C_1\text{-}C_{10})$heterocyclic, $(C_6\text{-}C_{10})$aryl-$(C_1\text{-}C_4)$alkyl, $(C_3\text{-}C_8)$cycloalkyl-$(C_1\text{-}C_4)$alkyl, $C_1\text{-}C_{10}$)heteroaryl-$(C_1\text{-}C_4)$alkyl or $(C_1\text{-}C_{10})$heterocyclic-$(C_1\text{-}C_4)$alkyl; wherein each of the aforesaid $(C_3\text{-}C_8)$cycloalkyl or $(C_1\text{-}C_{10})$ heterocyclic may optionally contain one or two double bonds;

wherein A and B may be independently optionally substituted on any of the ring carbon atoms capable of forming an additional bond by one or two substituents independently selected from F, Cl, Br, CN, OH, $(C_1\text{-}C_4)$alkyl, $(C_1\text{-}C_4)$perfluoroalkyl, $(C_1\text{-}C_4)$ perfluoroalkoxy, $(C_1\text{-}C_4)$alkoxy, and $(C_3\text{-}C_8)$ cycloalkyloxy;

X is selected from the group consisting of oxygen, >C=O, sulfur, >SO$_2$, >S=O, >NR$^{10}$, —CH$_2$O—, —OCH$_2$—, —CH$_2$S—, —CH$_2$(S=O)—, —CH$_2$SO$_2$—, —SCH$_2$—, —SOCH$_2$—, —SO$_2$CH$_2$—, —[N(R$^{10}$)]CH$_2$—, —CH$_2$[N(R$^{10}$)]—, —[N(R$^{10}$)] SO$_2$— and —SO$_2$[N(R$^{10}$)]—;

Y is selected from the group consisting of a bond, oxygen, sulfur, >C=O, >S=O, NR$^{12}$, —CH$_2$—, —CH$_2$O—, —OCH$_2$—, —CH$_2$S—, —CH$_2$(S=O)—, —CH$_2$SO$_2$—, —(S=O)CH$_2$—, SO$_2$CH$_2$—, —[N (R$^{12}$)]CH$_2$—, —CH$_2$[N(R$^{12}$)]—, —CH$_2$CH$_2$—, —CH=CH—, —[N(R$^{12}$)]—SO$_2$— and —SO$_2$[N (R$^{12}$)]—;

R$^1$ is hydrogen, $(R^2)_{2n+1}$—(C)$_n$— or $(C_3\text{-}C_8)$cycloalkyl wherein said $(C_3\text{-}C_8)$cycloalkyl may also optionally be substituted by one to two substituents independently selected from halo, $(C_1\text{-}C_4)$alkyl, $(C_1\text{-}C_4)$alkenyl, $(C_1\text{-}C_4)$alkynyl, R$^3$—, R$^3$—O—, perfluoro$(C_1\text{-}C_4)$ alkoxy, R$^3$—$(C_1\text{-}C_4)$alkyl-O—, R$^3$—(C=O)—O—, $(R^3)_2$N—(C=O)—O—, —NO$_2$, $(R^3)_2$N—, R$^3$—(C=O)—(NR$^4$)—, R$^3$—(SO$_2$)—(NR$^4$)—, R$^3$O—(C=O)—(NR$^4$)—, $(R^3)_2$N—(C=O)—(NR$^4$)—, R$^3$—S—, R$^3$—(S=O)—, R$^3$—(SO$_2$)—, $(R^3)_2$N— (SO$_2$)—, —CN, R$^3$—(C=O)—, R$^3$—O—(C=O)— and $(R^3)_2$N—(C=O)—;

n is an integer from one to ten;

each R$^2$ is independently selected from the group consisting of halo, $(C_1\text{-}C_4)$alkenyl, $(C_1\text{-}C_4)$alkynyl, R$^3$—, R$^3$—O—, perfluoro$(C_1\text{-}C_4)$alkoxy, R$^3$—(C=O)— O—, $(R^3)_2$N—(C=O)—O—, —NO$_2$, $(R^3)_2$N—, R$^3$— (SO$_2$)—(NR$^4$)—, $(R^3)_2$—N—(C=O)—, R$^3$— (C=O)—(NR$^4$)—, R$^3$O—(C=O)—(NR$^4$)—, $(R^3)_2$— N—(C=O)—(NR$^4$)—, R$^3$—S—, R$^3$—(S=O)—, R$^3$—(SO$_2$)—, $(R^3)_2$N—(SO$_2$)—, —CN, R$^3$—O— (C=O)— and R$^3$—(C=O)—; wherein not more than three of said R$^2$ substituents may be other than hydrogen and any one carbon atom of said —(C)$_n$— group can contain only one bond to a heteroatom; wherein a carbon atom of any two R$^2$ groups may be taken together with the carbons to which they are attached to form a four to ten membered ring;

each R$^3$ is independently selected from the group consisting of hydrogen, $(C_1\text{-}C_4)$alkyl, $(C_6\text{-}C_{10})$aryl, $(C_3\text{-}C_8)$cycloalkyl, $(C_1\text{-}C_{10})$heteroaryl and $(C_1\text{-}C_{10})$ heterocyclyl; wherein each R$^3$ may be optionally substituted on any carbon atom able to support an additional substituent, by one to three substituents per alkyl moiety or by one to three substituents per ring, independently selected from the group consisting of halo, hydroxy, amino, —CN, $(C_1\text{-}C_4)$alkyl, $(C_1\text{-}C_4)$alkoxy, $(C_1\text{-}C_4)$alkyl-NH—, [$(C_1\text{-}C_4)$alkyl]$_2$—N—, $(C_6\text{-}C_{10})$ aryl, $(C_3\text{-}C_8)$cycloalkyl, $(C_1\text{-}C_{10})$heteroaryl and $(C_1\text{-}C_{10})$heterocyclyl; wherein said $(C_3\text{-}C_8)$cycloalkyl and $(C_1\text{-}C_{10})$heterocyclyl may also optionally be substituted by oxo; wherein said $(C_1\text{-}C_{10})$heteroaryl and $(C_1\text{-}C_{10})$heterocyclyl may optionally be substituted on any ring nitrogen atom able to support an additional substituent by one to two substituents per ring independently selected from the group consisting of $(C_1\text{-}C_4)$alkyl, $(C_1\text{-}C_4)$alkyl-(C=O)—, $(C_6\text{-}C_{10})$aryl, $(C_3\text{-}C_8)$cycloalkyl, $(C_1\text{-}C_{10})$heteroaryl and $(C_1\text{-}C_{10})$ heterocyclyl;

wherein said R$^3$ group may optionally be taken together with an R$^4$ group to form a three to eight membered ring; wherein two of said R$^4$ groups may be taken together to form a three to eight membered ring;

R$^4$ wherever it occurs is independently selected from hydrogen and $(C_1\text{-}C_4)$alkyl;

G is R$^5$— or R$^6$—(CHR$^{13}$)$_p$—; wherein G is a substituent on any ring carbon atom of B capable of forming an additional bond and is oriented at a position other than alpha to the point of attachment of the B ring to Y;

p is an integer from one to six;

wherein R$^5$ is selected from the group consisting of R$^7$—, R$^{11}$—O—, R$^7$—$(C_1\text{-}C_4)$alkyl-O—, R$^8$—(C=O)—

O—, $H_2N(C=O)$—O—, $H_2N(C=O)$—O—, $R^8$—NH(C=O)—O—, $(R^8)_2N(C=O)$—O—, $R^8$—S—, $R^8$—(S=O)—, $R^8$—$(SO_2)$—, $H_2N$—$(SO_2)$—, $R^8$—NH—$(SO_2)$—, $(R^8)_2N$—$(SO_2)$—, formyl, $R^8$—(C=O)—, HO—(C=O)—, $R^8$—O—(C=)—, $H_2N$—(C=O)—, $R^8NH$—(C=O)—, $(R^8)_2N$—(C=O)—, —$NO_2$, $NH_2$, $R^8$—NH—, $(R^8)_2N$—, H(C=O)—($NR^9$)—, $R^8$—(C=O)—($NR^9$)—, $H_2N$—(C=O)—($NR^9$)—, $R^8NH$—(C=O)—($NR^9$)—, $(R^8)_2N$—(C=O)—($NR^9$)—, $R^8O$—(C=O)—($NR^9$)—, $R^8$—$(SO_2)$—NH— and $R^8$—$(SO_2)$—($NR^9$)—;

$R^6$ is selected from the group consisting of $(C_1$–$C_4)$alkyl, $(C_1$–$C_4)$alkenyl, $(C_1$–$C_4)$alkynyl, $R^7$, OH, $R^8$—O—, $R^8$—$(C_1$–$C_4)$alkyl-O—, perfluoro$(C_1$–$C_4)$alkoxy, $R^8$—(C=O)—O—, $H_2N(C=O)$—O—, $R^8$—NH(C=O)—O—, $(R^8)_2N(C=O)$—O—, $R^8$—(S=O)—, $R^8$—$(SO_2)$—, $H_2N$—$(SO_2)$—, $R^8$—NH(C=O)—$(R^8)_2N$(C=O)—O—,$R^8$—S—, $R^8$—$(SO_2)$—, $(R^8)_2N$—$(SO_2)$—, formyl, —CN, $R^8$—(C=O)—, HO—(C=O)—, $R^8$—O—(C=O)—, $H_2N$—(C=O)—, $R^8NH$—(C=O)—, $(R^8)_2N$—(C=O)—, —$NO_2$, $NH_2$, $R^8$—NH—, $(R^8)_2N$—, H(C=O)—($NR^9$)—, $R^8$—(C=O)—($NR^9$)—, $(R^8)_2N$—(C=O)—($NR^9$)—, $R^8O$—(C=O)—$NR^9$)—, $R^8NH$—(C=O)—($NR^9$)—, ($NR^9$)—, $R^8NH$—(C=O)—($NR^9$)—, $R^8$—$(SO_2)$—NH— and $R^8$—$(SO_2)$—($NR^9$)—;

$R^7$ is selected from the group consisting of $(C_6$–$C_{10})$aryl. $(C_3$–$C_8)$cycloalkyl, $(C_1$–$C_{10})$heteroaryl and $(C_1$–$C_{10})$heterocyclyl; wherein said $(C_6$–$C_{10})$aryl, $(C_3$–$C_8)$cycloalkyl, $(C_1$–$C_{10})$heteroaryl and $(C_1$–$C_{10})$heterocyclyl moieties may be optionally substituted on any of the ring carbon atoms capable of forming an additional bond by one to three substituents per ring independently selected from F, Cl, Br, CN, OH, $(C_1$–$C_4)$alkyl, $(C_1$–$C_4)$perfluoroalkyl, $(C_1$–$C_4)$perfluoroalkoxy, $(C_1$–$C_4)$alkoxy, amino, $(C_1$–$C_4)$alkyl-NH—, $[(C_{1-C4})$alkyl$]_2$-N— and $(C_3$–$C_8)$cycloalkyloxy; wherein said $(C_3$–$C_8)$cycloalkyl and $(C_1$–$C_{10})$heterocyclyl moieties may also optionally be substituted by oxo; wherein said $(C_1$–$C_{10})$heteroaryl and $(C_1$–$C_{10})$heterocyclyl moieties may optionally be substituted on any ring nitrogen atom able to support an additional substituent by one to two substituents per ring independently selected from the group consisting of $(C_1$–$C_4)$alkyl and $(C_1$–$C_4)$alkyl-(C=O)—;

$R^8$ is selected from the group consisting of $(C_1$–$C_4)$alkyl, $(C_6$–$C_{10})$aryl, $(C_3$–$C_8)$cycloalkyl, $(C_1$–$C_{10})$heteroaryl and $(C_1$–$C_{10})$heterocyclyl: wherein each $R^8$ may be optionally substituted on any carbon atom able to support an additional substituent, by one to three substituents per alkyl moiety or by one to three substituents per ring, independently selected from the group consisting of F, Cl, Br, CN, OH, $(C_1$–$C_4)$alkyl, $(C_1$–$C_4)$perfluoroalkyl, $(C_1$–$C_4)$perfluoroalkoxy, $(C_1$–$C_4)$alkoxy, and $(C_3$–$C_8)$cycloalkyloxy; wherein said $(C_3$–$C_8)$cycloalkyl and $(C_1$–$C_{10})$heterocyclyl may also optionally be substituted by oxo; wherein said $(C_1$–$C_{10})$heteroaryl and $(C_1$–$C_{10})$heterocyclyl may also optionally be substituted on any ring nitrogen atom able to support an additional substituent by one to two substituents per ring independently selected from the group consisting of $(C_1$–$C_4)$alkyl and $(C_1$–$C_4)$alkyl-(C=O)—; wherein two of said $R^8$ may optionally be taken together with the heteroatom to which they are attached to form a three to eight membered ring;

$R^9$ wherever it occurs is independently selected from hydrogen and $(C_1$–$C_4)$alkyl; wherein said $R^8$ and $R^9$ may optionally be taken together with the heteroatoms to which they are attached to form a three to eight membered ring;

$R^{10}$ wherever it occurs is independently selected from hydrogen and $(C_1$–$C_4)$alkyl;

$R^{11}$ is selected from the group consisting of $(C_6$–$C_{10})$aryl, $(C_1$–$C_{10})$heteroaryl and $(C_1$–$C_{10})$heterocyclyl; wherein said $(C_6$–$C_{10})$aryl, $(C_1$–$C_{10})$heteroaryl and $(C_1$–$C_{10})$heterocyclyl moieties may be optionally substituted on any of the ring carbon atoms capable of forming an additional bond by one to three substituents per ring independently selected from F, Cl, Br, CN, OH, $(C_1$–$C_4)$alkyl, $(C_1$–$C_4)$perfluoroalkyl, $(C_1$–$C_4)$perfluoroalkoxy, $(C_1$–$C_4)$alkoxy, and $(C_3$–$C_8)$cycloalkyloxy; wherein said $(C_1$–$C_{10})$heterocyclyl may also optionally be substituted by oxo;

wherein said $C_1$–$C_{10}$)heteroaryl and $(C_1$–$C_{10})$heterocyclyl may optionally be substituted on any ring nitrogen atom able to support an additional substituent by one to two substituents per ring independently selected from the group consisting of $(C_1$–$C_4)$alkyl and $(C_1$–$C_4)$alkyl-(C=O)—;

$R^{12}$ wherever it occurs is independently selected from hydrogen and $(C_1$–$C_4)$alkyl;

$R^{13}$ is independently selected from hydrogen and $(C_1$–$C_4)$ alkyl: wherein $R_{13}$ may optionally be taken together with $R^6$ to form a four to 10 membered ring;

or a pharmaceutically acceptable salt thereof.

2. A compound of the formula

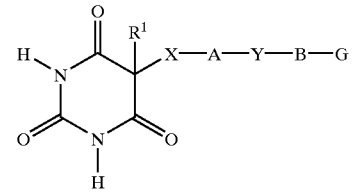

I wherein A is optionally substituted $(C_6$–$C_{10})$aryl or $(C_1$–$C_{10})$heteroaryl;

B is optionally substituted $(C_6$–$C_{10})$aryl, $(C_3$–$C_8)$cycloalkyl, $(C_1$–$C_{10})$heteroaryl, $(C_1$–$C_{10})$heterocyclic; $(C_6$–$C_{10})$aryl-$(C_1$–$C_4)$alkyl, $(C_3$–$C_8)$cycloalkyl-$(C_1$–$C_4)$alkyl, $(C_1$–$C_{10})$heteroaryl-$(C_1$–$C_4)$alkyl or $(C_1$–$C_{10})$heterocyclic-$(C_1$–$C_4)$alkyl; wherein each of the aforesaid $(C_3$–$C_8)$cycloalkyl or $(C_1$–$C_{10})$heterocyclic may optionally contain one or two double bonds;

wherein A and B may be independently optionally substituted on any of the ring carbon atoms capable of forming an additional bond by one or two substituents independently selected from F, Cl, Br, CN, OH, $(C_1$–$C_4)$alkyl, $(C_1$–$C_4)$perfluoroalkyl, $(C_1$–$C_4)$perfluoroalkoxy, $(C_1$–$C_4)$alkoxy, and $(C_3$–$C_8)$cycloalkyloxy;

X is oxygen, —$OCH_2$— or —$CH_2O$—; Y is selected from the group consisting of a bond, oxygen, sulfur, >C=O, >$SO_2$, >S=O, >$NR^{12}$, —$CH_2$—, —$CH_2O$—, and —$OCH_2$—, —$CH_2S$—, —$CH_2(S=O)$—, —$CH_2SO_2$—, —$SCH_2$—, —(S=O)$CH_2$—, —$SO_2$—, —[N($R^{12}$)]$CH_2$—, —$CH_2$[N($R^{12}$)]—, —$CH_2CH_2$—, —CH=CH—, —[N($R^{12}$)]—$SO_2$— and —$SO_2$[N($R^{12}$)]—;

$R^1$ is hydrogen, $(R^2)_{2n+1}$—$(C)_n$— or $(C_3$–$C_8)$cycloalkyl wherein said $(C_3$–$C_8)$cycloalkyl may also optionally be substituted by one to two substituents independently selected from halo, $(C_1-C_4)$alkyl, $(C_1-C_4)$alkenyl, $(C_1-C_4)$alkynyl, $R^3$—, $R^3$—O—, perfluoro$(C_1-C_4)$alkoxy, $R^3$—$(C_1-C_4)$alkyl-O—, $R^3$—(C=O)—O—, $(R^3)_2$N—(C=O)—O—, —NO$_2$, $(R^3)_2$N—, $R^3$—(C=O)—(NR$^4$)—, $R^3$—(SO$_2$)—(NR$^4$)—, $R^3$O—(C=O)—(NR$^4$)—, $(R^3)_2$—N—(C=O)—(NR$^4$)—, $R^3$—S—, $R^3$—(S=O)—, $R^3$—(SO$_2$)—, $(R^3)_2$N—(SO$_2$)—, —CN, $R^3$—(C=O)—, $R^3$—O—(C=O)— and $(R^3)_2$N—(C=O)—;

n is an integer from one to ten;

each $R^2$ is independently selected from the group consisting of halo, $(C_1-C_4)$alkenyl, $(C_1-C_4)$alkynyl, $R^3$—, $R^3$—O—, perfluoro$(C_1-C_4)$alkoxy, $R^3$—(C=O)—O—, $(R^3)_2$N—(C=O)—O—, —NO$_2$, $(R^3)_2$N—, $R^3$—(SO$_2$)—(NR$^4$)—, $(R^3)_2$—N—(C=O)—, $R^3$—(C=O)—(NR$^4$)—, $R^3$O—(C=O)—(NR$^4$)—, $(R^3)_2$—N—(C=O)—(NR$^4$)—, $R^3$—S—, $R^3$—(S=O)—, $R^3$—(SO$_2$)—, $(R^3)_2$N—(SO$_2$)—, —CN, $R^3$—O—(C=O)— and $R^3$—(C=O)—; wherein not more than three of said $R^2$ substituents may be other than hydrogen and any one carbon atom of said —(C)$_n$— group can contain only one bond to a heteroatom; wherein a carbon atom of any two $R^2$ groups may be taken together with the carbons to which they are attached to form a four to ten membered ring;

each $R^3$ is independently selected from the group consisting of hydrogen, $(C_1-C_4)$alkyl, $(C_6-C_{10})$aryl, $(C_3-C_8)$cycloalkyl, $(C_1-C_{10})$heteroaryl and $(C_1-C_{10})$heterocyclyl; wherein each $R^2$ may be optionally substituted on any carbon atom able to support an additional substituent, by one to three substituents per alkyl moiety or by one to three substituents per ring, independently selected from the group consisting of halo, hydroxy, amino, —CN, $(C_1-C_4)$alkyl, $(C_1-C_4)$alkoxy, $(C_1-C_4)$alkyl-NH—, [$(C_1-C_4)$alkyl]$_2$-N—, $(C_6-C_{10})$aryl, $(C_3-C_8)$cycloalkyl, $(C_1-C_{10})$heteroaryl and $(C_1-C_{10})$heterocyclyl; wherein said $(C_3-C_8)$cycloalkyl and $(C_1-C_{10})$heterocyclyl may also optionally be substituted by oxo; wherein said $(C_1-C_{10})$heteroaryl and $(C_1-C_{10})$heterocyclyl may optionally be substituted on any ring nitrogen atom able to support an additional substituent by one to two substituents per ring independently selected from the group consisting of $(C_1-C_4)$alkyl, $(C_1-C_4)$alkyl-(C=O)—, $(C_6-C_{10})$aryl, $(C_3-C_8)$cycloalkyl, $(C_1-C_{10})$heteroaryl and $(C_1-C_{10})$heterocyclyl;

wherein said $R^3$ group may optionally be taken together with an $R^4$ group to form a three to eight membered ring; wherein two of said $R^4$ groups may be taken together to form a three to eight membered ring;

$R^4$ wherever it occurs is independently selected from hydrogen and $(C_1-C_4)$alkyl;

G is $R^5$— or $R^6$—(CHR$^{13}$)—; wherein G is a substituent on any ring carbon atom of B capable of forming an additional bond and is oriented at a position other than alpha to the point of attachment of the B ring to Y;

p is an integer from one to six;

wherein $R^5$ is selected from the group consisting of $R^7$—, $R^{11}$—O—, $R^7$—$(C_1-C_4)$alkyl-O—, $R^8$—(C=O)—O—, H$_2$N(C=O)—O—, $R^8$—NH(C=O)—O—, $(R^8)_2$N(C=O)—O—, $R^8$—S—, $R^8$—(S=O)—, $R^8$—(SO$_2$)—, H$_2$N—(SO$_2$)—, $R^8$—NH—(SO$_2$)—, $(R^8)_2$N—(SO$_2$)—, formyl, $R^8$—(C=O)—, HO—(C=O)—, $R^8$—O—(C=O)—, H$_2$N—(C=O)—, $R^8$NH—(C=O)—, $(R^8)_2$N—(C=O)—, —NO$_2$, —NH$_2$, $R^8$—NH—, $(R^8)_2$N—, H(C=O)—(NR$^9$)—, $R^8$—(C=O)—(NR$^9$)—, H$_2$N—(C=O)—(NR$^9$)—, $R^8$NH—(C=O)—(NR$^9$)—, $(R^8)_2$N—(C=O)—(NR$^9$)—, $R^8$O—(C=O)—(NR$^9$)—, $R^8$—(C=O)—(NR$^9$)—; $R^8$—(SO$_2$)—NH— and $R^8$—(SO$_2$)—(NR$^9$)—;

$R^6$ is selected from the group consisting of $(C_1-C_4)$alkenyl, $(C_1-C_4)$alkynyl, $R^7$, OH, $R^8$—O—, $R^8$—$(C_1-C_4)$alkyl-O—, perfluoro$(C_1-C_4)$alkoxy, $R^8$—(C=O)—O—, H$_2$N(C=O)—O—, $R^8$—NH(C=O)—O—, $(R^8)_2$N(C=O)—O—, $R^8$—S—, $R^8$—(S=O)—, $R^8$—(SO$_2$)—, H$_2$N—(SO$_2$)—, $R^8$—NH—(SO$_2$)—, $(R^8)_2$N—(SO$_2$)—, formyl, —CN, $R^8$—(C=O)—, HO—(C=O)—, $R^8$—O—(C=O)—, H$_2$N—(C=O)—, $R^8$NH—(C=O)—, $(R^8)_2$N—(C=O)—, —NO$_2$, NH$_2$, $R^8$—NH—, $(R^8)_2$N—, H(C=O)—(NR$^9$)—, $R^8$—(C=O)—(NR$^9$)—, H$_2$N—(C=O)—(NR$^9$)—, $R^8$NH—(C=O)—(NR$^9$)—, $(R^8)_2$N—(C=O)—(NR$^9$)—, $R^8$—(C=O)—(NR$^9$)—, $R^8$—(SO$_2$)—NH— and $R^8$—(SO$_2$)—(NR$^9$)—;

$R^7$ is selected from the group consisting of $(C_6-C_{10})$aryl, $(C_3-C_8)$cycloalkyl, $(C_1-C_{10})$heteroaryl and $(C_1-C_{10})$heterocyclyl; wherein said $(C_6-C_{10})$aryl, $(C_3-C_8)$cycloalkyl, $(C_1-C_{10})$heteroaryl and $(C_1-C_{10})$heterocyclyl moieties may be optionally substituted on any of the ring carbon atoms capable of forming an additional bond by one to three substituents per ring independently selected from F, Cl, Br, CN, OH, (C–C$_4$) alkyl, $(C_1-C_4)$perfluoroalkyl, $(C_1-C_4)$perfluoroalkoxy, $(C_1-C_4)$alkoxy, amino, $(C_1-C_4)$alkyl-NH—, [$(C_1-C_4)$alkyl]$_2$-N— and $(C_3-C_8)$cycloalkyloxy; wherein said $(C_3-C_8)$cycloalkyl and $(C_1-C_{10})$heterocyclyl moieties may also optionally be substituted by oxo; wherein said $(C_1-C_{10})$heteroaryl and $(C_1-C_{10})$heterocyclyl moieties may optionally be substituted on any ring nitrogen atom able to support an additional substituent by one to two substituents per ring independently selected from the group consisting of $(C_1-C_4)$alkyl and $(C_1-C_4)$alkyl-(C=O)—;

$R^8$ is selected from the group consisting of $(C_1-C_4)$alkyl, $(C_6-C_{10})$aryl, $(C_3-C_8)$cycloalkyl, $(C_1-C_{10})$heteroaryl and $(C_1-C_{10})$heterocyclyl; wherein each $R^8$ may be optionally substituted on any carbon atom able to support an additional substituent, by one to three substituents per alkyl moiety or by one to three substituents per ring, independently selected from the group consisting of F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy, and $(C_3-C_8)$cycloalkyloxy; wherein said $(C_3-C_8)$cycloalkyl and $(C_1-C_{10})$heterocyclyl may also optionally be substituted by oxo; wherein said $(C_1-C_{10})$heteroaryl and $(C_1-C_{10})$heterocyclyl may also optionally be substituted on any ring nitrogen atom able to support an additional substituent by one to two substituents per ring independently selected from the group consisting of $(C_1-C_4)$alkyl and $(C_1-C_4)$alkyl-(C=O)—; wherein two of said $R^8$ may optionally be taken together with the heteroatom to which they are attached to form a three to eight membered ring;

$R^9$ wherever it occurs is independently selected from hydrogen and $(C_1-C_4)$alkyl; wherein said $R^8$ and $R^9$ may optionally be taken together with the heteroatoms to which they are attached to form a three to eight membered ring;

$R^{10}$ wherever it occurs is independently selected from hydrogen and $(C_1-C_4)$alkyl;

67

$R^{11}$ is selected from the group consisting of $(C_6-C_{10})$aryl, $(C_1-C_{10})$heteroaryl and
$(C_1-C_{10})$heterocyclyl; wherein said $(C_6-C_{10})$aryl, $(C_1-C_{10})$heteroaryl and $(C_1-C_{10})$heterocyclyl moieties may be optionally substituted on any of the ring carbon atoms capable of forming an additional bond by one to three substituents per ring independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy, and
$(C_3-C_8)$cycloalkyloxy; wherein said $(C_1-C_{10})$heterocyclyl may also optionally be substituted by oxo;
wherein said $(C_1-C_{10})$heteroaryl and $(C_1-C_{10})$heterocyclyl may optionally be substituted on any ring nitrogen atom able to support an additional substituent by one to two substituents per ring independently selected from the group consisting of $(C_1-C_4)$alkyl and $(C_1-C_4)$alkyl-(CO)—;
$R^{12}$ wherever it occurs is independently selected from hydrogen and $(C_1-C_4)$alkyl;
$R^{13}$ is independently selected from hydrogen and $(C_1-C_4)$alkyl; wherein $R^{13}$ may optionally be taken together with $R^6$ to form a four to 10 membered ring;
or a pharmaceutically acceptable salt thereof.

3. A compound according to claim 2, wherein Y is oxygen, —OCH$_2$— or CH$_2$O—.

4. A compound according to claim 3, wherein A is optionally substituted phenyl.

5. A compound according to claim 4, wherein B is optionally substituted phenyl or $(C_1-C_{10})$heteroaryl.

6. A compound according to claim 5, wherein G is $R^5$—.

7. A compound according to claim 5, wherein $R^5$— is $R^7$, wherein $R^7$ is $(C_1-C_{10})$heteroaryl.

8. A compound according to claim 5, wherein $R^1$ is $(R^2)_{2n+1}$—(C)$_n$—, is an integer from one to ten;
at least one $R^2$ is independently selected from the group consisting of $R^3$—, $R^3$—O—, $(R^3)_2$N—, $R^3$—S—, $R^3$—(S=O)—, $R^3$—(SO$_2$)—, $R^3$—(SO$_2$)—(NR$_4$)—, $R^3$—NH—(SO$_2$)—, $(R^3)_2$N—(SO$_2$—, $R^3$—(C=O)—(NR$^4$)—, $R^3$—(C=O)—O—, $R^3$—O—(C=O)— and $R^3$—(C=O)—; and
each $R^3$ is independently selected from the group consisting of hydrogen and $(C_1-C_4)$alkyl; wherein each $R^3$ $(C_1-C_4)$alkyl moiety may be optionally substituted by one to three substituents independently selected from the group consisting of halo, hydroxy, amino, —CN, $(C_1-C_4)$alkyl, $(C_1-C_4)$alkoxy, $(C_1-C_4)$alkyl-NH—, [$(C_1-C_4)$alkyl]$_2$-N—$(C_6-C_{10})$aryl, $(C_3-C_8)$cycloalkyl, $(C_1-C_{10})$heteroaryl and $(C_1-C_{10})$heterocyclyl; wherein said $R^3$ group may optionally be taken together with $R^4$ to form a three to eight membered ring.

9. A compound according to claim 1, wherein said compound is selected from the group consisting of:

5-(2-Ethoxy-ethyl)-5-[4-(4-thiazol-2-yl-phenoxy)-phenoxy]-pyrimidine-2,4,6-trione;

5-(2-Ethoxy-ethyl)-5-{4-[4-(2-methyl-2H-pyrazol-3-yl)-phenoxy]-phenoxy}-pyrimidine-2,4,6-trione;

5-(2-Ethoxy-ethyl)-5-{4-[4-(1-methyl-1H-pyrazol-3-yl)-phenoxy]-phenoxy}-pyrimidine-2,4,6-trione;

5-(4-{4-[5-(2Ethoxy-ethyl)-2,4,6-trioxo-hexahydro-pyrimidin-5-yloxy]phenoxy}-phenyl)-pentanenitrile;

5-(2-Ethoxy-ethyl)-5-{4-[4-(2-methyl-thiazol-4-yl)-phenoxy]-phenoxy}-pyrimidine-2,4,6-trione;

5-(2-Ethoxy-ethyl)-5-{4-[4-(1H-pyrazol-3-yl)-phenoxy]-phenoxy}-pyrmidine-2,4,6-trione;

68

5-(2-Ethoxy-ethyl)-5-[4-(4-oxazol-5-yl-phenoxy)-phenoxy]-pyrimidine-2,4,6-trione; and 5-(2-Ethoxy-ethyl)-5-[4-(4-pyrimidin-4-yl-phenoxy)-phenoxy]-pyrimidine-2,4,6-trione; or a pharmaceutically acceptable salt thereof.

10. A compound according to claim 1, wherein Y is oxygen, —OCH$_2$— or —CH$_2$O—.

11. A compound of the formula wherein A is optionally substituted $(C_6-C_{10})$aryl or $(C_1-C_{10})$heteroaryl;

B is optionally substituted $(C_6-C_{10})$aryl, $(C_3-C_8)$cycloalkyl, $(C_1-C_{10})$heteroaryl, $(C_1-C_{10})$heterocyclic; $(C_6-C_{10})$aryl-$(C_1-C_4)$alkyl, $(C_3-C_8)$cycloalkyl-$(C_1-C_4)$alkyl, $(C_1-C_{10})$heteroaryl-$(C_1-C_4)$alkyl or $(C_1-C_{10})$heterocyclic-$(C_1-C_4)$alkyl; wherein each of the aforesaid $(C_3-C_8)$cycloalkyl or $(C_1-C_{10})$heterocyclic may optionally contain one or two double bonds;

wherein A and B may be independently optionally substituted on any of the ring carbon atoms capable of forming an additional bond by one or two substituents independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy, and $(C_3-C_8)$cycloalkyloxy;

X is selected from the group consisting of oxygen, >C=O, sulfur, >SO$_2$, >S=O, >NR$^{10}$, —CH$_2$O—, —OCH$_2$—, —CH$_2$S—, —CH$_2$(S=O)—, —CH$_2$SO$_2$—, —SCH$_2$—, —SOCH$_2$—, —SO$_2$CH$_2$—, —[N(R$^{10}$)]CH$_2$—, —CH$_2$[N(R$^{10}$)]—, —[N(R$^{10}$)]SO$_2$— and —SO$_2$[N(R$^{10}$)]—;

Y is selected from the group consisting of a bond, oxygen, sulfur, >C=O, >S=O, NR$^{12}$, —CH$_2$—, —CH$_2$O—, —OCH$_2$—, —CH$_2$S—, —CH$_2$(S=O)—, —CH$_2$SO$_2$—, —(S=O)CH$_2$—, SO$_2$CH$_2$—, —[N(R$^{12}$)]CH$_2$—, —CH$_2$[N(R$^{12}$)]—, —CH$_2$CH$_2$—, —CH=CH—, —[N(R$^{12}$)]—SO$_2$— and —SO$_2$[N(R$^{12}$)]—;

$R^1$ is hydrogen, $(R^2)_{2n+1}$—(C)$_n$— or $(C_3-C_8)$cycloalkyl wherein said $(C_3-C_8)$cycloalkyl may also optionally be substituted by one to two substituents independently selected from halo, $(C_1-C_4)$alkyl, $(C_1-C_4)$alkenyl, $(C_1-C_4)$alkynyl, R$^3$—, R$^3$—O—, perfluoro$(C_1-C_4)$alkoxy, R$^3$—$(C_1-C_4)$alkyl-O—, R$^3$—(C=O)—O—, $(R^3)_2$N—(C=O)—O—, —NO$_2$, $(R^3)_2$N—, R$^3$—(C=O)—(NR$^4$)—, R$^3$—(SO$_2$)—(NR$^4$)—, R$^3$O—(C=O)—(NR$^4$)—, $(R^3)_2$N—(C=O)—(NR$^4$)—, R$^3$—S—, R$^3$—(S=O)—, R$^3$—(SO$_2$)—, $(R^3)_2$N—(SO$_2$)—, —CN, R$^3$—(C=O)—, R$^3$—O—(C=O)— and $(R^3)_2$N—(C=O)—n is an integer from one to ten;

each $R^2$ is independently selected from the group consisting of halo, $(C_1-C_4)$alkenyl, $(C_1-C_4)$alkynyl, R$^3$—, R$^3$—O—, perfluoro$(C_1-C_4)$alkoxy, R$^3$—(C=O)—O—, $(R^3)_2$N—(C=O)—O—, —NO$_2$, $(R^3)_2$N—, R$^3$—(SO$_2$)—(NR$^4$)—, $(R^3)_2$—N—(C=O)—, R$^3$—(C=O)—(NR$^4$)—, R$^3$O—(C=O)—(NR$^4$)—, $(R^3)_2$—

N—(C=O)—(NR$^4$)—, R$^3$—S—, R$^3$—(S=O)—, R$^3$—(SO$_2$)—, (R$^3$)$_2$N—(SO$_2$)—, —CN, R$^3$—O—(C=O)— and R$^3$—(C=O)—; wherein not more than three of said R$^2$ substituents may be other than hydrogen and any one carbon atom of said —(C)$_n$— group can contain only one bond to a heteroatom; wherein a carbon atom of any two R$^2$ groups may be taken together with the carbons to which they are attached to form a four to ten membered ring;

each R$^3$ is independently selected from the group consisting of hydrogen, (C$_1$–C$_4$)alkyl, (C$_6$–C$_{10}$)aryl, (C$_3$–C$_8$)cycloalkyl, (C$_1$–C$_{10}$)heteroaryl and (C$_1$–C$_{10}$) heterocyclyl; wherein each R$^3$ may be optionally substituted on any carbon atom able to support an additional substituent, by one to three substituents per alkyl moiety or by one to three substituents per ring, independently selected from the group consisting of halo, hydroxy, amino, —CN, (C$_1$–C$_4$)alkyl, (C$_1$–C$_4$)alkoxy, (C$_1$–C$_4$)alkyl-NH—, [(C$_1$–C$_4$)alkyl]$_2$—N—, (C$_6$–C$_{10}$) aryl, (C$_3$–C$_8$)cycloalkyl, (C$_1$–C$_{10}$)heteroaryl and (C$_1$–C$_{10}$)heterocyclyl; wherein said (C$_3$–C$_8$)cycloalkyl and (C$_1$–C$_{10}$)heterocyclyl may also optionally be substituted by oxo; wherein said (C$_1$–C$_{10}$)heteroaryl and (C$_1$–C$_{10}$)heterocyclyl may optionally be substituted on any ring nitrogen atom able to support an additional substituent by one to two substituents per ring independently selected from the group consisting of (C$_1$–C$_4$)alkyl, (C$_1$–C$_4$)alkyl-(C=O)—, (C$_6$–C$_{10}$)aryl, (C$_3$–C$_8$)cycloalkyl, (C$_1$–C$_{10}$)heteroaryl and (C$_1$–C$_{10}$) heterocyclyl;

wherein said R$^3$ group may optionally be taken together with an R$^4$ group to form a three to eight membered ring; wherein two of said R$^4$ groups may be taken together to form a three to eight membered ring;

R$^4$ wherever it occurs is independently selected from hydrogen and (C$_1$–C$_4$)alkyl;

G is R$^5$— or R$^6$—(CHR$^{13}$)$_p$—; wherein G is a substituent on any ring carbon atom of B capable of forming an additional bond and is oriented at a position other than alpha to the point of attachment of the B ring to Y;

p is an integer from one to six;

wherein R$^5$ is selected from the group consisting of R$^7$—, R$^{11}$—O—, R$^7$—(C$_1$–C$_4$)alkyl-O—, R$^8$—(C=O)—O—, H$_2$N(C=O)—O—, R$^8$—NH(C=O)—O—, (R$^8$)$_2$N(C=O)—O—, R$^8$—S—, R$^8$—(S=O)—, R$^8$—(SO$_2$)—, H$_2$N—(SO$_2$)—, R$^8$—NH—(SO$_2$)—, (R$^8$)$_2$N—(SO$_2$)—, formyl, R$^8$—(C=O)—, HO—(C=O)—, R$^8$—O—(C=)—, H$_2$N—(C=O)—, R$^8$NH—(C=O)—, (R$^8$)$_2$N—(C=O)—, —NO$_2$, NH$_2$, R$^8$—NH—, (R$^8$)$_2$N—, H(C=O)—(NR$^9$)—, R$^8$—(C=O)—(NR$^9$)—, H$_2$N—(C=O)—(NR$^9$)—, R$^8$NH—(C=O)—(NR$^9$)—, (R$^8$)$_2$N—(C=O)—(NR$^9$)—, R$^8$O—(C=O)—(NR$^9$)—, R$^8$—(SO$_2$)—NH— and R$^8$—(SO$_2$)—(NR$^9$)—;

R$^6$ is selected from the group consisting of perfluoro (C$_1$–C$_4$)alkyl, (C$_1$–C$_4$)alkenyl, (C$_1$–C$_4$)alkynyl, R$^7$, OH, R$^8$—O—, R$^8$—(C$_1$–C$_4$)alkyl-O—, perfluoro (C$_1$–C$_4$)alkoxy, R$^8$—(C=O)—O—, H$_2$N(C=O)—O—, R$^8$—NH(C=O)—O—, (R$^8$)$_2$N(C=O)—O—, R$^8$—S—, R$^8$—(S=O)—, R$^8$—(SO$_2$)—, H$_2$N—(SO$_2$)—, R$^8$—NH—(SO$_2$)—, (R$^8$)$_2$N—(SO$_2$)—, formyl, —CN, R$^8$—(C=O)—, HO—(C=O)—, R$^8$—O—(C=O)—, H$_2$N—(C=O)—, R$^8$NH—(C=O)—, (R$^8$)$_2$N—(C=O)—, —NO$_2$, NH$_2$, R$^8$—NH—, (R$^8$)$_2$N—, H(C=O)—(NR$^9$)—, R$^8$—(C=O)—(NR$^9$)—, H$_2$N—(C=O)—(NR$^9$)—, R$^8$NH—(C=O)—(NR$^9$)—, (R$^8$)$_2$N—(C=O)—(NR$^9$)—, R$^8$O—(C=O)—(NR$^9$)—, R$^8$—(SO$_2$)—NH— and R$^8$—(SO$_2$)—(NR$^9$)—;

R$^7$ is selected from the group consisting of (C$_6$–C$_{10}$)aryl. (C$_3$–C$_8$)cycloalkyl, (C$_1$–C$_{10}$)heteroaryl and (C$_1$–C$_{10}$) heterocyclyl; wherein said (C$_6$–C$_{10}$)aryl, (C$_3$–C$_8$) cycloalkyl, (C$_1$–C$_{10}$)heteroaryl and (C$_1$–C$_{10}$) heterocyclyl moieties may be optionally substituted on any of the ring carbon atoms capable of forming an additional bond by one to three substituents per ring independently selected from F, Cl, Br, CN, OH, (C$_1$–C$_4$)alkyl, (C$_1$–C$_4$)perfluoroalkyl, (C$_1$–C$_4$) perfluoroalkoxy, (C$_1$–C$_4$)alkoxy, amino, (C$_1$–C$_4$)alkyl-NH—, [(C$_{1-C4}$)alkyl]$_2$-N— and (C$_3$–C$_8$) cycloalkyloxy; wherein said (C$_3$–C$_8$)cycloalkyl and (C$_1$–C$_{10}$)heterocyclyl moieties may also optionally be substituted by oxo; wherein said (C$_1$–C$_{10}$)heteroaryl and (C$_1$–C$_{10}$)heterocyclyl moieties may optionally be substituted on any ring nitrogen atom able to support an additional substituent by one to two substituents per ring independently selected from the group consisting of (C$_1$–C$_4$)alkyl and (C$_1$–C$_4$)alkyl-(C=O)—;

R$^8$ is selected from the group consisting of (C$_1$–C$_4$)alkyl, (C$_6$–C$_{10}$)aryl, (C$_3$–C$_8$)cycloalkyl, (C$_1$–C$_{10}$)heteroaryl and (C$_1$–C$_{10}$)heterocyclyl: wherein each R$^8$ may be optionally substituted on any carbon atom able to support an additional substituent, by one to three substituents per alkyl moiety or by one to three substituents per ring, independently selected from the group consisting of F, Cl, Br, CN, OH, (C$_1$–C$_4$)alkyl, (C$_1$–C$_4$) perfluoroalkyl, (C$_1$–C$_4$)perfluoroalkoxy, (C$_1$–C$_4$) alkoxy, and (C$_3$—C$_8$)cycloalkyloxy; wherein said (C$_3$–C$_8$)cycloalkyl and (C$_1$–C$_{10}$)heterocyclyl may also optionally be substituted by oxo; wherein said (C$_1$–C$_{10}$)heteroaryl and (C$_1$–C$_{10}$)heterocyclyl may also optionally be substituted on any ring nitrogen atom able to support an additional substituent by one to two substituents per ring independently selected from the group consisting of (C$_1$–C$_4$)alkyl and (C$_1$–C$_4$)alkyl-(C=O)—; wherein two of said R$^8$ may optionally be taken together with the heteroatom to which they are attached to form a three to eight membered ring;

R$^9$ wherever it occurs is independently selected from hydrogen and (C$_1$–C$_4$)alkyl; wherein said R$^8$ and R$^9$ may optionally be taken together with the heteroatoms to which they are attached to form a three to eight membered ring;

R$^{10}$ wherever it occurs is independently selected from hydrogen and (C$_1$–C$_4$)alkyl;

R$^{11}$ is selected from the group consisting of (C$_6$–C$_{10}$)aryl, (C$_1$–C$_{10}$)heteroaryl and (C$_1$–C$_{10}$)heterocyclyl; wherein said (C$_6$–C$_{10}$)aryl, (C$_1$–C$_{10}$)heteroaryl and (C$_1$–C$_{10}$) heterocyclyl moieties may be optionally substituted on any of the ring carbon atoms capable of forming an additional bond by one to three substituents per ring independently selected from F, Cl, Br, CN, OH, (C$_1$–C$_4$)alkyl, (C$_1$–C$_4$)perfluoroalkyl, (C$_1$–C$_4$) perfluoroalkoxy, (C$_1$–C$_4$)alkoxy, and (C$_3$–C$_8$) cycloalkyloxy; wherein said (C$_1$–C$_{10}$)heterocyclyl may also optionally be substituted by oxo;

wherein said C$_1$–C$_{10}$)heteroaryl and (C$_1$–C$_{10}$) heterocyclyl may optionally be substituted on any ring nitrogen atom able to support an additional substituent by one to two substituents per ring independently selected from the group consisting of (C$_1$–C$_4$)alkyl and (C$_1$–C$_4$)alkyl-(C=O)—;

$R^{12}$ wherever it occurs is independently selected from hydrogen and $(C_1-C_4)$alkyl:

$R^{13}$ is independently selected from hydrogen and $(C_1-C_4)$alkyl: wherein $R_{13}$ may optionally be taken together with $R^6$ to form a four to 10 membered ring;

or a pharmaceutically acceptable salt thereof.

12. A pharmaceutical composition for the treatment of inflammatory disorders, in a mammal, comprising an amount of a compound according to claim 1 effective in such treatment and a pharmaceutically acceptable carrier.

13. A pharmaceutical composition for the treatment of inflammatory disorders in a mammal, comprising an amount of a compound according to claim 2 effective in such treatment and a pharmaceutically acceptable carrier.

14. A pharmaceutical composition for the treatment of inflammatory disorders in a mammal, comprising an amount of a compound according to claim 11 effective in such treatment and a pharmaceutically acceptable carrier.

15. A method for treating inflammatory disorders in a mammal, comprising administering to said mammal an amount of a compound according to claim 1 effective in treating said disorders.

16. A method for treating inflammatory disorders in a mammal, comprising administering to said mammal an amount of a compound according to claim 2 effective in treating said disorders.

17. A method for treating inflammatory disorders in a mammal, comprising administering to said mammal an amount of a compound according to claim 11 effective in treating said disorders.

* * * * *